(12) United States Patent
Ohkawa et al.

(10) Patent No.: US 7,008,940 B1
(45) Date of Patent: Mar. 7, 2006

(54) DIHYDROBENZOFURAN DERIVATIVES, PROCESS FOR THE PREPARING THEREOF AND AGENTS

(75) Inventors: Shigenori Ohkawa, Takatsuki (JP); Tadatoshi Hashimoto, Ibaraki (JP); Tetsuya Tsukamoto, Akashi (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 358 days.

(21) Appl. No.: 10/069,314

(22) PCT Filed: Aug. 18, 2000

(86) PCT No.: PCT/JP00/05524

§ 371 (c)(1),
(2), (4) Date: Feb. 13, 2002

(87) PCT Pub. No.: WO01/14385

PCT Pub. Date: Jan. 3, 2001

(30) Foreign Application Priority Data

Aug. 20, 1999 (JP) ................................ 11/234719

(51) Int. Cl.
*A61P 9/00* (2006.01)
*A61P 25/00* (2006.01)
*A61K 31/407* (2006.01)
*A61K 31/55* (2006.01)
*C07D 491/48* (2006.01)

(52) U.S. Cl. ................. 514/217.01; 514/321; 514/411; 540/594; 546/198; 548/430

(58) Field of Classification Search ........... 514/217.01, 514/321, 411; 540/594; 546/198; 548/430
See application file for complete search history.

(56) References Cited

U.S. PATENT DOCUMENTS

| | | | |
|---|---|---|---|
| 5,276,051 A | 1/1994 | Lesieur et al. | 514/415 |
| 5,296,482 A | 3/1994 | Peglion et al. | 514/213 |
| 5,308,866 A | 5/1994 | Lesieur et al. | 514/469 |
| 5,552,418 A | 9/1996 | Depreux et al. | 514/348 |
| 5,576,324 A | 11/1996 | Kyotani et al. | 514/291 |
| 5,661,186 A | 8/1997 | Takaki et al. | 514/630 |
| 5,843,986 A | 12/1998 | Lesieur et al. | 514/450 |
| 5,998,461 A | 12/1999 | Lesieur et al. | 514/411 |
| 6,034,239 A * | 3/2000 | Ohkawa et al. | 544/147 |
| 6,071,946 A | 6/2000 | Lesieur et al. | 514/411 |
| 6,417,213 B1 | 7/2002 | Ohkawa et al. | 514/375 |

FOREIGN PATENT DOCUMENTS

| | | |
|---|---|---|
| CA | 2 382 413 | 3/2001 |
| EP | 0 420 064 | 4/1991 |
| EP | 0 638 571 A1 | 2/1995 |
| JP | 54 163598 | 12/1979 |
| WO | WO 95/17405 | 6/1995 |
| WO | WO 95/29173 | 11/1995 |
| WO | WO 95/35320 | 12/1995 |
| WO | WO 97/32871 A1 | 9/1997 |

OTHER PUBLICATIONS

Bhalerao et al., Synthesis and Antimicrobial Activity of Dihydrofurobenzoxazolin-2(3H)-ones and Their Derivatives, Arzneimittel-Forschung, 1994, vol. 44, No. 9, pp. 1077-1079.*

Johns et al. "Alkaloids of *Choisya Ternata* H.B. & K. (Family Rutaceae). The Structure of Choisyine" Aust. J. Chem. 20:1975-81 (1967).

Dufresne, C., et al., "The synthesis of phenylhydrazines from bis(2,2,2-trichloroethyl) azodicarboxylates and electron-rich arenes," *Synthetic Communications*, vol. 27, No. 20, (1997), pp. 3613-3624.

Macor, John E., et al., "The synthesis of pyrano [3,2-e] indoles and pyrano [2,3-f] indoles as rotationally restricted phenolic analogs of the neurotransmitter serotonin," *Tetrahedron*, vol. 48, No. 6, (1992), pp. 1039-1052.

* cited by examiner

*Primary Examiner*—Brenda Coleman
(74) *Attorney, Agent, or Firm*—Elaine M. Ramesh; Mark Chao

(57) ABSTRACT

A compound represented by the formula (I):

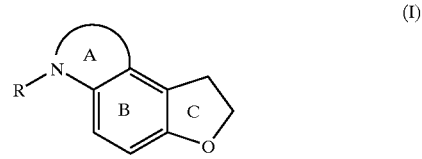

(I)

or a salt thereof exhibits excellent inhibitory activity of lipid peroxidation and is useful as an agent for inhibiting lipoperoxide production, wherein ring A denotes a non-aromatic 5- to 7-membered nitrogen-containing heterocyclic ring which may be further substituted, B ring denotes a benzene ring which may be further substituted, C ring denotes a dihydrofuran ring which may be further substituted, and R denotes hydrogen atom or an acyl group.

20 Claims, No Drawings

DIHYDROBENZOFURAN DERIVATIVES, PROCESS FOR THE PREPARING THEREOF AND AGENTS

This application is the National Stage of International Application No. PCT/JP00/05524, filed Aug. 18, 2000.

TECHNICAL FIELD

The present invention relates to novel dihydrobenzofuran derivatives having excellent lipid peroxidation inhibitory activity, a process for preparing the same and a medicament containing them.

BACKGROUND ART

As it has been revealed that production of active oxygen species in the living body and accompanying production of peroxylipid have a variety of adverse influences on the living body through membrane disorder or enzyme disorder, various attempts have been made to apply lipid peroxidation inhibitory agents to medicaments. Currently, as lipid peroxidation inhibitory agents used in the pharmaceutical field, derivatives of natural antioxidants such as vitamin C, vitamin E and P-carotene, etc. and phenol derivatives are mainly known (authored by Kenji Fukuzawa, Nippon Rinsho vol. 46, pp 2269–2276, 1988 and Sies, H., Stahl, W., Sundquist, A. R., Ann. N. Acad. Sci., vol. 669, 7–20, 1992). However, these have insufficient activities and have side effects and, therefore, they are not necessarily satisfactory practically.

On the other hand, WO97/32871 describes, as a furo[3,2-f]indole derivative, compounds represented by the formula:

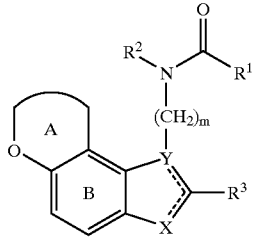

wherein $R^1$ denotes a hydrocarbon group, an optionally substituted amino group or an optionally substituted heterocyclic group, $R^2$ denotes hydrogen atom or an optionally substituted hydrocarbon group, $R^3$ denotes hydrogen atom, an optionally substituted hydrocarbon group or an optionally substituted heterocyclic group, X denotes $CHR^4$, $NR^4$, O or $S(R^4$ denotes hydrogen atom or an optionally substituted hydrocarbon group), Y denotes C, CH or N (provided that, when X denotes $CH_2$, Y is C or CH), ═══denotes a single bond or a double bond, A ring denotes an optionally substituted 5- to 7-membered oxygen atom-containing heterocyclic ring, B ring denotes an optionally substituted benzene ring, and n denotes an integer of 1 to 4, which have the excellent melatonin receptor affinity, or salts thereof, more particularly, compounds:

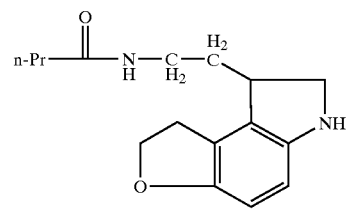

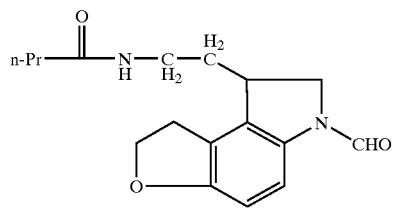

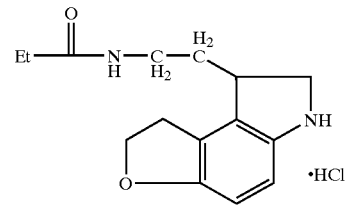

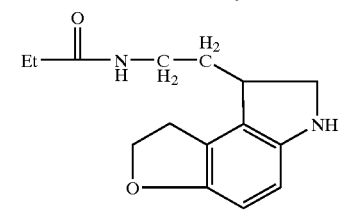

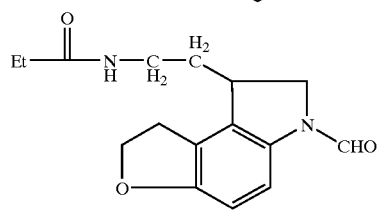

and the like.

WO93/22317 describes quinoline derivatives represented by the formula:

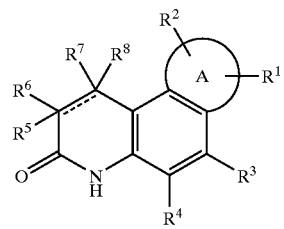

wherein A ring represents furan ring, dihydrofuran ring or dioxolane ring, $R^1$ denotes hydroxy group, carboxyl group, an alkoxycarbony group, a carbamoyl group, an alkenyl group, formyl group, cyano group, an optionally substituted alkyl group, or —C(=N—R¹⁰)—R¹ (wherein R⁹ denotes amino group or an alkyl group, R¹⁰ denotes hydrogen atom or hydroxy group), R²s are the same or different and denote hydrogen atom, an optionally substituted alkyl group, an alkenyl group, an acyl group or hydroxy group, R³ and R⁴ are the same or different and denote hydrogen atom, a halogen atom, an optionally substituted alkyl group, an optionally substituted amino group, an alkoxy group, an alkylthio group, carboxyl group, an acyl group, a carbamoyl group, cyano group or nitro group, R⁵, R⁶, R⁷ and R⁸ are the same or different and denote hydrogen atom or an alkyl group,

- - - means that a double bond formed by R⁵ and R⁸ may exist, and pharmaceutically acceptable salts which are useful as a cardiac disease treating agent, more particularly, compounds:

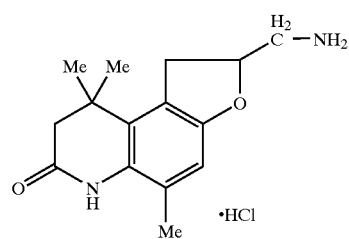

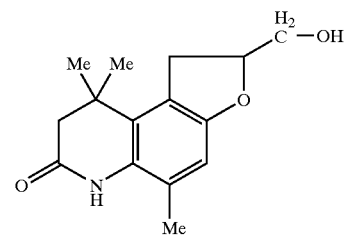

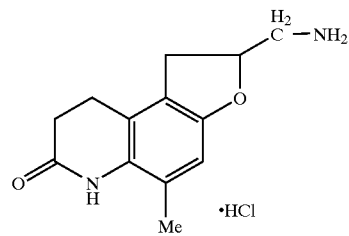

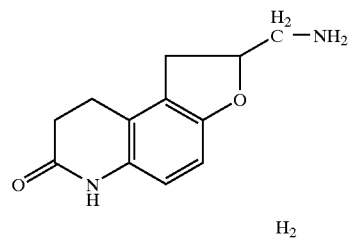

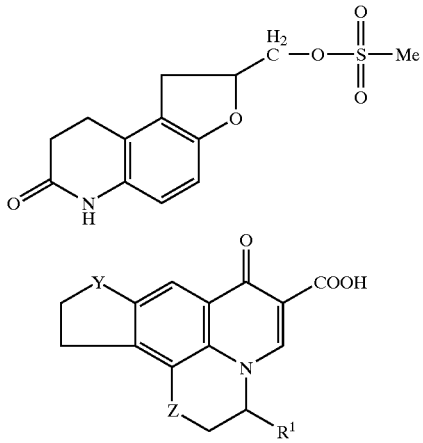

JP-A 54-163598 describes 2,3-dihydro or 2,3,10,11-tetrahydro-7-oxo-1H, 7H-furo or thieno[2,3-g]pyrid[3,2,1-i,j]quinoline-6-carboxylic acid derivatives or salts thereof which have antibacterial activity, as well as compounds:

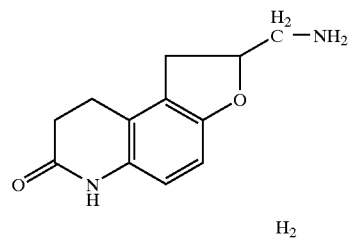

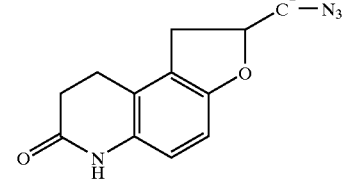

wherein R³ denotes a lower alkyl group, and other symbols are as defined above, as a synthetic intermediate therefor.

Lipid peroxidation inhibitory agents (antioxidants), which have lipid peroxidation inhibitory activity based on excellent antioxidant activity and are excellent in pharmacokinetics, can be expected to have excellent activity for preventing or treating central nervous diseases and disorders (for example, ischemic central nervous disorders (e.g., cerebral infarct, cerebral bleeding, cerebral edema etc.), central nervous system injury (for example, cranial trauma, head injury, spinal injury, whiplash injury etc.), neurodegenerative diseases (for example, Alzheimer's disease, Parkinson's disease, Huntington's chorea, amyotrophic lateral sclerosis etc.), vascular dementia (for example, multi-infarct dementia, Binswanger's disease etc.), manic-depressive psychosis, depressive disease, schizophrenia, chronic pain, trigeminal neuralgia, migraine etc.), circulatory diseases or disorders (for example, ischemic cardiac failure (for example, cardiac infarct, angina etc.), arterial sclerosis, arterial restenosis after PTCA (percutaneous transluminal coronary angioplasty), inferior urinary tract diseases or disorders (for example, dysuria, urinary incontinence) etc.), diabetic neurosis and the like. However, currently, since sufficiently satisfactory inhibitory agents have not been found, it has been desired to develop compounds having excellent lipid peroxidation inhibitory activity, which are sufficiently satisfactory medicaments.

DISCLOSURE OF THE INVENTION

The present inventors intensively studied compounds having excellent lipid peroxidation inhibitory activity. As a result, the present inventors synthesized for the first time compounds represented by the formula:

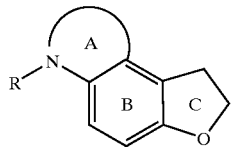

wherein A ring denotes a non-aromatic 5- to 7-membered nitrogen-containing heterocyclic ring which may be further substituted, B ring denotes a benzene ring which may be further substituted, C ring denotes a dihydrofuran ring which may be further substituted, R denotes hydrogen atom or an acyl group, provided that: (1) when A ring is a non-aromatic 5-membered nitrogen-containing heterocyclic ring substituted with a group represented by the formula —(CH$_2$)—N (R")—C(=O)—R' (wherein R' denotes an optionally substituted hydrocarbon group, an optionally substituted amino group or an optionally substituted heterocyclic group, R" denotes hydrogen atom or an optionally substituted hydrocarbon group, and m denotes an integer of 1 to 4), B ring denotes a benzene ring which is further substituted, (2) when A ring is a non-aromatic 6-membered nitrogen-containing heterocyclic ring substituted with oxo, B ring denotes a wholly substituted benzene ring, which has the chemical-structurally characteristics that nitrogen-containing non-aromatic heterocyclic ring is fused at the 4 and 5 positions of the dihydrobenzofuran ring, or salts thereof (hereinafter, sometimes, abbreviated as Compound (I)), and found that these novel compounds unexpectedly exhibit excellent lipid peroxidation inhibitory activity based on the special chemical structure. Further, the present inventors found that compounds including Compound (I), represented by the formula:

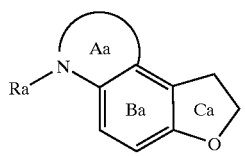

wherein Aa ring denotes a non-aromatic 5- to 7-nitrogen-containing heterocyclic ring which may be further substituted, Ba ring denotes a benzene ring which may be further substituted, Ca ring denotes a dihydrofuran ring which may be further substituted, and Ra denotes hydrogen atom or an acyl group or salts thereof (hereinafter, sometimes, abbreviated as Compound (I')) have excellent lipid peroxidation inhibitory activity and have excellent effects and natures as a medicine which can be used clinically. The present invention has been completed based on these findings.

That is, the present invention relates to:
(1) Compound (I),
(2) the compound described in the above (1), wherein A ring is a non-aromatic 5- to 7-membered nitrogen-containing heterocyclic ring which may be further substituted with an optionally substituted hydrocarbon group,
(3) the compound described in the above (1), wherein A ring is a non-aromatic 5- to 7-membered nitrogen-containing heterocyclic ring which may be further substituted with an optionally substituted lower alkyl group,
(4) the compound described in the above (1), wherein A ring is a non-aromatic 5- to 7-membered nitrogen-containing heterocyclic ring which may be further substituted with a lower alkyl group,
(5) the compound described in the above (1), wherein A ring is a non-aromatic 5-membered nitrogen-containing heterocyclic ring which may be further substituted with a lower alkyl group,
(6) the compound described in the above (1), wherein B ring is a wholly substituted benzene ring, (7) the compound described in the above (1) which is a compound represented by the formula:

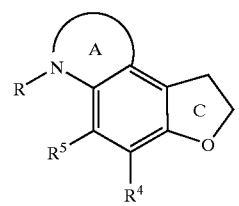

wherein $R^4$ and $R^5$ are the same or different and each denotes hydrogen atom, a halogen atom, hydroxy group, amino group, or an optionally substituted hydrocarbon group which may be via oxygen atom, nitrogen atom or sulfur atom, and other symbols are as defined in the above (1), provided that both $R^4$ and $R^5$ do not denote hydrogen atom at the same time, or a salt thereof,
(8) the compound described in the above (7), wherein $R^4$ and $R^5$ are the same or different and each is a lower alkyl group or a lower alkoxy group,
(9) the compound described in the above (7), wherein $R^4$ and $R^5$ are a lower alkyl group,
(10) the compound described in the above (1) which is a compound represented by the formula:

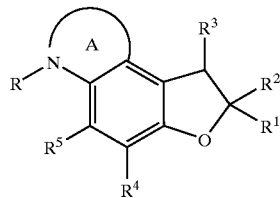

wherein $R^1$ and $R^2$ are the same or different and each denotes hydrogen atom, carboxyl group or an optionally substituted hydrocarbon group, $R^3$ denotes hydrogen atom, an optionally substituted hydrocarbon group or an optionally substituted amino group, and other symbols are as defined in the above (7), or a salt thereof

(11) the compound described in the above (10), wherein $R^1$ is a lower alkyl group, $R^2$ is a lower alkyl group which may be substituted with an optionally substituted cyclic amino, a halogen atom or a hydroxy, and $R^3$ is hydrogen atom or an optionally substituted phenyl group,

(12) the compound described in the above (10), wherein $R^1$ is a lower alkyl group, $R^2$ is a halogen atom, a hydroxy or a lower alkyl group which may be substituted with an optionally substituted cyclic amino group, a halogen atom or a hydroxy, $R^3$ is hydrogen atom or an optionally substituted phenyl group, $R^4$ and $R^5$ are a lower alkyl group, and A ring is a non-aromatic 5- to 7-membered nitrogen-containing heterocyclic ring which may be further substituted with a lower alkyl group,

(13) the compound described in the above (10), wherein $R^1$ is a lower alkyl group, $R^2$ is a lower alkyl group which may be substituted with an optionally substituted cyclic amino group, a halogen atom or a hydroxy, $R^3$ is hydrogen atom or an optionally substituted phenyl group, $R^4$ and $R^5$ are independently a lower alkyl group, and A ring is a non-aromatic 5-membered nitrogen-containing heterocyclic ring which may be further substituted with a lower alkyl group,

(14) the compound described in the above (1) which is 1,6,7,8-tetrahydro-2,2,4,5-tetramethyl-1-(4-methylphenyl)-2H-furo[3,2-e]indole or a salt thereof,

(15) the compound described in the above (1) which is 1,6,7,8-tetrahydro-2,4,5-trimethyl-2-[(4-phenylpiperidino)methyl]-2H-furo[3,2-e]indole or a salt thereof,

(16) the compound described in the above (1) which is 1,6,7,8-tetrahydro-2,4,5,7,7-pentamethyl-2-[(4-phenylpiperidino)methyl]-2H-furo[3,2-e]indole or a salt thereof,

(17) the compound described in the above (1) which is N-(diphenylmethyl)-1-[(1,6,7,8-tetrahydro-2,4,5,7,7-pentamethyl-2H-furo[3,2-e]indol-2-yl)methyl]-4-piperidineamine or a salt thereof,

(18) a prodrug of Compound (I),

(19) a process for preparing Compound (I) which comprises ring-closing a substituent X and hydroxy group on B ring of a compound represented by the formula:

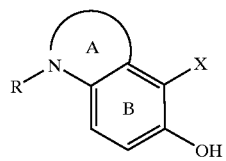

wherein X denotes an optionally substituted allyl group, and other symbols are as defined above, or a salt thereof,

(20) a pharmaceutical composition, which comprises Compound (I) or a prodrug thereof,

(21) the composition described in the above (20), which is for preventing or treating cerebrovascular impairment, cranial trauma or neurodegenerative disease,

(22) the composition described in the above (21), wherein the neurodegenerative disease is Parkinson's disease or Alzheimer's disease,

(23) an agent for preventing or treating dysuria or urinary incontinence which comprises Compound (I') or a prodrug thereof,

(24) an agent for preventing or treating restenosis after percutaneous tarnsluminal coronary angioplasty which comprises Compound (I') or a prodrug thereof,

(25) an agent for inhibiting lipid peroxidation, which comprises Compound (I') or a prodrug thereof,

(26) a method for preventing or treating cerebrovascular impairment, cranial trauma or neurodegenerative disease which comprises administering Compound (I) or a prodrug thereof to a mammal,

(27) a method for preventing or treating dysuria or incontinence of urine which comprises administering Compound (I') or a prodrug thereof to a mammal,

(28) a method for preventing or treating restenosis after percutaneous tarnsluminal coronary angioplasty which comprises administering Compound (I') or a prodrug thereof to a mammal,

(29) a method for inhibiting lipid peroxidation which comprises administering Compound (I') or a prodrug thereof to a mammal,

(30) use of Compound (I) or a prodrug thereof for manufacturing a medicament for preventing or treating cerebrovascular impairment, cranial trauma or neurodegenerative disease,

(31) use of Compound (I') or a prodrug thereof for manufacturing a medicament for preventing or treating dysuria or urinary incontinence,

(32) use of Compound (I') or a prodrug thereof for manufacturing a medicament for preventing or treating restenosis after percutaneous transluminal coronary angioplasty, and

(33) use of Compound (I') or a prodrug thereof for manufacturing a medicament for inhibiting lipid peroxidation.

Examples of the "hydrocarbon group" in the term "optionally substituted hydrocarbon group" as used herein include linear or cyclic hydrocarbon groups (such as alkyl, alkenyl, alkynyl, cycloalkyl, aryl, aralkyl etc.) and the like. Among them, the following linear or cyclic hydrocarbon groups having 1 to 16 carbon atoms are preferable:

(i) lower alkyl (for example, $C_{1-6}$ alkyl such as methyl, ethyl, propyl, isopropyl, butyl, isobutyl, sec-butyl, tert-butyl, pentyl, hexyl etc.), (ii) lower alkenyl (for example, $C_{2-6}$ alkenyl such as vinyl, allyl, isopropenyl, butenyl, isobutenyl, sec-butenyl etc.), (iii) lower alkynyl (for example, $C_{2-6}$ alkynyl such as ethynyl, 1-propynyl, propargyl, butynyl, 1-hexynyl etc.)

(iv) $C_{3-6}$ cycloalkyl (for example, cyclopropyl, cyclobutyl, cyclopentyl, cyclohexyl, cycloheptyl etc.), (v) $C_{6-14}$ aryl (for example, phenyl, 1-naphthyl, 2-naphthyl, biphenylyl, 2-anthryl etc., preferably phenyl etc.), (vi) $C_{7-16}$ aralkyl (for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl etc., preferably benzyl etc.).

Examples of a "substituent" which may be possessed by the "hydrocarbon group" include (1) a halogen atom (such as fluorine, chlorine, bromine, iodine etc.), (2) optionally halogenated lower alkyl, (3) lower alkenyl (for example, $C_{2-6}$ alkenyl such as vinyl, allyl, isopropenyl, butenyl, isobutenyl, sec-butenyl etc.), (4) lower alkynyl (for example, $C_{2-6}$ alkynyl such as ethynyl, 1-propynyl, propargyl, butynyl, 1-hexynyl etc.), (5) cycloalkyl (for example, $C_{3-6}$ cycloalkyl such as cyclopropyl, cyclobutyl, cyclopentyl, cyclohexyl etc.), (6) aryl (for example, $C_{6-10}$ aryl such as phenyl, 1-naphthyl, 2-naphthyl, biphenylyl, 2-anthryl etc.), (7) aralkyl (for example, $C_{7-11}$ aralkyl such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl etc.), (8) optionally halogenated lower alkoxy, (9) aryloxy (for example, $C_{6-10}$ aryloxy such as phenoxy etc.), (10) lower alkanoyl (for example, $C_{1-6}$ alkyl-carbonyl such as acetyl, propionyl, butyryl, isobutyryl etc.), (11) arylcarbonyl (for example, $C_{6-10}$ aryl-carbonyl such as benzoyl, naphthoyl etc.), (12) lower alkanoyloxy (for example, $C_{1-6}$ alkyl-carbonyloxy such as acetyloxy, propionyloxy, butyryloxy, isobutyloxy etc.), (13) arylcarbonyloxy (for example, $C_{6-10}$ arylcarbonyloxy such as benzoyloxy, naphthoyloxy etc.), (14) carboxyl, (15) lower alkoxy-carbonyl (for example, $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl etc.), (16) carbamoyl, thiocarbamoyl, (17) mono-lower alkylcarbamoyl (for example, mono-$C_{1-6}$ alkylcarbamoyl such as methylcarbamoyl, ethylcarbamoyl etc.), (18) di-lower alkylcarbamoyl (for example, di-$C_{1-6}$ alkylcarbamoyl such as dimethylcarbamoyl, diethylcarbamoyl etc.), (19) $C_{6-10}$ aryl-carbamoyl (for example, phenylcarbamoyl, naphthylcarbamoyl etc.), (20) amidino, (21) imino, (22) amino, (23) mono-lower alkylamino (for example, mono-$C_{1-6}$ alkylamino such as methylamino, ethylamino, propylamino, isopropylamino, butylamino etc.), (24) di-lower alkylamino (for example, di-$C_{1-6}$ alkylamino such as dimethylamino, diethylamino, ethylmethylamino, dipropylamino, diisopropylamino, dibutylamino etc., (25) alkylenedioxy (for example, $C_{1-3}$ alkylenedioxy such as methylenedioxy, ethylenedioxy etc.), (26) hydroxy, (27) nitro, (28) cyano, (29) mercapto, (30) sulfo, (31) sulfino, (32) phosphono, (33) sulfamoyl, (34) mono-lower alkylsulfamoyl (for example, mono-$C_{1-6}$ alkylsulfamoyl such as methylsulfamoyl, ethylsulfamoyl, propylsulfamoyl, isopropylsulfamoyl, butylsulfamoyl etc.), (35) di-lower alkylsulfamoyl (di-$C_{1-6}$ alkylsulfamoyl such as dimethylsulfamoyl, diethylsulfamoyl, dipropylsulfamoyl, dibutylsulfamoyl etc.), (36) optionally halogenated lower alkylthio, (37) arylthio (for example, $C_{6-10}$ arylthio such as phenylthio, naphthylthio etc.), (38) lower alkylsulfinyl (for example, $C_{1-6}$ alkylsulfinyl such as methylsulfinyl, ethylsulfinyl, propylsulfinyl, butylsulfinyl etc.), (39) arylsulfinyl (for example, $C_{6-10}$ arylsulfinyl such as phenylsulfinyl, naphthylsulfinyl etc.), (40) lower alkylsulfonyl (for example, $C_{1-6}$ alkylsulfonyl such as methylsulfonyl, ethylsulfonyl, propylsulfonyl, butylsulfonyl etc.), (41) arylsulfonyl (for example, $C_{6-10}$ arylsulfonyl such as phenylsulfonyl, naphthylsulfonyl etc.), (42) optionally substituted heterocyclic group, (43) oxo and the like. When the substituent is (25) alkylenedioxy, it is desirable that the substituent is taken together adjacent two carbon atoms to form a ring.

Examples of the "(2) optionally halogenated lower alkyl" as a substituent for the "hydrocarbon group" F include lower alkyl (for example, $C_{1-6}$ alkyl such as methyl, ethyl, propyl, isopropyl, butyl, isobutyl, sec-butyl, tert-butyl, pentyl, hexyl etc.) which may have 1 to 3 halogen atoms (for example, fluorine, chlorine, bromine, iodine etc.), and the like, more particularly, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like, preferably methyl and the like.

Examples of the "(8) optionally halogenated lower alkoxy" as a substituent for the "hydrocarbon group" include lower alkoxy (for example, $C_{1-6}$ alkoxy such as methoxy, ethoxy, propoxy, isopropoxy, butoxy, isobutoxy, sec-butoxy, tert-butoxy etc.) which may have 1 to 3 halogen atoms (for example, fluorine, chlorine, bromine, iodine etc.), and the like, more particularly, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

Examples of the "(36) optionally halogenated lower alkylthio" as a substituent for the "hydrocarbon group" include lower alkylthio (for example, $C_{1-6}$ alkylthio such as methylthio, ethylthio, propylthio, isopropylthio, butylthio, sec-butylthio, tert-butylthio etc.) which may have 1 to 3 halogen atoms (for example, fluorine, chlorine, bromine, iodine etc.), and the like, more particularly, methylthio, difluoromethylthio, trifluoromethylthio, ethylthio, propylthio, isopropylthio, butylthio, 4,4,4-trifluorobutylthio, pentylthio, hexylthio and the like.

Examples of the "(42) optionally substituted heterocyclic group" as a substituent for the "hydrocarbon group" include the same groups as the term "optionally substituted heterocyclic group" as used herein.

Examples of the "heterocyclic group" in the term "optionally substituted heterocyclic group" as used herein include aromatic heterocyclic group, saturated or unsaturated non-aromatic heterocyclic group or the like which contains at least 1 (preferably 1 to 4, more preferably 1 or 2) of 1 to 3 kinds (preferably 1 or 2 kinds) of heteroatoms selected from oxygen atom, sulfur atom and nitrogen atom as ring-constituting atoms (ring atoms).

Examples of the "aromatic heterocyclic group" include 5- or 6-membered aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, as well as 8- to 12-membered aromatic fused heterocyclic groups (preferably, heterocyclic rings wherein the aforementioned 5- or 6-membered aromatic monocyclic heterocyclic group is fused with a benzene ring, or heterocyclic rings wherein the same or different two heterocyclic rings of the aforementioned 5- or 6-membered aromatic monocyclic heterocyclic group are fused) such as benzofuranyl, isobenzofuranyl, benzothienyl, indolyl, isoindolyl, 1H-indazolyl, benzindazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, 1,2,4,5-tetrahydro-3H-3-benzazepine-3-yl and the like.

Examples of the "non-aromatic heterocyclic group" include 3- to 8-membered (preferably, 5- or 6-membered) saturated or unsaturated (preferably saturated) non-aromatic heterocyclic group and the like such as oxiranyl, azetidinyl, oxetanyl, thietanyl, pyrrolidinyl, tetrahydrofuryl, thiolanyl, piperidinyl, tetrahydropyranyl, morpholinyl, thiomorpholinyl, piperazinyl and the like.

Examples of a "substituent" which may be possessed by the "heterocyclic group" include (1) an optionally substituted alkyl group, (2) an optionally substituted amino group, (3) an optionally substituted aryl group, (4) an optionally substituted cycloalkenyl group, (5) an optionally substituted cycloalkyl group, (6) an optionally substituted alkenyl group, (7) an optionally substituted alkynyl group, (8) an optionally substituted amidino group, (9) an optionally substituted hydroxy group, (10) an optionally substituted thiol group, (11) an optionally esterified carboxyl group, (12) an optionally substituted carbamoyl group, (13) an optionally substituted thiocarbamoyl group, (14) an acyl group, (15) a halogen atom (for example, fluorine, chlorine, bromine, iodine etc., preferably chlorine, bromine etc.), (16) cyano group, (17) nitro group and the like. The heterocyclic group may be substituted with these arbitrary substituents at 1 to 5 (preferably, 1 to 3) replaceable positions.

Examples of the "(1) alkyl group" as a substituent for the "heterocyclic group" include $C_{1-6}$ alkyls such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl and the like. Examples of a substituent for the "(1) alkyl group" include aralkyloxy (for example, $C_{7-16}$ aralkyloxy such as benzyloxy etc.) which may be substituted with a substituent selected from lower alkoxy ($C_{1-6}$ alkoxy such as methoxy, ethoxy, propoxy etc.), halogen (for example, fluorine, chlorine, bromine, iodine etc.), lower alkyl (for example, $C_{1-6}$ alkyl such as methyl, ethyl, propyl etc.), amino, hydroxy, cyano, amidino and aryl (for example, $C_{6-16}$ aryl such as phenyl etc.), and the like. The heterocyclic ring may be substituted with these arbitrary substituents at 1 or 2 replaceable positions.

Examples of the "(3) aryl group" as a substituent for the "heterocyclic group" include $C_{6-14}$ aryl group such as phenyl, 1-naphthyl, 2-naphthyl, biphenylyl, 2-anthryl and the like. Examples of a substituent for the "(3) aryl group" include the same number and the same substituents as those for the "(1) alkyl group".

Examples of the "(4) cycloalkenyl group" as a substituent for the "heterocyclic group" include $C_{3-6}$ cycloalkenyl group such as cyclopropenyl, cyclobutenyl, cyclopentenyl, cyclohexenyl and the like. Examples of a substituent for the "(4) cycloalkenyl group" include the same number and the same substituents as those for the "(1) alkyl group".

Examples of the "(5) cycloalkyl group" as a substituent for the "heterocyclic group" include $C_{3-7}$ cycloalkyl group such as cyclopropyl, cyclobutyl, cyclopentyl, cyclohexyl, cycloheptyl and the like. Examples of a substituent for the "(2) cycloalkyl group" include the same number and the same substituents as those for the "(1) alkyl group".

Examples of the "(6) alkenyl group" as a substituent for the "heterocyclic group" include $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like. Examples of a substituent for the "(6) alkenyl group" include the same number and the same substituents as those for the "(1) alkyl group".

Examples of the "(7) alkynyl group" as a substituent for the "heterocyclic group" include $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Examples of a substituent for the "(7) alkynyl group" include the same number and the same substituents as those for the "(1) alkyl group".

Examples of a substituent in the "(2) amino group", the "(8) amidino group", the "(9) hydroxy group" and the "(10) thiol group" as a substituent include lower alkyl group (for example, $C_{1-6}$ alkyl group such as methyl, ethyl, propyl, isopropyl, butyl, isobutyl, t-butyl, pentyl, hexyl etc.), acyl groups ($C_{1-6}$ alkanoyl (for example, formyl, acetyl, propionyl, pivaloyl etc.), benzoyl etc), optionally halogenated $C_{1-6}$ alkoxy-carbonyl (for example, trifluoromethoxycarbonyl, 2,2,2-trifluoroethoxycarbonyl, trichloromethoxycarbonyl, 2,2,2-trichloroethoxycarbonyl etc.) and the like. These substituents may be further substituted with an aryl group (for example, $C_{6-10}$ aryl group such as phenyl, 1-naphthyl, 2-naphthyl etc.) and a heterocyclic group. As the "heterocyclic group", the same "heterocyclic group" as that for the "optionally substituted heterocyclic group" is used. In the "(2) amino group" as a substituent, two substituents are taken together with nitrogen atom to form a cyclic amino group in some cases. Examples of the cyclic group in such the case include 3- to 8-membered (preferably, 5- or 6-membered) cyclic amino such as 1-azetidinyl, 1-pyrrolidinyl, piperidino, morpholino, 1-piperazinyl, and 1-piperazinyl which may have a lower alkyl group (for example, $C_{1-6}$ alkyl group such as methyl, ethyl, propyl, isopropyl, butyl, t-butyl, pentyl, hexyl etc.), an aralkyl group (for example, $C_{7-10}$ aralkyl group such as benzyl, phenethyl etc.), an aryl group (for example, $C_{6-10}$ aryl group such as phenyl, 1-naphthyl, 2-naphthyl etc.) and the like at a 4-position.

Examples of the "(11) optionally esterified carboxyl group" include a lower alkoxy-carbonyl group, aryloxycarbonyl group, aralkyloxycarbonyl group and the like in addition to free carboxyl group.

Examples of the "lower alkoxy-carbonyl group" include $C_{1-6}$ alkoxy-carbonyl group such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and the like.

Examples of the "aryloxycarbonyl group" include $C_{7-12}$ aryloxycarbonyl group such as phenoxycarbonyl, 1-naphthoxycarbonyl, 2-naphthoxycarbonyl and the like.

Examples of the "aralkyloxycarbonyl group" include $C_{7-1}$ aralkyloxy-carbonyl group such as benzyloxycarbonyl, phenethyloxycarbonyl and the like.

Examples of the "(12) optionally substituted carbamoyl group" include N-monosubstituted carbamoyl group and N,N-disubstituted carbamoyl group in addition to unsubstituted carbamoyl.

The "N-monosubstituted carbamoyl group" means a carbamoyl group having one substituent on nitrogen atom. Examples of the substituent include lower alkyl group (for example, $C_{1-6}$ alkyl group such as methyl, ethyl, propyl, isopropyl, butyl, isobutyl, t-butyl, pentyl, hexyl etc.) and the like.

The "N,N-disubstituted carbamoyl" means a carbamoyl group having two substituents on nitrogen atom.

The "N,N-disubstituted carbamoyl group" means a carbamoyl group having two substituents on nitrogen atom. Examples of one of the substituents include the same substituents as those for the above "N-monosubstituted carbamoyl group" and examples of the other include a lower alkyl group (for example, $C_{1-6}$ alkyl group such as methyl, ethyl, propyl, isopropyl, butyl, t-butyl, pentyl, hexyl etc.), $C_{3-6}$ cycloalkyl group (for example, cyclopropyl, cyclobutyl, cyclopentyl, cyclohexyl etc.), $C_{7-10}$ aralkyl group (for example, benzyl, phenethyl etc., preferably phenyl-$C_{1-6}$ alkyl group etc.) and the like. Alternatively, two substituents may be taken together with nitrogen atom to form a cyclic amino group and examples of a cyclic aminocarbamoyl group in such a case include 3- to 8-membered (preferably 5- or 6-membered) cyclic amino-carbonyl 1-azetidinylcarbonyl, 1-pyrrolidinylcarbonyl, piperidinocarbonyl, morpholinocarbonyl, 1-piperazinylcarbonyl, and 1-piperazinylcarbonyl which may have a lower alkyl group (for example, $C_{1-6}$ alkyl group such as methyl, ethyl, propyl, isopropyl, butyl, t-butyl, pentyl, hexyl etc.), an aralkyl group (for example, $C_{7-10}$ aralkyl group such as benzyl, phenethyl etc.), an aryl group (for example, $C_{6-10}$ aryl group such as phenyl, 1-naphthyl, 2-naphthyl etc.) and the like.

Examples of a substituent for the "(13) thiocarbamoyl group" as a substituent for the "heterocyclic group" include the same substituents as those for the above "(12) carbamoyl group".

Examples of the "(17) acyl group" as a substituent for the "heterocyclic group" include the same acyl groups as those used herein.

The "heterocyclic group" may have 1 to 4, preferably 1 or 2 aforementioned substituents at a replaceable position on the ring. When the number of substituents are two or more, they may be the same or different.

Examples of the "(2) optionally substituted amino group" as a substituent for the "heterocyclic group" include the same groups as the term "optionally substituted amino group" as used herein.

Examples of the term "optionally substituted amino group" as used herein include amino group optionally having 1 or 2 substituents, a cyclic amino group optionally having a substituent and the like.

Examples of the "amino group optionally having 1 or 2 substituents" include mono-lower alkylamino (for example, mono-$C_{1-6}$ alkyl amino such as methylamino, ethylamino, propylamino, isopropylamino, butylamino etc.), di-lower alkylamino (for example di-$C_{1-6}$ alkylamino such as dimethylamino, diethylamino, ethylmethylamino, dipropylamino, diisopropylamino, dibutylamino etc.) and the like.

Examples of a "cyclic amino group" in the "optionally substituted cyclic amino group" include 3- to 6-membered cyclic amino groups optionally containing 1 to 3 heteroatoms selected from oxygen atom, sulfur atom and nitrogen atom in addition to carbon atoms and 1 nitrogen atom (for example, 3- to 6-membered cyclic amino such as aziridinyl, azetidinyl, pyrrolidinyl, pyrrolinyl, pyrrolyl, imidazolyl, pyrazolyl, imidazolidinyl, piperidino, morpholino, thiomorpholino, dihydropyridyl, pyridyl, N-methylpiperazinyl, N-ethylpiperazinyl etc.).

Examples of a substituent for the "amino group" include an optionally substituted hydrocarbon group and the like. As the "optionally substituted hydrocarbon group", the same group as the aforementioned "optionally substituted hydrocarbon group" is used. When the number of the substituents are 2, they may be the same or different.

Examples of a "substituent" for the "cyclic amino group" include an optionally substituted hydrocarbon group and the like. As the "optionally substituted hydrocarbon group", the same group as the aforementioned "optionally substituted hydrocarbon group" is used. The "cyclic amino group" may have 1 to 5, preferably 1 to 3 aforementioned substituents at a replaceable position on the cyclic amino group. When the number of substituent is two or more, they may be the same or different.

Examples of the term "acyl group" as used herein include acyl derived from carboxylic acid or sulfonic acid, and the like.

More specifically, examples thereof include formyl, lower alkylcarbonyl (for example, $C_{1-6}$ alkyl-carbonyl such as acetyl, propionyl, butyryl, isobutyryl etc.), arylcarbonyl (for example, $C_{6-10}$ aryl-carbonyl such as benzoyl, naphthoyl etc.), aralkylcarbonyl "for example, $C_{6-10}$ aryl-$C_{1-6}$ alkyl-carbonyl such as benzylcarbonyl, phenethylcarbonyl, naphthylmethylcarbonyl etc.", lower alkoxycarbonyl (for example, $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl etc.), aralkyloxycarbonyl (for example, $C_{6-10}$ aryl-$C_{1-6}$ alkoxy-carbonyl such as benzyloxycarbonyl etc.), lower alkylsulfonyl (for example, $C_{1-6}$ alkylsulfonyl such as methylsulfonyl, ethylsulfonyl, propylsulfonyl etc.), $C_{6-10}$ arylsulfonyl optionally having lower ($C_{16}$) alkyl (for example, phenylsulfonyl, naphthylsulfonyl, tosyl etc.), aralkylsulfonyl (for example, $C_{6-10}$ aryl-$C_{1-16}$ alkylsulfonyl such as benzylsulfonyl, phenethylsulfonyl, naphthylmethylsulfonyl etc.) and the like. These groups may have further 1 to 3 halogen atoms (for example, fluorine, chlorine, bromine, iodine etc.).

In the above formula, A ring denotes a non-aromatic 5- to 7-membered nitrogen-containing heterocyclic ring which may have a further substituent.

Examples of the (non-aromatic 5- to 7-membered nitrogen-containing heterocyclic ring) represented by A ring include a non-aromatic 5- to 7-membered (preferably 5- or 6-membered) nitrogen-containing heterocyclic ring which contains at least 1 nitrogen atom in addition to carbon atoms and embodiments thereof include 2,3-dihydro-1H-pyrrole, 1,2-dihydropyridine, 1,2,3,4-tetrahydropyridine, 2,3,4,5-tetrahydro-1H-azepine, 2,3-dihydro-1H-azepine and the like.

Examples of the substituent which may be further possessed by the "non-aromatic 5- to 7-membered nitrogen-containing heterocyclic ring" include an optionally substituted hydrocarbon group, an optionally halogenated lower alkoxy group, an optionally halogenated lower alkylthio group, a halogen atom (for example, fluorine, chlorine, bromine, iodine etc.), an aryloxy group ($C_{6-10}$ aryloxy such as phenoxy etc.), lower alkanoyl ($C_{1-6}$ alkyl-carbonyl such as acetyl, propionyl, butyryl, isobutyryl etc.), an arylcarbonyl group ($C_{6-10}$ aryl-carbonyl such as benzoyl, naphthoyl etc.), a lower alkanoyloxy group (for example, $C_{1-6}$ alkyl-carbonyloxy such as acetyloxy, propionyloxy, butyryloxy, isobutyryloxy etc.), an arylcarbonyloxy group (for example, $C_{6-10}$ aryl-carbonyloxy such as benzoyloxy, naphthoyloxy etc.), carboxyl group, a lower alkoxy-carbonyl group, for example, $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl etc.), a carbamoyl group, a thiocarbamoyl group, a mono-lower alkylcarbamoyl group (for example, mono-$C_{1-6}$ alkyl-carbamoyl such as methylcarbamoyl, ethylcarbamoyl etc.), a di-lower alkylcarbamoyl group (for example, di-$C_{1-6}$ alkyl-carbamoyl such as dimethylcarbamoyl, diethylcarbamoyl etc.), a $C_{6-10}$ aryl-carbamoyl group (for example, phenylcarbamoyl, naphthyl carbamoyl etc.), an amidino group, an imino group, amino group, a mono-lower alkylamino group (for example, mono-$C_{1-6}$ alkylamino such as methylamino, ethylamino, propylamino, isopropylamino, butylamino etc.), a di-lower alkylamino group (for example, di-$C_{1-6}$ alkylamino such as dimethylamino, diethylamino, ethylmethylamino, dipropylamino, diisopropylamino, dibutylamino etc.), a 3- to 6-membered cyclic amino group optionally containing 1 to 3 heteroatoms selected from oxygen atom, sulfur atom, nitrogen atom in addition to carbon atoms and 1 nitrogen atom (for example, 3- to 6-membered cyclic amino such as aziridinyl, azetidinyl, pyrrolidinyl, pyrrolinyl, pyrrolyl, imidazolyl, pyrazolyl, imidazolidinyl, piperidino, morpholino, thiomorpholino, dihydropyridyl, pyridyl, N-methylpiperazinyl, N-ethylpiperazinyl etc.), an alkylenedioxy group (for example, $C_{1-3}$ alkylenedioxy such as methylenedioxy, ethylenedioxy etc.), hydroxy group, nitro group, cyano group, mercapto group, sulfo group, sulfino group, phosphono group, sulfamoyl group, a mono-lower alkylsulfamoyl group (for example, mono-$C_{1-6}$ alkylsulfamoyl such as sulfamoyl, ethylsulfamoyl, propylsulfamoyl, isopropylsulfamoyl, butylsulfamoyl etc.), a di-lower alkylsulfamoyl group (for example, di-$C_{1-6}$ alkylsulfamoyl such as dimethylsulfamoyl, diethylsulfamoyl, dipropylsulfamoyl, dibutylsulfamoyl etc.), an arylthio group (for example, $C_{6-10}$ arylthio such as phenylthio, naphthylthio etc.), a lower alkylsulfinyl group (for example, $C_{1-6}$ alkylsulfinyl such as methylsulfinyl, ethylsulfinyl, propylsulfinyl, butylsulfinyl etc.), an arylsulfinyl group (for example, $C_{6-10}$ arylsulfinyl such as phenylsulfinyl, naphthylsulfinyl etc.), a lower alkylsulfonyl group (for example, $C_{1-6}$ alkylsulfonyl such as methylsulfonyl, ethylsulfonyl, propylsulfonyl, butylsulfonyl etc.), an arylsulfonyl group (for example, $C_{6-10}$ arylsulfonyl such as phenylsulfonyl, naphthylsulfonyl etc.) and the like. When the substituent is an alkylenedioxy group, it is desirable that the group is taken together with adjacent two carbon atoms to form a ring.

The "non-aromatic 5- to 7-membered nitrogen-containing heterocyclic ring" represented by A ring may have 1 to 4, preferably 1 or 2 aforementioned substituents at a replaceable position on the ring. When the number of substituents is two or more, they may be the same or different.

As the A ring, non-aromatic 5- to 7-membered nitrogen-containing heterocyclic rings which may be further substituted with an optionally substituted hydrocarbon group (preferably, an optionally substituted lower ($C_{1-6}$) alkyl group) are preferable, non-aromatic 5 to 7-membered nitrogen-containing heterocyclic rings which may be further substituted with a lower alkyl group (preferably, $C_{1-6}$ alkyl group such as methyl etc.) are more preferable, and non-aromatic 5-membered nitrogen-containing heterocyclic rings are particularly preferable.

In the aforementioned formula, B ring denotes a benzene ring which has a further substituent.

Examples of the substituent which may be further possessed by the "benzene ring" include a halogen atom (for example, fluorine, chlorine, bromine, iodine etc.), hydroxy group, amino group, and a hydrocarbon group which may be via oxygen atom, nitrogen atom or sulfur atom and which may have substituent(s), and the like.

Examples of the "hydrocarbon group which may be via oxygen atom, nitrogen atom or sulfur atom and which may have substituent(s)" as a substituent for the "benzene ring" include an optionally substituted hydrocarbon group, an optionally substituted alkoxy group, an optionally substituted aryloxy group, a substituted amino group, an optionally substituted alkylthio group, an optionally substituted arylthio group and the like.

Examples of the "optionally substituted hydrocarbon group" as a substituent for the "benzene ring" include the same groups as the aforementioned "optionally substituted hydrocarbon group".

Examples of the "alkoxy group" in the "optionally substituted alkoxy group" as a substituent for the "benzene ring" include lower ($C_{1-6}$) alkoxy such as methoxy, ethoxy, propoxy, isopropoxy, butoxy, isobutoxy, sec-butoxy, tert-butoxy and the like. Examples of a substituent which may be possessed by the "alkoxy group" include the same substituent as the "substituent" for the aforementioned "optionally substituted hydrocarbon group". The "alkoxy group" may have 1 to 5, particularly 1 to 3 aforementioned substituents at a replaceable position. When the number of substituents is two or more, they may be the same or different.

Examples of the "aryloxy group" in the "optionally substituted aryloxy group" as a substituent for the "benzene ring" include $C_{6-10}$ aryloxy such as phenoxy and the like. Examples of a substituent which may be possessed by the "aryloxy group" include the same substituent as the "substituent" for the aforementioned "optionally substituted hydrocarbon group". The "aryloxy group" may have 1 to 5, preferably 1 to 3 aforementioned substituents at a replaceable position. When the number of substituents is two or more, they may be the same or different.

Examples of the "substituted amino group" as a substituent for the "benzene ring" include amino group having 1 or 2 substituents, an optionally substituted cyclic amino group and the like. Examples of the "amino group having 1 or 2 substituents" and the "optionally substituted cyclic amino group" include the same groups as the "amino group having 1 or 2 substituents" and the "optionally substituted cyclic amino group" in the "(2) optionally substituted amino group" as a substituent for the aforementioned "optionally substituted heterocyclic group".

Examples of the "alkylthio group" in the "optionally substituted alkylthio group" as a substituent for the "benzene ring" include $C_{1-6}$ alkylthio such as methylthio, ethylthio, propylthio, isopropylthio, butylthio, sec-butylthio, tert-butylthio and the like. Examples of a substituent which may be possessed by the "alkylthio group" include the same substituent as "substituent" for the aforementioned "optionally substituted hydrocarbon group". The "alkylthio group" may have 1 to 5, preferably 1 to 3 aforementioned substituents at a replaceable position. When the number of substituents is two or more, they may be the same or different.

Examples of the "arylthio group" in the "optionally substituted arylthio group" as a substituent for the "benzene ring" include $C_{6-10}$ arylthio such as phenylthio, naphthylthio and the like. Examples of the "substituent" which may be possessed by "arylthio group" include the same substituent as the "substituent" for the aforementioned "optionally substituted hydrocarbon group". The "arylthio group" may have 1 to 5, preferably 1 to 3 aforementioned substituents at a replaceable position. When the number of substituents is two or more, they may be the same or different. The "benzene ring" represented by B ring may have 1 or 2 aforementioned substituents at a replaceable position on the ring. When the number of substituents is two or more, they may be the same or different.

As the B ring, a wholly substituted benzene ring is preferable.

As a substituent for such the B ring, a halogen atom or an electron donor group (hydroxy group, amino group, or a hydrocarbon group which may be via oxygen atom, nitrogen atom or sulfur atom and which may have substituent(s)) is preferable from a viewpoint of the activity and effect (lipid peroxidation inhibitory activity).

In the aforementioned formula, C ring denotes a dihydrofuran ring which may have a further substituent.

Examples of the substituent which may be further possessed by the "dihydrofuran ring) represented by the C ring include carboxyl group, an optionally substituted hydrocarbon group, an optionally substituted amino group and the like.

Examples of the "optionally substituted hydrocarbon group" as a substituent for the "dihydrofuran ring" include the same group as the aforementioned "optionally substituted hydrocarbon group". A "optionally substituted cyclic amino group" may be preferably used as a substituent for the "hydrocarbon group".

Examples of the "optionally substituted cyclic amino group" include groups represented by the formula:

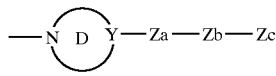

wherein Zc denotes hydrogen atom, an optionally substituted alkyl group or an optionally substituted aromatic group,
- D ring may have substituent(s) and represents a 5 to 8-membered nitrogen-containing heterocyclic ring optionally fused with a benzene ring,
- Y denotes a carbon atom or nitrogen atom,
- Za denotes a bond, oxygen atom, sulfur atom, a group represented by the formula $NR^9$ (wherein $R^9$ denotes hydrogen atom, an optionally substituted hydrocarbon group or an acyl group), and
- Zb denotes a bond or a divalent aliphatic hydrocarbon group which may have substituent(s) and which may be via oxygen atom, nitrogen atom or sulfur atom and the like.

Examples of an "alkyl group" in the "optionally substituted alkyl group" represented by Zc include lower alkyl (for example, $C_{1-6}$ alkyl such as methyl, ethyl, propyl, isopropyl, butyl, isobutyl, sec-butyl, tert-butyl, pentyl, hexyl etc.) and the like. Examples of a "substituent" which may be possessed by the "alkyl group" include the same substituent as the "substituent" which may be possessed by the "hydrocarbon group" in the aforementioned "optionally substituted hydrocarbon group".

Examples of the "aromatic group" in the "optionally substituted aromatic group" represented by Zc include an aromatic hydrocarbon group, an aromatic heterocyclic group and the like.

Examples of the "aromatic hydrocarbon group" include monocyclic or fused polycyclic aromatic hydrocarbon groups having 6 to 14 carbon atoms. Embodiments thereof include $C_{6-14}$ aryl such as phenyl, 1-naphthyl, 2-naphthyl, anthryl and the like. Among them, $C_{6-10}$ aryl such as aryl, 1-naphthyl, 2-naphthyl and the like is preferable. Particularly preferable is phenyl, phenyl.

Examples of the "aromatic heterocyclic group" include 5- to 10-membered monocyclic or its fused aromatic heterocyclic groups containing 1 or more (for example, 1 to 4) heteroatoms selected from nitrogen atom, sulfur atom and oxygen atom in addition to carbon atoms. More particularly, embodiments thereof include aromatic heterocyclic rings such as thiophene, benzothiophene, benzofuran, benzimidazole, benzoxazole, benzothiazole, benzisothiazole, naphtho[2,3-b]thiophene, furan, pyrrole, imidazole, pyrazole, pyridine, pyrazine, pyrimidine, pyridazine, indole, isoindole, 1H-indazole, isoquinoline, quinoline, carbazole, isothiazole, isoxazole and the like, or monovalent groups obtained by removing arbitrary hydrogen atoms from a ring formed by fusion of those rings (preferably, 5- or 6-membered monocycle) with 1 or plural (preferably, 1 or 2, more preferably 1) aromatic rings (for example, benzene ring, pyridine ring etc.). Preferable examples of the "aromatic heterocyclic group" include 2-pyridyl, 3-pyridyl, 4-pyridyl, 2-quinolyl, 3-quinolyl, 4-quinolyl, 5-quinolyl, 8-quinolyl, 8-isoquinolyl, 3-isoquinolyl, 4-isoquinolyl, 5-isoquinolyl, 1-indolyl, 2-indolyl, 3-indolyl, 2-benzothiazolyl, 2-benzothienyl, benzofuranyl, 2-thienyl, 3-thienyl, 2-benzoxazolyl, 2-benzimidazolyl, 2-pyridothiazolyl and the like. More preferable are 2-pyridyl, 3-pyridyl, 3-pyridyl, 2-quinolyl, 3-quinolyl, 4-quinolyl, 2-indolyl, 3-indolyl, and the like.

Examples of the "substituent" in the "optionally substituted aromatic group" represented by Zc include a halogen atom (for example, fluorine, chlorine, bromine, iodine etc.), $C_{1-3}$ alkylenedioxy (for example, methylenedioxy, ethylenedioxy etc.), nitro, cyano, optionally halogenated $C_{1-6}$ alkyl, $C_{3-6}$ cycloalkyl (for example, cyclopropyl, cyclobutyl, cyclopentyl, cyclohexyl etc.), optionally halogenated $C_{1-6}$ alkoxy, optionally halogenated $C_{1-6}$ alkylthio, hydroxy, amino, mono-$C_{1-6}$ alkylamino (for example, methylamino, ethylamino, propylamino, isopropylamino, butylamino etc.), di-$C_{1-6}$ alkylamino (for example, dimethylamino, diethylamino, ethylmethylamino, dipropylamino, dibutylamino etc.), $C_{1-6}$ alkyl-carbonyl (for example, acetyl, propionyl etc.), carboxyl, $C_{1-6}$ alkoxy-carbonyl (for example, methoxycarbonyl, ethoxycarbonyl, propoxycarbonyl, butoxycarbonyl etc.), carbamoyl, mono-$C_{1-6}$ alkylcarbamoyl (for example, methylcarbamoyl, ethylcarbamoyl etc.), di-$C_{1-6}$ alkylcarbamoyl (for example, dimethylcarbamoyl, diethylcarbamoyl etc.), $C_{6-10}$ aryl-carbamoyl (for example, phenylcarbamoyl, naphthylcarbamoyl etc.), sulfo, $C_{1-6}$ alkylsulfonyl (for example, methylsulfonyl, ethylsulfonyl etc.), $C_{6-10}$ aryl (for example, phenyl, naphthyl etc.), $C_{6-10}$ aryloxy (for example, phenyloxy, naphthyloxy etc.) and the like. When the substituent is $C_{1-3}$ alkylenedioxy, it is preferable that the substituent is taken together with adjacent two carbon atoms to form a ring.

Examples of the "optionally halogenated $C_{1-6}$ alkyl) include $C_{1-6}$ alkyl (for example, methyl, ethyl, propyl, isopropyl, butyl, isobutyl, sec-butyl, tert-butyl, pentyl, hexyl etc.) and the like optionally having 1 to 3 halogen atomes (for example, fluorine, chlorine, bromine, iodine etc.), more particularly, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl and the like.

Examples of the "optionally halogenated $C_{1-6}$ alkoxy" include $C_{1-6}$ alkoxy optionally having 1 to 3 halogen atoms (for example, fluorine, chlorine, bromine, iodine etc.), more particularly, methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy and the like.

Examples of the "optionally halogenated $C_{1-6}$ alkylthio" include $C_{1-6}$ alkylthio (for example, methylthio, ethylthio, propylthio, isopropylthio, butylthio, sec-butylthio, tert-butylthio etc.) and the like optionally having 1 to 3 halogen atoms (for example, fluorine, chlorine, bromine, iodine etc.), more particularly, methylthio, difluoromethylthio, trifluoromethylthio, ethylthio, propylthio, isopropylthio, butylthio, 4,4,4-trifluorobutylthio, pentylthio, hexylthio and the like.

The "aromatic group" in the "optionally substituted aromatic group" may have 1 to 5, preferably 1 to 3 aforementioned substituents at a replaceable position on its ring. When the number of substituents is two or more, they may be the same or different.

Zc is preferably an optionally substituted aromatic group, more preferably each optionally substituted, $C_{6-14}$ aryl (preferably phenyl), 2-pyridyl, 3-pyridyl, 4-pyridyl, 2-indolyl, 3-indolyl or benzimidazole, particularly preferably optionally substituted $C_{6-10}$ aryl. Preferable examples of the "substituent" are a halogen atom, $C_{1-6}$ alkoxy and $C_{1-6}$ alkyl. Zc is more preferably $C_{6-14}$ aryl (preferably phenyl) which may have 1 to 3 substituents selected from a halogen atom, $C_{1-6}$ alkoxy and $C_{1-6}$ alkyl. Further, it is also preferable that Zc is $C_{1-6}$ alkyl which may be substituted with 1 or 2 $C_{6-14}$ aryl.

Examples of the "5- to 8-membered nitrogen-containing heterocyclic ring" in the "5- to 8-membered nitrogen-containing heterocyclic ring which may have substituent(s) and which may be fused with a benzene ring" include 5- to 8-membered saturated or unsaturated heterocyclic rings containing at least 1 nitrogen atom in addition to carbon atoms. Embodiments thereof include piperidine, piperazine, 1,2,5,6-tetrahydropyridine, pyrrolidine, 1H-azepine, 1H-2,3-dihydroazepine, 1H-2,3,4,5-tetrahydroazepine, 1H-2,3,6,7-tetrahydroazepine, 1H-2,3,4,5,6,7-hexahydroazepine, 1H-1,4-diazepine, 1H-2,3-dihydro-1,4-diazepine, 1H-2,3,4,5-tetrahydro-1,4-diazepine, 1H-2,3,6,7-tetrahydro-1,4-diazepine, 1H-2,3,4,5,6,7-hexahydro-1,4-diazepine, 1,2-dihydroazepine, 2,3,4,5-tetrahydroazocine, 1,2,3,4,5,6-hexahydroazocine, 1,2,3,4,5,6,7,8-octahydroazocine, 1,2-dihydro-1,5-diazocine, 1,2,3,4,5,6-hexahydro-1,5-diazocine, 1,2,3,4,5,6,7,8-octahydro-1,5-diazocine and the like. Among them, preferable is a 6-membered nitrogen-containing heterocyclic ring. More preferable are piperidine, piperazine and the like.

As a "substituent" which may be possessed by the "5 to 8-membered nitrogen-containing heterocyclic ring", 1 to 3 substituents similar to those which may be possessed by the "optionally substituted aromatic group" represented by Zc are used. When the number of substituents is two or more, they may be the same or different.

D ring is preferably a 6- or 7-membered nitrogen-containing heterocyclic ring which may have substituent(s) and which may be fused with a benzene ring, more preferably, 1,2,4,5-tetrahydro-3H-benzazepine, piperidine or piperazine.

When Y denotes a carbon atom, an example thereof is a group represented by the formula: $>C(R^{10})$—. In the formula, examples of $R^{10}$ include hydrogen atom, a halogen atom (for example, fluorine, chlorine, bromine, iodine etc.), nitro, cyano, optionally halogenated $C_{1-6}$ alkyl, $C_{3-6}$ cycloalkyl (for example, cyclopropyl, cyclobutyl, cyclopentyl, cyclohexyl etc.), optionally halogenated $C_{1-6}$ alkoxy, optionally halogenated $C_{1-6}$ alkylthio, hydroxy, amino, mono-$C_{1-6}$ alkylamino (for example, methylamino, ethylamino, propylamino, isopropylamino, butylamino etc.), di-$C_{1-6}$ alkylamino (for example, dimethylamino, diethylamino, ethylmethylamino, dipropylamino, dibutylamino etc.), $C_{1-6}$ alkyl-carbonyl (for example, acetyl, propionyl etc.), carboxyl, $C_{1-6}$ alkoxy-carbonyl (for example, methoxycarbonyl, ethoxycarbonyl, propoxycarbonyl, butoxycarbonyl etc.), carbamoyl, mono-$C_{1-6}$ alkylcarbamoyl (for example, methylcarbamoyl, ethylcarbamoyl etc.), di-$C_{1-6}$ alkylcarbamoyl (for example, dimethylcarbamoyl, diethylcarbamoyl etc.), $C_{6-10}$ aryl-carbamoyl (for example, phenylcarbamoyl, naphthylcarbamoyl etc.), sulfo, $C_{1-6}$ alkylsulfonyl (for example, methylsulfonyl, ethylsulfonyl etc.) $C_{6-10}$ aryl (for example, phenyl, naphthyl etc.), $C_{6-10}$ aryloxy (for example, phenyloxy, naphthyloxy etc.) and the like.

$R^{10}$ is preferably hydrogen atom, cyano, $C_{1-6}$ alkyl (for example, methyl, ethyl, propyl, isopropyl, butyl, isobutyl, pentyl, hexyl etc.), $C_{1-6}$ alkoxy (for example, methoxy, ethoxy, propoxy, isopropoxy, butoxy, isobutoxy, pentyloxy, hexyloxy etc.), hydroxy, amino, mono-$C_{1-6}$ alkylamino, di-$C_{1-6}$ alkylamino, $C_{1-6}$ alkyl-carbonyl or the like.

When Y denotes nitrogen atom, Za is preferably a bond.

Y is preferably CH or N. More preferable is CH.

Examples of "an optionally substituted hydrocarbon group" represented by $R^9$ include the same hydrocarbon groups as the aforementioned "optionally substituted hydrocarbon group".

Examples of "an acyl group" represented by $R^9$ include the same acyl groups as the aforementioned "acyl group".

$R^9$ is preferably hydrogen atom or $C_{1-6}$ alkyl. More preferable is hydrogen atom.

Za is preferably a bond or a group represented by the formula $NR^9$ (wherein respective symbols are as defined above).

Examples of the "divalent aliphatic hydrocarbon group which may be via oxygen atom, nitrogen atom or sulfur atom" in the "divalent aliphatic hydrocarbon group which may have substituent(s) and which may be via oxygen atom, nitrogen atom or sulfur atom" represented by Zb denotes (i) methylene or (ii) divalent groups obtained by removing each one of hydrogen atoms bonding to different two carbon atoms of saturated or unsaturated aliphatic hydrocarbon, which optionally contain 1 or 2, preferably 1 oxygen atom, nitrogen atom or sulfur atom between carbon atoms or at its terminal. Among them, groups having 1 to 8 carbon atoms are preferable.

Embodiments thereof include:
(i) $C_{1-8}$ alkylene (for example —$CH_2$—, —$(CH_2)_2$—, —$(CH_2)_3$—, —$(CH_2)_4$—, —$(CH_2)_5$—, —$(CH_2)_6$—, —$(CH_2)_6$—, —$(CH_2)_7$—, —$(CH_2)_8$-etc.)
(ii) $C_{2-8}$ alkenylene (for example, —CH=CH—, —$CH_2$—CH=CH—, —$CH_2$—CH=CH—$CH_2$—, —$CH_2$—$CH_2$—CH=CH—, —CH=CH—$CH_2$—$CH_2CH_2$—, —$CH_2$—$CH_2$—$CH_2$—$CH_2$—CH=CH— etc.)
(iii) $C_{2-8}$ alkynylene (for example, —C≡C—, —$CH_2$—C≡C—, —$CH_2$-c≡C—$CH_2$—$CH_2$— etc.)
(iv) a group represented by the formula: —$(CH_2)_p$—M—$(CH_2)_q$—(wherein p and q denote an integer of 0 to 8, and p+q is an integer of 1 to 8, M denotes O, $NR^{11}$, S, SO or $SO_2$).

$R^{11}$ in the formula denotes hydrogen atom, $C_{1-6}$ alkyl (for example, methyl, ethyl, propyl, isopropyl, butyl, isobutyl, pentyl, hexyl etc.), $C_{3-6}$ cycloalkyl (for example, cyclopropyl, cyclobutyl, cyclopentyl etc.), $C_{6-14}$ aryl (for example, phenyl, 1-naphthyl, 2-naphthyl, biphenylyl etc.), $C_{7-11}$ aralkyl (for example, benzyl, phenethyl etc.) or acyl. Examples of the "acyl" include the same acyls as the aforementioned "acyl".

M is preferably O or $NR^{11}$. $R^{11}$ is preferably hydrogen atom.

p and q are preferably an integer of 0 to 5. More preferable is an integer of 0 to 4.

Examples of the "substituent" which may be possessed by the "divalent aliphatic hydrocarbon group which may via oxygen atom, nitrogen atom or sulfur atom) include a halogen atom (for example, fluorine, chlorine, bromine, iodine etc.), nitro, cyano, optionally halogenated $C_{1-6}$ alkyl, $C_{3-6}$ cycloalkyl (for example, cyclopropyl, cyclobutyl, cyclopentyl, cyclohexyl etc.), optionally halogenated $C_{1-6}$ alkoxy, optionally halogenated $C_{1-6}$ alkylthio, hydroxy, amino, mono-$C_{1-6}$ alkylamino (for example, methylamino, ethylamino, propylamino, isopropylamino, butylamino etc.), di-$C_{1-6}$ alkylamino (for example, dimethylamino, diethylamino, ethylmethylamino, dipropylamino, dibutylamino etc.), optionally substituted $C_{6-14}$ aryl (for example, phenyl, 1-naphthyl, 2-naphthyl, biphenylyl etc.), optionally substituted $C_{7-11}$ aralkyl (for example, benzyl, phenethyl etc.), optionally substituted $C_{6-10}$ aryloxy (for example, phenyloxy, naphthyloxy etc.), oxo, acyl and the like. Examples of the "optionally halogenated $C_{1-6}$ alkyl", the "optionally halogenated $C_{1-6}$ alkoxy" and the "optionally halogenated $C_{1-6}$ alkylthio" include those described in detail for the substituent for an aromatic group represented by Zc. Examples of a "substituent" in the "optionally substituted $C_{6-14}$ aryl", the "optionally substituted $C_{7-11}$ aralkyl" and the "optionally substituted $C_{6-10}$ aryloxy" include the same substituents as the "substituents" which may be possessed by the "hydrocarbon group" in the "optionally substituted hydrocarbon group". Examples of the "acyl" include the same acyls as the aforementioned "acyl".

The substituents may bind at 1 to 5 replaceable positions. When the number of substituents is two or more, they may be same or different.

Zb is preferably a bond or a group represented by the formula: —$(CH_2)_p$-M-$(CH_2)_q$— (symbols in the formula are as defined above). More preferable is a bond or a group represented by the formula: —$(CH_2)_p$—$NR^{1''}$-$(CH_2)_q$— (symbols in the formula are as defined above).

Examples of the "optionally substituted amino group" as a substituent for the "dihydrofuran ring" include the same groups as "(2) optionally substituted amino group" as a substituent for the "optionally substituted heterocyclic group".

The "dihydrofuran ring" represented by C ring may have 1 to 3 aforementioned substituents at a replaceable position on its ring. When the number of substituents is two or more, they may be the same or different.

In the above formula, R denotes hydrogen atom or an acyl group.

Examples of an "acyl group" represented by R include same acyl groups as those described above.

As R, hydrogen atom, formyl, or $C_{1-6}$ alkyl-carbonyl or $C_{6-10}$ aryl-carbonyl, each optionally substituted with a halogen atom, is preferable.

When A ring is a non-aromatic 5-membered nitrogen-containing heterocyclic ring represented by the formula: —$(CH_2)_m$—N(R")—C(=O)—R' (wherein R' denotes an optionally substituted hydrocarbon group, an optionally substituted amino group or an optionally substituted heterocyclic group, R" denotes hydrogen atom or an optionally substituted hydrocarbon group, and M denotes an integer of 1 to 4) in the above formula (i) B ring denotes a benzene ring which has further substituent(s).

Examples of the "optionally substituted hydrocarbon group", the "optionally substituted amino group" and the "optionally substituted heterocyclic group" represented by R', and the "optionally substituted hydrocarbon group" represented by R" include the same groups as the aforementioned "optionally substituted hydrocarbon group", "optionally substituted amino group" and "optionally substituted heterocyclic group".

Examples of the "non-aromatic 5-membered nitrogen-containing heterocyclic ring" represented by A ring include pyrrolidine and the like as described above.

In the above formula (I), when A ring is a non-aromatic 6-membered nitrogen-containing heterocyclic ring substituted with oxo, B ring is a wholly substituted benzene ring.

Examples of the "non-aromatic 6-membered nitrogen-containing heterocyclic ring" represented by A ring include piperidine and the like as described above.

Examples of a substituent for the "wholly substituted benzene ring" represented by B ring include substituents as described above.

As Compound (I), a compound represented by the formula:

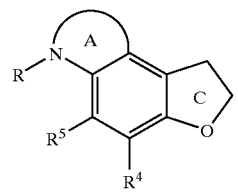

wherein $R^4$ and $R^5$ are the same or different and are hydrogen atom, a halogen atom, hydroxy group, amino group, or a hydrocarbon group which may be via oxygen atom, nitrogen atom or sulfur atom and which may have substituent(s), and other symbols are as defined above, provided that both $R^4$ and $R^5$ do not denote hydrogen atom at the same time, or salt thereof are preferable.

Examples of the "halogen atom" and "hydrocarbon group which may be via oxygen atom, nitrogen atom or sulfur atom and which may have substituent(s)" represented by $R^4$ or $R^5$ include the same groups as the "halogen atom" and the "hydrocarbon group which may be via oxygen atom, nitrogen atom or sulfur atom and which may have substituent(s)" as a substituent for B ring.

It is preferable that both $R^4$ and $R^5$ do not donate hydrogen atom at the same time and $R^4$ and $R^5$ are the same or different and are a hydrocarbon group which may be via oxygen atom, nitrogen atom or sulfur atom and which may have substituent(s). $R^4$ and $R^5$ are more preferably a lower alkyl group (preferably, $C_{1-6}$ alkyl group such as methyl, ethyl, propyl, isopropyl, butyl, isobutyl, s-butyl, t-butyl, pentyl, hexyl etc.) or a lower alkoxy group (preferably $C_{1-6}$ alkoxy group such as methoxy, ethoxy, propoxy, isopropoxy, butoxy, isobutoxy, s-butoxy, t-butoxy etc.), particularly preferably a lower alkyl group (preferably $C_{1-6}$ alkyl group such as methyl, t-butyl etc.).

As Compound (I), a compound represented by the formula:

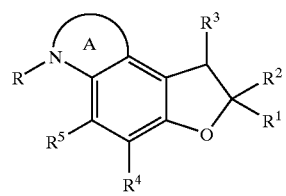

wherein $R^1$ and $R^2$ are the same or different and denote hydrogen atom, an optionally esterified or amidated carboxyl group or an optionally substituted hydrocarbon group, $R^3$ denotes hydrogen atom, an optionally substituted hydrocarbon group or an optionally substituted amino group, and other symbols are as defined above, or salts thereof are more preferable.

Examples of the "optionally esterified or amidated carboxyl group" represented by $R^1$ and $R^2$ include the same groups as the "(11) optionally esterified carboxyl group" and "(12) optionally substituted carbamoyl group" as a "substituent" which may be possessed by the aforementioned "heterocyclic group".

Examples of the "optionally substituted hydrocarbon group" represented by $R^1$ and $R^2$ include the same groups as the "optionally substituted hydrocarbon group" as a substituent for C ring.

$R^1$ is preferably a lower alkyl group (for example, $C_{1-6}$ alkyl group such as methyl, ethyl, propyl, isopropyl, butyl, isobutyl, s-butyl, t-butyl, pentyl, hexyl etc.) or the like.

$R^2$ is preferably a lower alkyl group (for example, $C_{1-6}$ alkyl group such as methyl, ethyl, propyl, isopropyl, butyl, isobutyl, s-butyl, t-butyl, pentyl, hexyl etc.) which may be substituted with a halogen atom or a hydroxy, or an optionally substituted cyclic amino group (the aforementioned "optionally substituted cyclic amino group", in particular, preferably D ring is 1,2,4,5-tetrahydro-3H-benzazepine, piperidine or piperazine, Y is CH, Za is a bond or a group represented by the formula $NR^9$ ($R^9$ is as defined above), Zb is a bond or a group represented by the formula —($CH_2$)$_p$—M—($CH_2$)$_q$— (symbols in the formula are as defined above), and Zc is (1) $C_{1-6}$ alkyl optionally substituted with 1 or 2 $C_{6-14}$ aryls, or (2) $C_{6-14}$ aryl, 2-pyridyl, 3-pyridyl, 4-pyridyl, 2-indolyl, 3-indolyl or benzimidazole, each optionally having 1 to 3 substituents selected from a halogen atom, C-6 alkoxy and $C_{1-6}$ alkyl), and the like.

In the above formula, $R^3$ denotes hydrogen atom, an optionally substituted hydrocarbon group or an optionally substituted amino group.

Examples of the "optionally substituted hydrocarbon group" and the "optionally substituted amino group" represented by $R^3$ include the same groups as the "optionally substituted hydrocarbon group" and the "optionally substituted amino group" as a substituent for the aforementioned C ring.

$R^3$ is preferably hydrogen atom or a phenyl group optionally having a substituent ($C_{1-6}$ alkyl group such as methyl etc.), more preferably hydrogen atom.

In the above formula, preferably, $R^1$ is a lower alkyl group (for example, $C_{1-6}$ alkyl group such as methyl, ethyl, propyl, isopropyl, butyl, isobutyl, s-butyl, t-butyl, pentyl, hexyl etc.), $R^2$ is a lower alkyl group (for example, $C_{1-6}$ alkyl group such as methyl, ethyl, propyl, isopropyl, butyl, isobutyl, s-butyl, t-butyl, pentyl, hexyl etc.) optionally substituted with an optionally substituted cyclic amino group (the aforementioned "optionally substituted cyclic amino group"), halogen atom or hydroxy, $R^3$ is hydrogen atom or a phenyl group optionally having a substituent ($C_{1-6}$ alkyl group such as methyl etc.), $R^4$ and $R^5$ are a lower alkyl group (preferably, $C_{1-6}$ alkyl group such as methyl, t-butyl etc.), and A ring is a non-aromatic 5- to 7-membered nitrogen-containing heterocyclic ring (preferably a non-aromatic 5-membered nitrogen-containing heterocyclic ring) which may be further substituted with a lower alkyl group (preferably, $C_{1-5}$ alkyl group such as methyl etc.).

In the aforementioned formula, Aa ring denotes a non-aromatic 5- to 7-membered nitrogen-containing heterocyclic ring which may have further substituent(s).

Examples of the "non-aromatic 5- to 7-membered nitrogen-containing heterocyclic ring which may have further substituent(s)" represented by Aa ring include the same heterocyclic ring as the "non-aromatic 5- to 7-membered nitrogen-containing heterocyclic ring which may have further substituent(s)" represented by the A ring.

In the aforementioned formula, Ba ring denotes a benzene ring which may have further substituent(s).

Examples of a substituent which may be possessed by a benzene ring being Ba ring include the same substituents as those possessed by a benzene ring being the aforementioned B ring.

In the aforementioned formula, Ca ring denotes a dihydrofuran ring which may have further substituent(s).

Examples of the "dihydrofuran ring which may have further substituent(s)" represented by Ca ring include the same rings as the "dihydrofuran ring which may have further substituent(s)" represented by a aforementioned C ring.

In the aforementioned formula, Ra denotes hydrogen atom or an acyl group.

Examples of the "acyl group" represented by Ra include the same groups as the "acyl group" represented by the aforementioned R.

As Aa ring, Ba ring, Ca ring and Ra, the aforementioned preferable rings or groups in the aforementioned A ring, B ring, C ring and R are preferable.

As a salt of Compound (I) or (I'), for example, pharmacologically acceptable salts are used. Examples thereof include a salt with an inorganic base, ammonium salt, a salt with an organic base, a salt with an inorganic acid, a salt with an organic acid, a salt with a basic or acidic amino acid. Preferable examples of the salt with an inorganic base include alkali metal salts such as sodium salt, potassium salt and the like, alkaline earth metal salts such as calcium salt, magnesium salt and the like, or aluminum salt and the like. Suitable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Suitable examples of the salt with an inorganic acid include salts with hydrochloric acid, hydrobromic acid, nitric acid, sulfuric acid, phosphoric acid and the like. Suitable examples of the salt with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Suitable examples of the salt with a basic amino acid include salts with arginine, lysine, ornithine and the like. Suitable examples of the salt with an acidic amino acid include salts with aspartic acid, glutamic acid and the like.

Inter alia, pharmaceutically acceptable salts are preferable. When Compound (I) or (I') has a basic functional group, examples thereof include salts with an inorganic acid such as hydrochloric acid, hydrobromic acid, nitric acid, sulfuric acid, phosphoric acid and the like, as well as salts with an organic acid such as acetic acid, phthalic acid, fumaric acid, oxalic acid, tartaric acid, maleic acid, citric acid, succinic acid, methanesulfonic acid, p-tolenesulfonic acid and the like. When Compound (I) or (I') has an acidic functional group, examples thereof include alkali metal salts such as sodium salt, potassium salt and the like, alkaline earth metal salts such as calcium salt, magnesium salt and the like, ammonium salt and the like.

A process for preparing Compound (I) will be described below. Compounds (Ia) and (Ib) are compounds included in Compound (I).

Compound (I') can be prepared by the same process for preparing Compound (I) or a similar process.

Each symbol in compounds in the following reaction schemes is as defined above. Compounds in the reaction scheme include salts thereof and examples thereof include the same salts as those for Compound (I).

Compound (I) is prepared by steps shown in Synthesis process 1.

Compounds (III), (VI), (X), (XII), (XIII), (XX), (XXX) and (XXXIV) are commercially easily available or may be prepared by a per se known process or a similar process.

Synthesis process 1

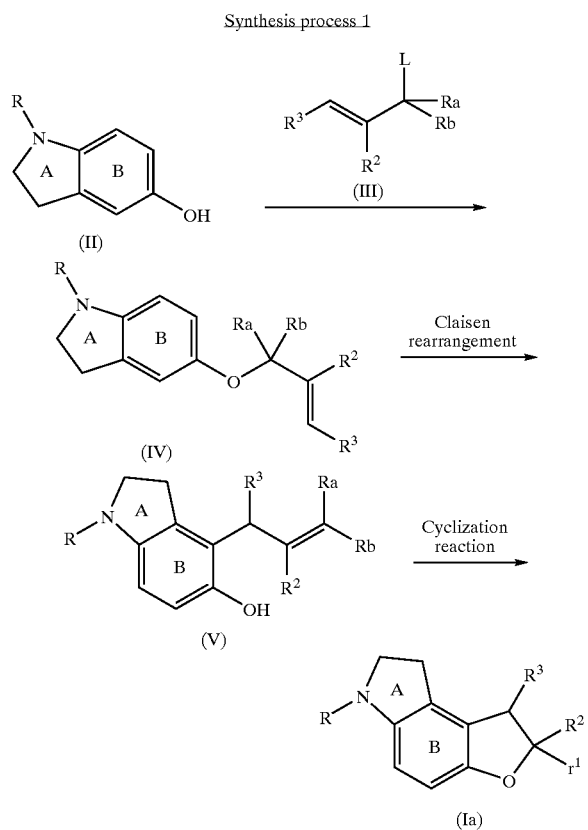

Compound (IV) is prepared by reacting Compound (II) and Compound (III) optionally in the presence of a base.

Ra and Rb in the formula are a substituent forming a part of $R^1$ and examples thereof are the same substituents as substituents which may be possessed by the "hydrocarbon group".

Examples of a "leaving group" represented by L include hydroxy, a halogen atom (for example, fluorine, chlorine, bromine, iodine etc.), optionally halogenated $C_{1-5}$ alkylsulfonyloxy (for example, methanesulofonyloxy, ethanesulfonyloxy, trichloromethanesulfonyloxy etc.), optionally substituted $C_{6-10}$ arylsulfonyloxy and the like. Examples of the "optionally substituted $C_{6-10}$ arylsulfonyloxy" include $C_{6-10}$ arylsulfonyloxy (for example, phenylsulfonyloxy, naphthylsulfonyloxy etc.) optionally having 1 to 3 substituents selected from $C_{1-6}$ alkyl (for example, methyl, ethyl etc.), $C_{1-6}$ alkoxy (for example, methoxy, ethoxy etc.) and nitro, more particularly, benzenesulfonyloxy, m-nitrobenzenesulfonyloxy, p-toluenesulfonyloxy and the like.

The amount of Compound (III) to be used is about 1.0 to about 5.0 mole, preferably about 1.0 to about 2.0 mole relative to 1 mole of Compound (II).

Examples of the "base" include inorganic bases such as sodium hydroxide, potassium hydroxide and the like, basic salts such as sodium carbonate, potassium carbonate, cesium carbonate, sodium bicarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like. The amount of the base to be used is about 1.0 to about 5.0 mole, preferably about 1.0 to about 2.0 mole relative to 1 mole of Compound (II).

This reaction is advantageously carried out using an inert solvent. Such solvent is not particularly limited as long as the reaction proceeds. For example, solvents such as alcohols, ethers, aliphatic hydrocarbons, aromatic hydrocarbons, amides, halogenated hydrocarbons, nitrites, sulfoxides and the like and a mixture thereof are preferable.

The reaction time is usually about 30 minutes to about 48 hours, preferably about 1 hours to about 24 hours. A reaction temperature is usually about −20 to about 150° C., preferably about 0 to about 100° C.

In place of the above reaction, a Mitsunobu reaction (Synthesis, 1981, pp 1–27) may be used.

The reaction is carried out by reacting Compound (II) and Compound (III) wherein L is OH in the presence of azodicarboxylates (for example, diethyl azodicarboxylate etc.) and phosphines (for example, triphenylphosphine, tributylphosphine etc.).

The amount of Compound (III) wherein L is OH to be used is about 1.0 to about 5.0 mole, preferably about 1.0 to about 2.0 mole relative to 1 mole of Compound (II).

The amount of the "azodicarboxylates" and that of the "phosphines" to be used are about 1.0 to about 5.0 mole, preferably about 1.0 to about 2.0 mole relative to 1 mole of Compound (II), respectively.

This reaction is advantageously carried out by using an inert solvent. Such solvent is not particularly limited as long as the reaction proceeds. For example, solvent such as ethers, aliphatic hydrocarbons, aromatic hydrocarbons, amides, halogenated hydrocarbons, nitrites, sulfoxides and a mixture thereof are preferable.

The reaction time is usually about 5 minutes to about 48 hours, preferably about 30 minutes to about 24 hours. A reaction time is usually about −20 to about 200° C., preferably about 0 to about 100° C.

Compound (V) is prepared by subjecting Compound (IV) to Claisen rearrangement.

This reaction is advantageously carried out without a solvent, or by using an inert solvent. Such solvent is not particularly limited as long as the reaction proceeds. For example, alcohols, aliphatic hydrocarbons, aromatic hydrocarbons, organic acids, ethers, anilines, halogenated hydrocarbons or a mixture thereof are used.

Alternatively, this reaction may be carried out optionally using an acid catalyst. As the acid catalyst, Lewis acids such as aluminum chloride, boron tribromide and the like are used. For example, in the case of Lewis acid, an amount of the acid catalyst is usually about 0.1 to about 20 mole, preferably about 0.1 to about 5 mole relative to 1 mole of Compound (IV). The reaction time is usually about 30 minutes to about 24 hours, preferably about 1 hours to about 6 hours. The reaction temperature is usually about −70 to about 300° C., preferably about 150 to about 250° C.

Although the product may be used in the next reaction as the reaction solution itself or as a crude product, it may be isolated from the reaction mixture according to a conventional method, and may be easily purified by a normal separating means (for example, recrystallization, distillation, chromatography etc.).

Compound (Ia) can be prepared by ring-closing Compound (V) in the presence of a protonic acid or a Lewis acid.

As the protonic acid, mineral acids such as hydrochloric acid, hydrobromic acid, sulfuric acid and the like, sulfonic acids such as methanesulfonic acid, trifluoromethanesulfonic acid, fluorosulfonic acid and the like are used. As the Lewis acids, aluminum chloride, aluminum bromide, titanium pentachloride, tin (IV) chloride, zinc chloride, boron trichloride, boron tribromide, boron trifluoride and the like are used. Usually, the protonic acid or the Lewis acid is used alone. Optionally, both may be combined. When the protonic acid is used, it is used at an amount of about 1.0 to about 200 mole, preferably about 1.0 to about 100 mole relative to 1 mole of Compound (V). When the Lewis acid is used, it is used at an amount of about 1.0 to about 5.0 mole, preferably about 1.0 to about 3.0 mole relative to 1 mole of Compound (V). This reaction is advantageously carried out by using an inert acid. Such solvent is not particularly limited as long as the reaction proceeds. For example, solvents such as ethers, aliphatic hydrocarbons, aromatic hydrocarbons, amides, halogenated hydrocarbons, nitriles, sulfoxides and the like or a mixture thereof are preferable. The reaction temperature is usually about −20 to about 150° C., preferably about 0 to about 100° C. The reaction time is usually about 5 minutes to about 24 hours, preferably about 5 hours. Although the product (VI) may be used as the reaction solution itself or as a crude product, it may be isolated from the reaction mixture according to a conventional method, and may be easily purified by a separating means such as recrystallization, distillation, chromatography and the like.

Alternatively, Compound (Ia) can be prepared by reacting Compound (V) and a halogenating regent.

As the "halogenating regent", halogens such as bromine, chlorine, iodine and the like, imides such as N-bromosuccinicimide and the like, halogen adducts such as benzyltrimethylammonium iodide dichloride, benzyltrimethylammonium tribromide and the like are used. An amount of the halogenating regent to be used is about 1 to about 5 mole, preferably about 1 to about 2 mole relative to 1 mole of Compound (V).

This reaction is advantageously carried out by using an inert solvent. Such solvent is not particularly limited as long as the reaction proceeds. For example, alcohols, aliphatic hydrocarbons, aromatic hydrocarbons, amides, halogenated hydrocarbons, nitriles, sulfoxides, organic acids, nitroalkanes, aromatic amines, or a mixture thereof are used.

This reaction is carried out optionally in the presence of a base or a radical initiator, or under light irradiation.

Examples of the "base" include basic salts such as sodium carbonate, potassium carbonate, cesium carbonate, sodium bicarbonate, sodium acetate, potassium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like. The amount of the base to be used is about 0.8 to about 10 mole relative to 1 mole to Compound (V).

Examples of the "radical initiator" include benzoyl peroxide, azobisisobutyronitrile and the like. The amount of the radical initiator to be used is about 0.01 to about 1 mole relative to 1 mole of Compound (V).

In the case of the light irradiation, a halogen lamp can be used.

The reaction temperature is usually about −50 to about 150° C., preferably about 0 to about 100° C. The reaction time is usually about 5 minutes to about 24 hours, preferably about 10 minutes to about 12 hours.

Although the product may be used in the next reaction as the reaction solution itself or as a crude product, it may be isolated from the reaction mixture according to a conventional method, and may be easily purified by a normal separating means (for examples, recrystallization, distillation, chromatography etc.).

Alternatively, Compound (Ia) can be prepared by treating Compound (V) with an organic peracid to cyclize it optionally in the presence of a base. Examples of the organic peracid include m-chloroperbenzoic acid, peracetic acid and the like. The organic peracid is used at an amount of about 1.0 to about 5.0 mole, preferably about 1.0 to about 2.0 mole relative to 1 mole of Compound (V). This reaction is advantageously carried out by using an inert solvent. Such solvent is not particularly limited as long as the reaction proceeds. For example, solvents such as ethers, aliphatic hydrocarbons, aromatic hydrocarbons, amides, halogenated hydrocarbons, nitriles, sulfoxides, organic acids, aromatic amines and the like or a mixture thereof are preferable. Examples of the base which is optionally used include inorganic bases such as sodium carbonate, potassium carbonate, cesium carbonate, calcium carbonate, sodium dicarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like. The reaction temperature is usually about −20 to about 150° C., preferably about 0 to about 100° C. The reaction time is usually about 5 minutes to about 24 hours, preferably about 10 minutes to about 5 hours. The product (Ia) can also be isolated from the reaction mixture according to a conventional method, and can be easily purified by a separating means such as recrystallization, distillation, chromatography and the like.

Alternatively, Compound (I) can be prepared by steps shown in Synthesis process 2.

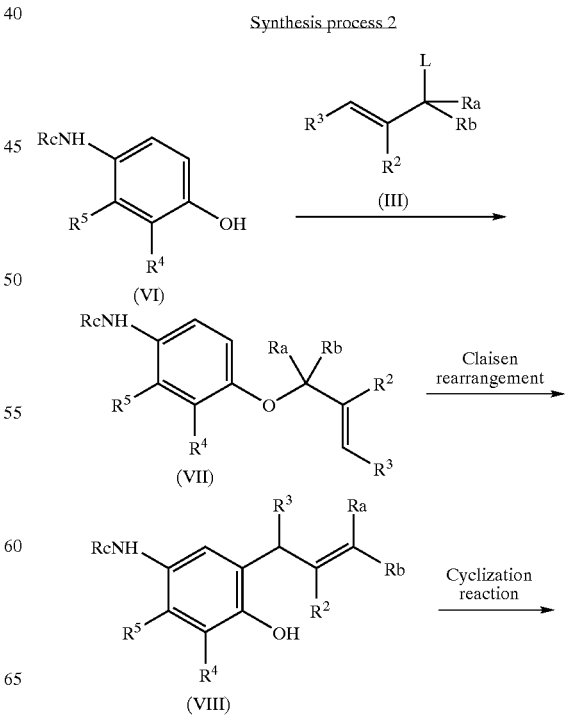

-continued

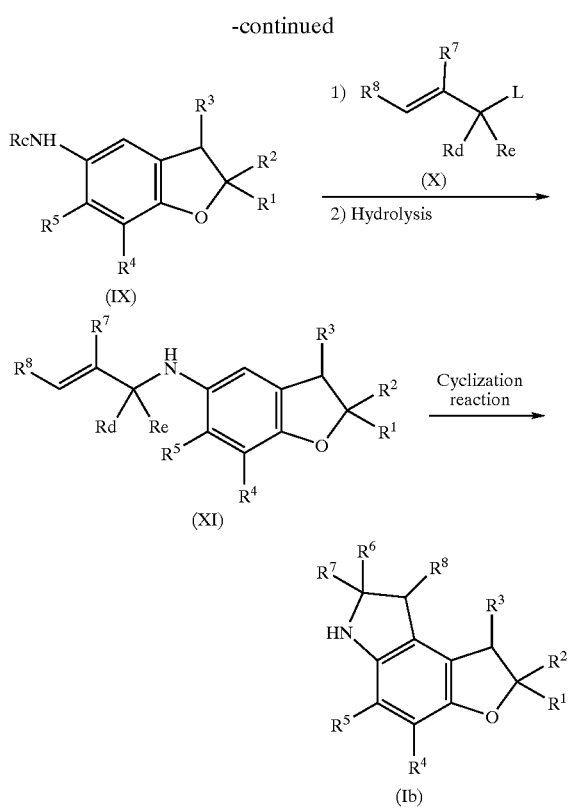

Steps from Compound (VI) to Compound (IX) are carried out according to a process for preparing Compound (Ia) from Compound (II) in the reaction scheme 1.

Rc denotes an acyl group and examples thereof include the same groups as the aforementioned "acyl group".

In the formula, Rd and Re are a substituent forming a part of $R^6$ and examples thereof include the same substituents as substituents which may be possessed by the "hydrocarbon group".

Compound (XI) is prepared by reacting Compound (IX) and Compound (X) optionally in the presence of a base.

The amount of Compound (X) to be used is about 1.0 to about 5.0 mole, preferably about 1.0 to about 2.0 mole relative to 1 mole of Compound (IX).

Examples of the "base" include inorganic bases such as sodium hydroxide, potassium hydroxide and the like, basic salts such as sodium carbonate, potassium carbonate, cesium carbonate, sodium bicarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide and the like, metal alkoxides such as sodium methoxide, sodium ethoxide, potassium tert-butoxide and the like. The amount of the base to be used is about 1.0 to about 5.0 mole, preferably about 1.0 to about 2.0 mole relative to 1 mole of Compound (IX).

This reaction is advantageously carried out by using an inert solvent. Such solvent is not particularly limited as long as the reaction proceeds. For example, solvents such as alcohols, ethers, aliphatic hydrocarbons, aromatic hydrocarbons, amides, halogenated hydrocarbons, nitrites, sulfoxides or a mixture thereof are preferable.

The reaction time is usually about 30 minutes to about 48 hours, preferably about 1 hours to about 24 hours. The reaction temperature is usually about −20 to about 150° C., preferably about 0 to about 100° C.

In place of the above reaction, a Mitsunobu reaction (Synthesis, 1081, pp 1–27) may be used.

The reaction is carried out by reacting Compound (IX) and Compound (X) wherein L is OH in the presence of azodicarboxylates (for example, diethyl azodicarboxylate etc.) and phosphines (for example, triphenylphosphine, tributylphosphine etc.).

The amount of Compound (X) wherein L is OH is about 1.0 to about 5.0 mole, preferably about 1.0 to about 2.0 mole relative to 1 mole of Compound (IX).

The amount of the "azodicarboxylates" and that of the "phosphines" to be used are about 1.0 about 5.0 mole, preferably about 1.0 to about 2.0 mole relative to 1 mole of Compound (IX), respectively.

This reaction is advantageously carried out by using an inert solvent. Such solvent is not particularly limited as long as the reaction proceeds. For example, solvents such as ethers, aliphatic hydrocarbons, aromatic hydrocarbons, amides, halogenated hydrocarbons, nitrites, sulfoxides or a mixture thereof are preferable.

The reaction time is usually about 5 minutes to about 48 hours, preferably about 30 minutes to about 24 hours. The reaction temperature is usually about −20 to about 150° C., preferably about 0 to about 100° C.

Compound (Ib) is prepared by subjecting Compound (XI) to Claisen rearrangement in the presence of an acid catalyst, followed by a ring-closing reaction.

As the acid catalyst, Lewis acids such as zinc chloride, aluminum chloride, tin chloride and the like are used. The amount of the acid catalyst to be used is usually about 0.1 to about 20 mole, preferably about 1 to about 5 mole relative to 1 mole of Compound (XI).

This reaction is advantageously carried out without a solvent or by using an inert solvent. Such solvent is not particularly limited as long as the reaction proceeds. For example, alcohols, aliphatic hydrocarbons, aromatic hydrocarbons, organic acids, ethers, anilines, halogenated hydrocarbons or a mixture thereof are used.

The reaction time is usually about 30 minutes to about 24 hours, preferably about 1 to about 6 hours. The reaction temperature is usually about −70 to about 300° C., preferably about 150 to about 250° C.

Although the product may be used in the next reaction as the reaction solution itself or as a crude product, it may be isolated from the reaction mixture according to a conventional method, and may be easily purified by a normal separating means (for example, recrystallization, distillation, chromatography etc.).

The 2,3-dihydro-5-hydroxyindole derivative used in Synthesis process 1 is prepared by steps shown in Synthesis processes 3-1, 3-2 and 3-3.

The preparation process by Synthesis process 3-1 will be described below.

31

Synthesis process 3-1

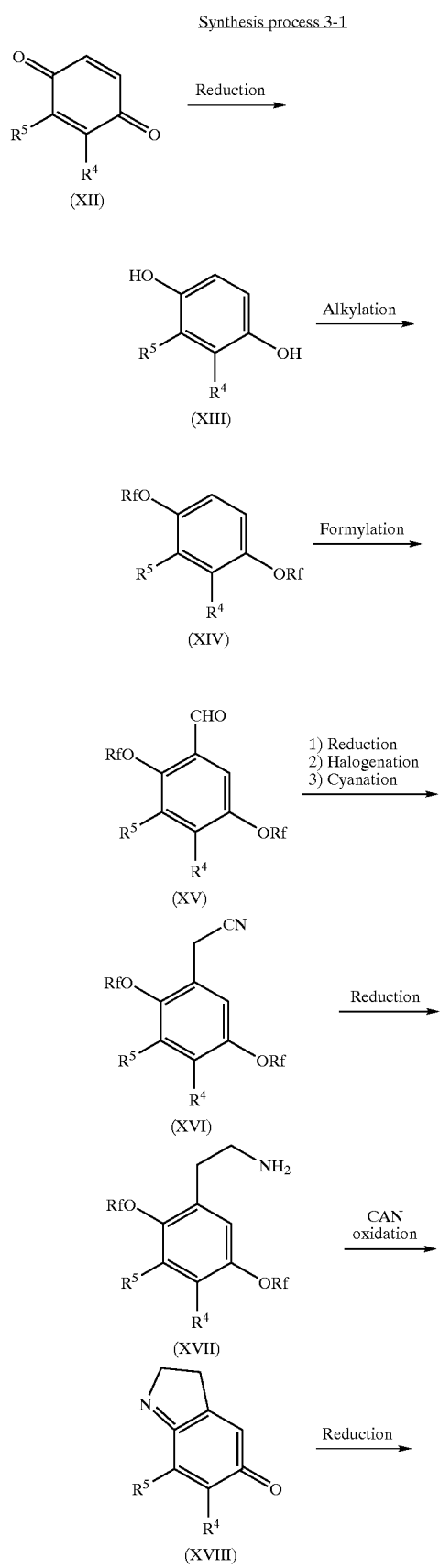

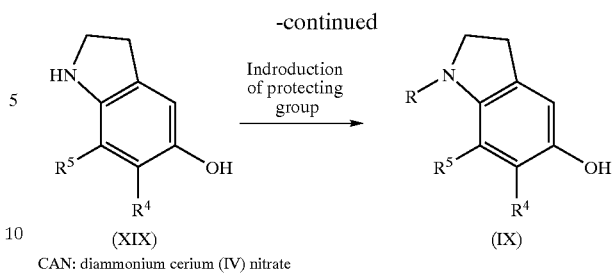

CAN: diammonium cerium (IV) nitrate

Compound (XIII) is prepared by reducing Compound (XII). As a reducing agent, sodium hydrosulfite, tin (II) chloride and the like are used. In the case of sodium hydrosulfite, the amount of the reducing agent to be used is about 1.0 to about 30 mole, preferably about 2.0 to about 5.0 mole relative to 1 mole of Compound (XII). In the case of tin (II) chloride, the amount is about 1.0 to about 10 mole, preferably about 2.0 to about 5.0 mole relative to 1 mole of Compound (XII). When tin (II) chloride is used as a reducing agent, the reaction is usually carried out in the presence of a mineral acid such as hydrochloric acid and the like. This reaction is advantageously carried out by using an inert solvent. Such solvent is not particularly limited as long as the reaction proceeds. For example, water, or a mixture of water and alcohols, ethers, aliphatic hydrocarbons, aromatic hydrocarbons or amides. The reaction time is usually about 10 minutes to about 10 hours, preferably about 10 minutes about 2 hours. The reaction temperature is usually about 0 to about 100° C., preferably about 5 to about 80° C. Although the product may be used in the next reaction as the reaction solution itself or a crude product, it may be isolated from the reaction mixture according to a conventional method, and may be easily purified by a separating means such as recrystallization, distillation, chromatography and the like.

Alternatively, Compound (XIII) may be prepared by reducing Compound (XII) using a hydrogenation catalyst such as platinum oxide, palladium carbon, Raney nickel, Raney cobalt and the like, and hydrogen. The amount of the hydrogenation catalyst to be used is about 0.1 to about 1000% by weight, preferably about 1 to about 300% by weight relative to Compound (XII).

This reaction is advantageously carried out by using an inert solvent. Such solvent is not particularly limited as long as the reaction proceeds. For example, solvents such as alcohols, ethers, aliphatic hydrocarbons, aromatic hydrocarbons, amides, organic acids such as formic acid, acetic acid and the like, and a mixture thereof are preferable. The reaction time is different depending on the activity and amount of the catalyst to be used and usually about 10 minutes to about 100 hours, preferably about 10 minutes to about 10 hours. The reaction temperature is usually about 0 to about 120° C., preferably about 20 to about 80° C. When the hydrogenation catalyst is used, hydrogen pressure is usually about 1 to about 100 atmospheres. Although the product may be used in the next reaction as the reaction solution itself or as a crude product, it may be isolated from the reaction mixture according to a conventional method, and may be easily purified by a separating means such as recrystallization, distillation, chromatography and the like.

Compound (XIV) is prepared by alkylating Compound (XIII). In this reaction, Compound (XII) and a corresponding alkylating agent (for example, corresponding alkyl halide, sulfonic ester of alcohol etc.) are reacted optionally in the presence of a base. The alkylating agent is used at an amount of about 1.0 to about 5.0 mole, preferably about 1.0 to about 2.0 mole relative to 1 mole of Compound (XIII). Examples of the base include inorganic bases such as sodium carbonate, potassium carbonate, cesium carbonate, sodium bicarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as sodium amide, lithium diisopropylamide, lithium hexamethyldisilazide, metal alkoxides such as sodium methoxide, sodium ethoxide, potassium tert-butoxide and the like. The base is used at an amount of about 2.0 to about 1.0 mole, preferably about 2.0 to about 5.0 mole relative to 1 mole of Compound (XIII). This reaction is advantageously carried out by using an inert solvent. Such solvent is not particularly limited as long as the reaction proceeds. For example, solvents such as alcohols, ethers, aliphatic hydrocarbons, aromatic hydrocarbons, amides, halogenated hydrocarbons, nitrites, sulfoxides and the like or a mixture thereof are preferable. The reaction time is usually about 30 minutes to about 48 hours, preferably about 1 hour to about 24 hours. The reaction temperature is usually about −20 to about 200° C., preferably about 0 to about 150° C. This reaction is advantageously carried out by using an inert solvent. Such solvent is not particularly limited as long as the reaction proceeds. For example, solvents such as alcohols, ethers, aliphatic hydrocarbons, aromatic hydrocarbons, amides, halogenated hydrocarbons, nitrites, sulfoxides and the like or a mixture thereof are preferable. The reaction time is usually about 30 minutes to about 48 hours, preferably about 1 hour to about 24 hours. The reaction temperature is usually about −20 to about 200° C., preferably about 0 to about 150° C.

Compound (XV) is prepared by formylating Compound (XIV). In this reaction, Compound (XIV) is reacted with dichloromethyl alkyl ethers in the presence of an acid catalyst and then hydrolyzed to obtain formyl compound. Examples of the dichloromethyl alkyl ethers include dichloromethyl methyl ether, dichloromethyl butyl ether and the like. The dichloromethyl alkyl ethers are used at an amount of about 1.0 to about 10.0 mole, preferably about 1.0 to about 5.0 mole relative to 1 mole of Compound (XIV). Examples of the acid catalyst include titanium (IV) chloride, aluminum chloride, tin (IV) chloride and the like. The acid catalyst is used usually at an amount of about 1.0 to about 10.0 mole, preferably about 1.0 to about 5.0 mole relative to 1 mole of Compound (XIV). This reaction is advantageously carried out by using an inert solvent. Such solvent is not particularly limited as long as the reaction proceeds. For example, solvents such as ethers, aliphatic hydrocarbons, aromatic hydrocarbons, halogenated hydrocarbons, nitrites and the like or a mixture thereof are preferable. The reaction time is usually 10 minutes to 48 hours, preferably 30 minutes to 24 hours. The reaction temperature is usually −20 to 100° C., preferably 0 to 80° C. The subsequent hydrolysis is performed by mixing the reaction solution with water. Alternatively, formylation may be carried out under Vilsmeier reaction conditions. In this method, formamides are reacted in the presence of an acid catalyst and then hydrolyzed with a base to obtain the formyl compound. Examples of the formamides include methylformamide, dimethylformamide and the like. The formamides are used at an amount of about 1.0 to about 10.0 mole, preferably about 1.0 to about 5.0 mole relative to 1 mole of Compound (XIV). Examples of the acid catalyst include phosphoryl chloride, thionyl chloride and the like. The acid catalyst is used usually at an amount of about 1.0 to about 10.0 mole, preferably about 1.0 to about 5.0 mole relative to 1 mole of Compound (XIV). This reaction is advantageously carried out by using an inert solvent. Such solvent is not particularly limited as long as the reaction proceeds. For example, solvents such as amides, ethers, aliphatic hydrocarbons, aromatic hydrocarbons, halogenated hydrocarbons, nitriles and the like or a mixture thereof are preferable. The reaction time is usually 10 minutes to 48 hours, preferably 30 minutes to 24 hours. The reaction temperature is usually −20 to 100° C., preferably 0 to 80° C. Subsequent hydrolysis is carried out by mixing the reaction solution with a base. Examples of the base include inorganic bases such as sodium hydroxide, potassium hydroxide, basic salts such as sodium carbonate, potassium carbonate, cesium carbonate, sodium bicarbonate and the like. The amount of the base to be used is about 1.0 to about 30.0 mole, preferably about 5.0 to about 10.0 mole relative to 1 mole of Compound (XIV). Although the product may be used in the next reaction as the reaction solution itself or a crude product, it may be isolated from the reaction mixture according to a conventional method, and may be easily purified by a separating means such as recrystallization, distillation, chromatography, and the like.

Compound (XVI) is prepared by reducing Compound (XV), and halogenating the resulting alcohol, which is subsequently substituted with cyano group. Examples of a reducing agent used in reduction include metal hydrides such as aluminum hydride, diisobutylaluminium hydride and the like, metal hydrogen complex compounds such as lithium aluminum hydride, sodium borohydride and the like, borane complexes such as borane tetrahydrofuran complex, borane dimethyl sulfide complex and the like, alkylboranes such as thexylborane, disiamylborane and the like, diborane, metals such as zinc, aluminum, tin, iron and the like, alkali metals such as sodium, lithium and the like in liquid ammonia (Birch reduction) and the like. In addition, as a hydrogenation catalyst, catalysts such as palladium carbon, platinum oxide, Raney nickel, Raney cobalt and the like are used. The amount of the reducing agent to be used is about 1.0 to about 10 mole, preferably about 1.0 to about 3.0 mole relative to 1 mole of Compound (XV) in the case of the metal hydrides, about 1.0 to about 10 mole, preferably about 1.0 to about 3.0 mole relative to 1 mole of Compound (XV) in the case of metal hydrogen complex compounds, about 1.0 to about 5.0 mole relative to 1 mole of Compound (XV) in the case of borane complexes, alkylboranes or diborane, about 1.0 to about 20 equivalents, preferably about 1 to about 5 equivalents in the case of metals, about 1 to about 20 equivalents, preferably about 1 to about 5 equivalents when an alkali metal is used, catalysts such as palladium carbon, platinum oxide, Raney nickel, Raney cobalt and the like are used at an amount of about 5 to about 1000% by weight, preferably about 10 to about 300% weight relative to Compound (XIV) in the case of hydrogenation. This reaction is advantageously carried out by using an inert solvent. Such solvent is not particularly limited as long as the reaction proceeds. For example, solvents such as alcohols, ethers, aliphatic hydrocarbons, aromatic hydrocarbons, amides, organic acids and the like or a mixture thereof are preferable. The reaction time is different depending upon a kind or an amount of a reducing agent to be used or the activity and amount of a catalyst and is usually about 1 hour to about 100 hours, preferably about 1 hour to about 50 hours. The reaction temperature is usually about 0 to about 120° C., preferably about 20 to 80° C. When the hydrogenation catalyst is used, hydrogen pressure is usually about 1 to about 100 atmospheres. Although the product may be used in the next reaction as the reaction solution itself or a crude product, it may be isolated from the reaction mixture according to a conventional method, and may be easily isolated by a separating means such as recrystallization, distillation, chromatography and the like.

Examples of a halogenating agent in subsequent halogenation include halogenated thionyls such as thionyl chloride, thionyl bromide and the like, halogenated phosphoryls such as phosphoryl chloride, phosphoryl bromide and the like, halogenated phosphoruses such as phosphorus pentachloride, phosphorus trichloride, phosphorus pentabromide, phosphorus tribromide and the like, oxalyl halides such as oxalyl chloride and the like, phosgene and the like. The halogenating agent is used at an amount of about 1.0 to about 30 mole, preferably about 1.0 to about 10 mole relative to 1 mole of an alcohol. This reaction is advantageously carried out without a solvent, or by using an inert solvent. Such solvent is not particularly limited as long as the reaction proceeds. For example, solvents such as aliphatic hydrocarbons, aromatic hydrocarbons, ethers, amides, halogenated hydrocarbons and the like or a mixture thereof are preferable. The reaction time is usually about 10 minutes to about 12 hours, preferably about 10 minutes to about 5 hours. The reaction temperature is usually about −10 to about 200° C., preferably about −10 to about 120° C. Although the product may be used in the next reaction as the reaction solution itself or as a crude product, it may be isolated from the reaction mixture according to a conventional method, and may be easily purified by a separating means such as recrystallization, distillation, chromatography and the like.

As a cyanizing agent in subsequent cyanization, inorganic cyanides such as sodium cyanide, potassium cyanide and the like are used. The inorganic cyanide is used at an amount of about 0.8 to about 10 mole, preferably about 1.0 mole to about 5 mole relative to 1 mole of a halide. This reaction is advantageously carried out by using an inert solvent. Such solvent is not limited as long as the reaction proceeds. For example, solvents such as ethers, aliphatic hydrocarbons, aromatic hydrocarbons, amides, halogenated hydrocarbons, nitriles, sulfoxides and the like or a mixture thereof are preferable. The reaction temperature is usually about −20 to about 150° C., preferably about 0 to about 100° C. The reaction time is usually about 5 minutes to about 24 hours, preferably about 10 minutes to about 5 hours. Although the product may be used in the next reaction as the reaction solution itself or as a crude product, it may be isolated from the reaction mixture according to a conventional method, and may be easily purified by a separation means such as recrystallization, distillation, chromatography and the like.

Compound (XVII) is prepared by reducing Compound (XVI). Examples of a reducing agent which is used for reduction include metal hydrides such as aluminum hydride, diisobutylaluminium hydride and the like, metal hydrogen complex compounds such as lithium aluminum hydride, sodium borohydride and the like, borane complexes such as borane tetrahydrofuran complex, borane dimethyl sulfide complex and the like, alkylboranes such as thexylborane, disiamylborane and the like, diborane, or metals such as zinc, aluminum, tin, iron and the like, an alkali metal such as sodium, lithium and the like in liquid ammonia (Birch reduction) and the like. In addition, as a hydrogenation catalyst, catalysts such as palladium carbon, platinum oxide, Raney nickel, Raney cobalt and the like are used. The amount of the reducing agent to be used is about 1.0 to about 10 mole, preferably about 1.0 to about 3.0 mole relative to 1 mole of Compound (XVI) in the case of metal hydrides, about 1.0 to about 10 mole, preferably about 1.0 to about 3.0 mole relative to 1 mole to Compound (XVI) in the case of metal hydrogen complex compounds, about 1.0 to about 5.0 mole relative to 1 mole of Compound (XVI) in the case of borane complexes, alkylboranes or diborane, about 1.0 to about 20 equivalents, preferably about 1 to about 5 equivalents in the case of metals, about 1 to about 20 equivalents, preferably about 1 to about 5 equivalents when an alkali metal is used, catalysts such as palladium carbon, platinum oxide, Raney nickel, Raney cobalt and the like are used at an amount of about 5 to about 1000% by weight, preferably about 10 to about 300% by weight relative to Compound (XVI) in the case of hydrogenation. This reaction is advantageously carried out by using an inert solvent. Such solvent is not particularly limited as long as the reaction proceeds. For example, solvents such as alcohols, ethers, aliphatic hydrocarbons, aromatic hydrocarbons, amides, organic acids and the like or a mixture thereof are preferable. The reaction time is different depending upon a kind or an amount of a reducing agent used or the activity and amount of a catalyst and is usually about 1 hour to about 100 hours, preferably about 1 hour to about 50 hours. The reaction temperature is usually about 0 to about 120° C., preferably about 20 to about 80° C. When the hydrogenation catalyst is used, hydrogen pressure is usually about 1 to about 100 atmospheres. Although the product (XVII) may be used in the next reaction as the reaction solution itself or as a crude product, it may be isolated from the reaction mixture according to a conventional method, and may be easily purified by a separating means such as recrystallization, distillation, chromatography and the like.

Compound (XVIII) is prepared by oxidizing Compound (XVII) with an oxidizing agent, which is subsequently treated with a base to cyclize it. As the oxidizing agent, diammonium cerium nitrate is frequently used. The oxidizing agent is used at an amount of about 1.0 to about 10 mole, preferably about 1.0 to about 3.0 mole relative to Compound (XVII). This reaction is advantageously carried out by using an inert solvent. Such solvent is not particularly limited as long as the reaction proceeds. For example, mixed solvents such as water and nitriles, alcohols, ethers, aliphatic hydrocarbons, aromatic hydrocarbons, amides and the like are preferable. The reaction time is different depending upon a kind or an amount of an oxidizing agent used or the activity and amount of a catalyst and is usually about 10 minutes to about 5 hours, preferably about 30 minutes to about 1 hour. The reaction temperature is usually about 10 to about 120° C., preferably about 0 to about 60° C. Compound (XVIII) which is a cyclized product can be prepared by treating the resulting benzoquinoline with a base. Examples of the base include inorganic bases such as sodium carbonate, potassium carbonate, cesium carbonate, calcium carbonate, sodium bicarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like. As a reaction solvent, the same ones as solvents used for the oxidizing reaction are used. The reaction temperature is usually about −20 to about 150° C., preferably about 0 to about 100° C. The reaction time is usually about 5 minutes to about 24 hours, preferably about 10 minutes to about 5 hours. The product (XVIII) may be isolated from the reaction mixture according to a conventional method, and may be easily purified by a separating means such as recrystallization, distillation, chromatography and the like.

Compound (XIX) is prepared by reducing Compound (XVIII). As a reducing agent, for example, sodium hydrosulfite, tin (II) chloride and the like are used. The amount of the reducing agent to be used is about 1.0 to about 30 mole, preferably about 2.0 to about 5.0 mole, relative to 1 mole of Compound (XVIII) in the case of sodium hydrosulfite, and about 1.0 to about 10 mole, preferably about 2.0 to about 5.0 mole relative to 1 mole of Compound (XVIII) in the case of tin chloride (II). When tin (II) chloride is used as the reducing agent, the reaction is carried out usually under acidic conditions in the presence of a mineral acid such as hydrochloric acid. This reaction is advantageously carried out by using an inert solvent. Such solvent is not particularly limited as long as the reaction proceeds. For example, water, or mixed solvents such as water and alcohols, ethers, aliphatic hydrocarbons, aromatic hydrocarbons, amides and the like are preferable. The reaction time is usually about 10 minutes to about 10 hours, preferably about 10 minutes to about 2 hours. The reaction temperature is usually about 0 to about 100° C., preferably about 5 to about 80° C. Although the product may be used in the next reaction as the reaction solution itself or as a crude product, it may be isolated from the reaction mixture according to a conventional method, and may be easily purified by a separating means such as recrystallization, distillation, chromatography and the like.

Compound (IIa) is synthesized by acylating Compound (XIX). Compound (XIX) and an acylating agent are reacted optionally in the presence of a base or an acid. Examples of the acylating agent include corresponding carboxylic acids or reactive derivatives thereof (for example, acid halide, acid anhydride, ester etc.). The acylating agent is used at an amount of about 1.0 to about 5.0 mole, preferably about 1.0 to about 2.0 mole relative to 1 mole of Compound (XIX). This reaction is advantageously carried out without a solvent or by using an inert solvent. Such solvent is not particularly limited as long as the reaction proceeds. For example, solvents such as ethers, aliphatic hydrocarbons, aromatic hydrocarbons, amides, halogenating hydrocarbons, nitrites, sulfoxides, aromatic amines and the like or a mixture thereof are preferable. Examples of the optionally used base include triethylamine, pyridine and the like. Examples of the optionally used acid include methanesulfonic acid, p-toluenesulfonic acid, camphorsulfonic acid and the like. The reaction temperature is about −20 to about 150° C., preferably about 0 to about 100° C. The reaction time is usually about 5 minutes to about 24 hours, preferably about 10 minutes to about 5 hours. Although the product (IIa) may be used in the next reaction as the reaction solution itself or as a crude product, it may be isolated from the reaction mixture according to a conventional method, and may be easily purified by a separating means such as recrystallization, distillation, chromatography and the like.

Compound (XIX) can also be prepared by steps shown in Synthesis process 3-2.

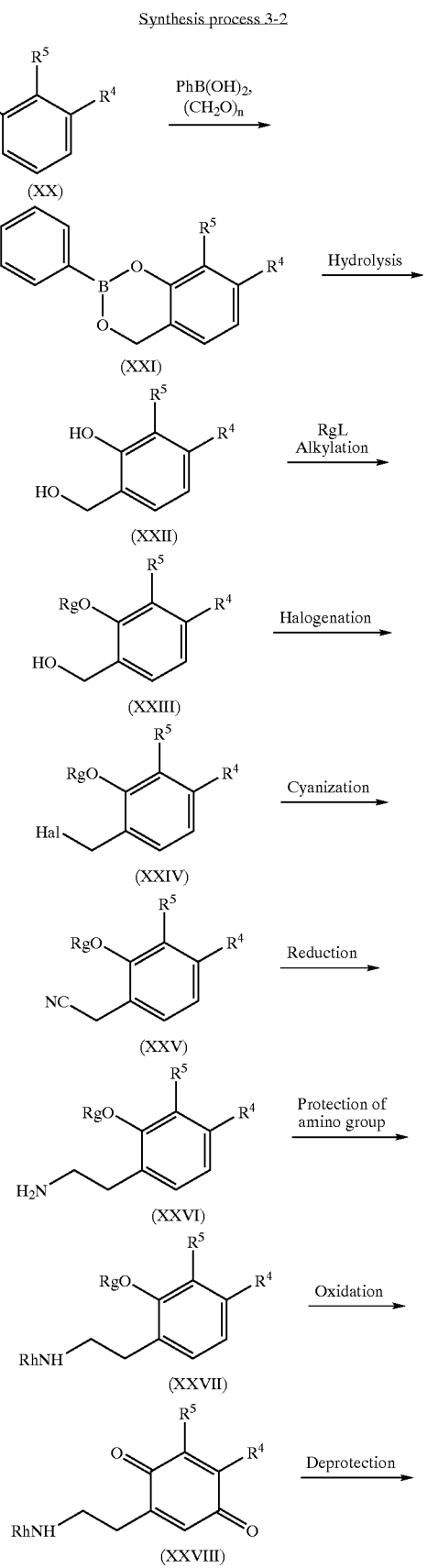

-continued

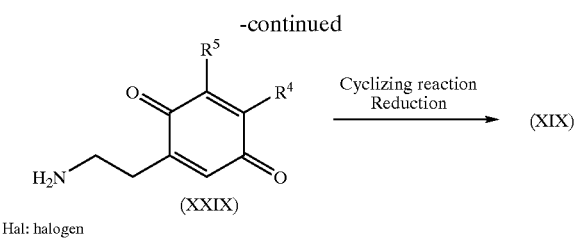

Hal: halogen

Compound (XXII) is prepared by selectively hydroxymethylating at an ortho position of the phenol, from Compound (XX) via Compound (XXI).

Compound (XXI) is prepared by reacting Compound (XX) with phenylboronic acid and paraformaldehyde in the presence of an acid catalyst while removing water formed with a Dean Stark trap or the like. Phenylboronic acid is used at an amount of about 1.0 to about 10 mole, preferably about 1.0 to about 1.5 mole relative to 1 mole of Compound (XX). Paraformaldehyde is used at an amount of about 1.0 to about 30 mole, preferably about 3 to about 5 mole relative to 1 mole of Compound (XX). As the acid catalyst, for example, organic acids such as acetic acid, propionic acid, trichloroacetic acid and the like are used at an amount of about 0.01 to about 10 mole, preferably about 0.1 to about 0.5 mole relative to 1 mole of Compound (XX). This reaction is advantageously carried out by using an inert solvent. Such solvent is not particularly limited as long as the reaction proceeds. Usually, examples of the solvents include ethers, aliphatic hydrocarbons, aromatic hydrocarbons and the like or a mixture thereof, preferably benzene and toluene. The reaction temperature is usually about 0 to about 200° C., preferably about 50 to about 150° C. The reaction time is different depending upon the amount of reagents used, a kind of the solvent or the reaction temperature and is usually about 10 minutes to about 10 hours, preferably about 30 minutes to about 3 hours. Although the product may be used in the next reaction as the reaction solution itself or as a crude product, it may be isolated from the reaction mixture according to a conventional method, and may be easily purified by a separating means such as recrystallization, distillation, chromatography and the like.

Compound (XXII) is prepared by deprotecting phenylboronic acid using hydrogen peroxide, 1,3-propanediol, diethanolamine or the like. At this point, a solvent which is inert for the reaction such as benzene, toluene and the like may be used as an auxiliary solvent. The reaction time is different depending upon the amount of reagents used, a kind of the solvent or the reaction temperature and is usually about 10 minutes to about 48 hours, preferably about 5 hours to about 16 hours. Although the product may be used in the next reaction as the reaction solution itself or as a crude product, it may be isolated from the reaction mixture according to a conventional method, and may be easily purified by a separating means such as recrystallization, distillation, chromatography and the like.

Compound (XXIII) is obtained by selectively alkylating hydroxy group of the phenol of Compound (XXII) with an alkylating agent represented by RgL. Rg denotes $C_{1-6}$ alkyl (for example, methyl, ethyl etc.), and L is as defined for the "leaving group" above.

The amount of the alkylating agent to be used is about 0.8 to about 5.0 mole, preferably about 1.0 to about 2.0 mole relative to 1 mole of Compound (XXII).

Examples of the "base" include inorganic bases such as sodium hydroxide, potassium hydroxide and the like, basic salts such as sodium carbonate, potassium carbonate, cesium carbonate, sodium bicarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, alkali metal hydrides such as sodium hydride, potassium hydride and the like, metal amides such as, sodium amide, lithium diisopropylamide, lithium hexamethyldisilazide and the like, metal alkoxides such as sodium methoxide, sodium ethoxide, potassium tert-butoxide and the like. The amount of the base to be used is about 0.8 to about 5.0 mole, preferably about 1.0 to about 2.0 mole relative to 1 mole of Compound (XXII).

This reaction is advantageously carried out by using a solvent which is inert for the reaction. Such solvent is not particularly limited as long as the reaction proceeds. For example, solvents such as alcohols, ethers, aliphatic hydrocarbons, aromatic hydrocarbons, amides, halogenated hydrocarbons, nitrites, sulfoxides and the like or a mixture thereof are preferable.

The reaction time is usually about 30 minutes to about 48 hours, preferably about 1 hour to about 24 hours. The reaction temperature is usually about −20 to about 150° C., preferably about 0 to about 100° C.

Compound (XXIV) is obtained by converting hydroxy group of Compound (XXIII) into a halogen with a halogenating reagent.

As the "halogenating reagent", phosphorus halide such as phosphorous tribromide, phosphorus pentabromide, phosphorus trichloride, phosphorus pentachloride and the like, thionyl halide such as thionyl chloride and the like, triphenylphosphine-carbon tetrahalide, diphenyltrihalogenophospholane, triphenylphosphinedihalogenide, phosphonic acid triphenyldihalogenide and the like are used. The amount of the halogenating reagent to be used is about 1 to about 5 mole, preferably about 1 to about 2 mole relative to 1 mole of Compound (XXIII).

This reaction is advantageously carried out using a solvent which is inert for the reaction. Such solvent is not particularly limited as long as the reaction proceeds. For example, alcohols, aliphatic hydrocarbons, aromatic hydrocarbons, amides, halogenated hydrocarbons, nitrites, sulfoxides, organic acids, nitroalkanes, aromatic amines, or a mixture thereof are used.

The reaction temperature is usually about −50 to about 150° C., preferably about 0 to about 100° C. The reaction time is usually about 5 minutes to about 24 hours, preferably about 10 minutes to about 12 hours.

Although the product may be used in the next reaction as the reaction solution itself or as a crude product, it may be isolated from the reaction mixture according to a conventional method, and may be easily purified by a normal separating means (for example, recrystallization, distillation, chromatography etc.).

Compound (XXV) is obtained by converting the halogen of Compound (XXIV) into cyano, similar to cyanization used for preparing Compound (XVI) from Compound (XV).

Compound (XXVI) is obtained by reducing Compound (XXV) with a reducing agent, similar to preparation of Compound (XVII) from Compound (XVI).

Compound (XXVII) is obtained by protecting amino group of Compound (XXVI) with an acylating agent optionally in the presence of a base or an acid.

The amount of the acylating agent to be used is about 1.0 to about 5.0 mole, preferably about 1.0 to about 2.0 mole relative to 1 mole of Compound (XXVI).

Examples of the "acylating agent" include carboxylic acids corresponding to an acyl group (for example, formyl group, acetyl group, trifluoroacetyl group etc.) normally used as a protecting group, or reactive derivatives thereof (for example, acid halide, acid anhydride, ester etc.).

The amount of the base or acid to be used is about 0.8 to about 5.0 mole, preferably about 1.0 to about 2.0 mole relative to 1 mole of Compound (XXVI).

Examples of the "base" include triethylamine, pyridine, 4-dimethylaminopyridine and the like.

Examples of the "acid" include methanesulfonic acid, p-toluene sulfonic acid, camphorsulfonic acid and the like.

This reaction is advantageously carried out without a solvent or in the presence of a solvent which is inert for the reaction. The solvent is not particularly limited as long as the reaction proceeds. For example, ethers, aromatic hydrocarbons, aliphatic hydrocarbons, amides, halogenated hydrocarbons, nitrites, sulfoxides, aromatic amines and the like or a mixture of two or more of them are used.

The reaction temperature is about −20 to about 150° C., preferably about 0 to about 100° C. The reaction time is usually about 5 minutes to about 24 hours, preferably about 10 minutes to about 5 hours.

Although the product may be used in the next reaction as the reaction solution itself or as a crude product, it may be isolated from the reaction mixture according to a conventional method and may be easily purified by a separating means such as recrystallization, distillation, chromatography and the like.

Compound (XXVIII) is obtained by oxidizing Compound (XXVII) into quinone with an oxidizing agent. As the oxidizing agent, chromic acid is frequently used. The oxidizing agent is used at an amount of about 1.0 to about 10 mole, preferably about 1.0 to about 3.0 mole relative to 1 mole of Compound (XXVII). This reaction is advantageously carried out using a solvent which is inert for the reaction. Such solvent is not particularly limited as long as the reaction proceeds. For example, organic acids, acetic anhydride, aliphatic hydrocarbons, aromatic hydrocarbons, halogenated hydrocarbons, aromatic amines and the like or a mixture of water with them, water and the like are preferable. The reaction time is different depending upon a kind and the amount of the oxidizing agent used and is usually about 10 minutes to about 5 hours, preferably about 30 minutes to about 1 hour. The reaction temperature is usually about −10 to about 120° C., preferably about 0 to about 60° C.

Compound (XXIX) is obtained by deprotecting a protecting group for amino group of Compound (XXVIII) using an acid or a base.

The amounts of the acids and the bases to be used are about 0.1 to about 50 mole, preferably about 1 to about 20 mole, respectively, relative to 1 mole of Compound (XXVIII).

As the "acid", mineral acids such as hydrochloric acid, hydrobromic acid, sulfuric acid and the like, Lewis acids such as boron trichloride, boron tribromide and the like, thiols or sulfides together with Lewis acids, organic acids such as trifluoroacetic acid, toluenesulfonic acid and the like are used.

As the "base", metal hydroxides such as sodium hydroxide, potassium hydroxide, barium hydroxide and the like, basic salts such as sodium carbonate, potassium carbonate and the like, metal alkoxides such as sodium methoxide, sodium ethoxide, potassium tert-butoxide and the like, organic bases such as triethylamine, imidazole, formamidine are used.

This reaction is advantageously carried out without a solvent or in the presence of a solvent which is inert for the reaction. The solvent is not particularly limited as long as the reaction proceeds. For example, alcohols, ethers, aromatic hydrocarbons, aliphatic hydrocarbons, halogenated hydrocarbons, sulfoxides, water and the like or a mixture of two or more of them are used.

The reaction time is usually about 10 minutes to about 50 hours, preferably about 30 minutes to about 12 hours. The reaction temperature is usually about 0 to about 200° C., preferably about 20 to about 120° C.

Compound (XIX) is obtained by cyclizing Compound (XXIX) and subsequently reducing it. The cyclizing reaction may be performed by treating benzoquinone with a base. Examples of the base include inorganic bases such as sodium carbonate, potassium carbonate, cesium carbonate, potassium carbonate, sodium bicarbonate and the like, aromatic amines such as pyridine, lutidine and the like, tertiary amines such as triethylamine, tripropylamine, tributylamine, cyclohexyldimethylamine 4-dimethylaminopyridine, N,N-dimethylaniline, N-methylpiperidine, N-methylpyrrolidine, N-methylmorpholine and the like. As the reaction solvent, the same solvents as those used for the oxidizing reaction are used. The reaction temperature is usually about −20 to about 150° C., preferably about 0 to about 100° C. The reaction time is usually about 5 minutes to about 24 hours, preferably about 10 minutes to about 5 hours. The product may be isolated from the reaction mixture according to a conventional method, and may be easily purified by a separating means such as recrystallization, distillation, chromatography and the like. The subsequent reducing reaction uses the same conditions as those for preparing Compound (XIX) from Compound (XVIII).

Compound (XIX) can also be prepared by steps shown in Synthesis process 3-3.

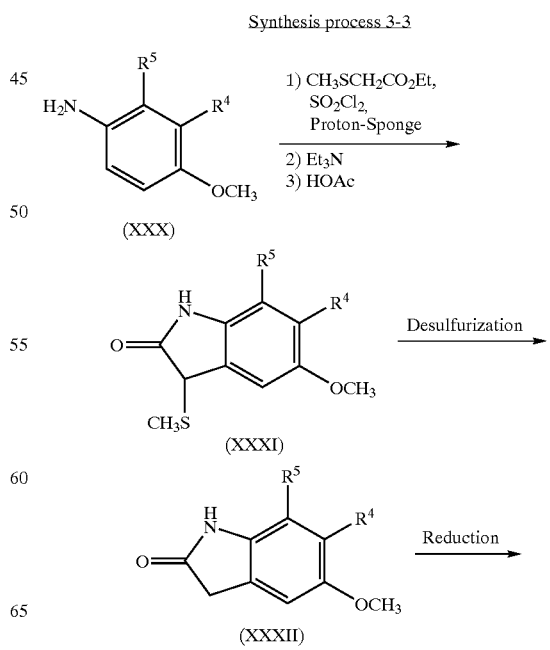

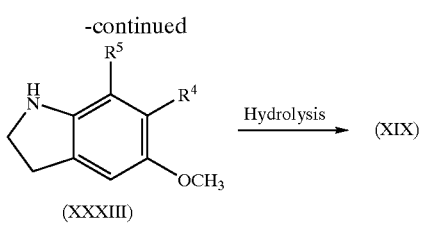

(XXXIII)

Compound (XXXI) can be prepared by reacting Compound (XXX) and alkylchlorosulfonium ethyl acetate and, then, after reaction in the presence of a base, if necessary, heat-treating or acid-treating it to construct an oxyindole ring according to a method of Gassman et al. described in J. Am. Chem. Soc., vol. 95, 6508–6509, 1973. Alkylchlorosulfonium ethyl acetate is obtained by chlorinating ethyl alkylthioacetate with chlorine, sulfuryl chloride, hypochlorite ester or the like. The chlorosulfonium ethyl acetate is used at an amount of about 0.9 to about 1.5 mole, preferably about 1.0 to about 1.2 mole relative to 1 mole of Compound (XXX). This reaction is advantageously carried out using a solvent which is inert for the reaction. Such solvent is not particularly limited as long as the reaction proceeds. Halogenated hydrocarbons and the like are preferable. The reaction time is usually about 5 minutes to about 5 hours, preferably about 30 minutes to about 2 hours. The reaction temperature is usually about −100 to about 50° C., preferably about −80 to about 50° C. Examples of the base include aromatic amines such as pyridine, lutidine and the like, tertiary amines such as triethylamine, tripropylamine, tributylamine, cyclohexyldimethylamine, N,N,N',N'-tetramethyl-1,8-naphthalenediamine, 4-dimethylaminopyridine, N,N-dimethylaniline, N-methylpiperidine, N-methylpyrrolidine, N-methylmorpholine and the like. The reaction temperature is usually about −80 to about 50° C., preferably about 0 to about 20° C. As the optionally used acid, mineral acids such as hydrochloric acid, hydrobromic acid, sulfuric acid and the like, sulfonic acids such as methanesulfonic acid, trifluoromethanesulfonic acid, fluorosulfonic acid and the like, formic acid, acetic acid, trichloroacetic acid and the like are used. The acid is used at an amount of about 1 to about 200 mole, preferably about 1 to about 10 mole relative to 1 mole of Compound (XXX). The reaction time is usually 1 minute to about 5 hours, preferably about 30 minutes to about 2 hours. The reaction temperature is usually about 50 to about 150° C., preferably about 0 to about 50° C. Upon this, a solvent which is inert for the reaction, such as diethyl ether, dichloromethane, toluene and the like may be used as an auxiliary solvent. Alternatively, synthesis may be performed by heating in place of treatment with an acid. The reaction temperature is 50 to 250° C., preferably 50 to 150° C. The reaction temperature is 10 minutes to 48 hours, preferably 30 minutes to 5 hours. Upon this, a solvent which is inert for the reaction, such as toluene, hexane, decalin or the like may be used as an auxiliary solvent. Although the product may be used in the next reaction as a crude product, it may be isolated from the reaction mixture according to a conventional method, and may be easily purified by a separating means such as recrystallization, distillation, chromatography and the like.

Compound (XXXII) can be prepared by desulfurizing Compound (XXXI) using a metal catalyst such as Raney nickel, tin and the like, preferably a Raney nickel catalyst, performing desulfurization using triphenylphosphine and p-toluene sulfonic acid according to a method of Terrence et al. described in Synlett, 663,1996. The Raney nickel catalyst is used at an amount of about 0.1 to about 20 g, preferably about 1 to about 5 g relative to 1 mmole of Compound (XXXI). This reaction is advantageously carried out without a solvent or using a solvent which is inert for the reaction. Such solvent is not particularly limited as long as the reaction proceeds. For example, solvents such as alcohols, ethers, aliphatic hydrocarbons, aromatic hydrocarbons, amides, nitrites and the like or a mixture thereof are preferable. The reaction time is usually about 5 minutes to about 48 hours, preferably about 30 minutes to about 10 hours. The reaction temperature is usually about 0 to about 150° C., preferably about 20 to about 100° C. Although the product may be used in the next reaction as a crude product after removal of a catalyst, it may be isolated from the reaction mixture according to a conventional method, and may be easily purified by a separating means such as recrystallization, distillation, chromatography and the like.

Compound (XXXIII) is prepared by reducing Compound (XXXII). Examples of the reducing agent used in reduction include metal hydrides such as aluminum hydride, diisobutylaluminium hydride and the like, metal hydrogen complex compounds such as lithium aluminum hydride, sodium borohydride, Red-Al and the like, borane complexes such as borane tetrahydrofuran complex, borane dimethylsulfide complex and the like, alkylboranes such as thexylborane, disiamylborane and the like, diborane and the like. The amount of the reducing agent to be used is about 0.3 to about 10 mole, preferably about 0.5 to about 3.0 mole relative to 1 mole of Compound (XXXII) in the case of metal hydrides and metal hydrogen complex compounds, about 1.0 to about 5.0 mole relative to 1 mole of Compound (XXXII) in the case of borane complexes, alkyl boranes or diborane, and about 1.0 to about 20 equivalents, preferably about 1 to about 5 equivalents in the case of metals. This reaction is advantageously carried out by using a solvent which is inert for the reaction. As such solvent, solvents such as ethers, aliphatic hydrocarbons, aromatic hydrocarbons and the like or a mixture thereof are preferable. Although the product may be used in the next reaction as a crude product after removal of a catalyst, it may be isolated from the reaction mixture according to a conventional method, and may be easily purified by a separating means such as recrystallization, distillation, chromatography and the like.

Compound (XIX) can also be prepared by steps shown in Synthesis process 3-4 period.

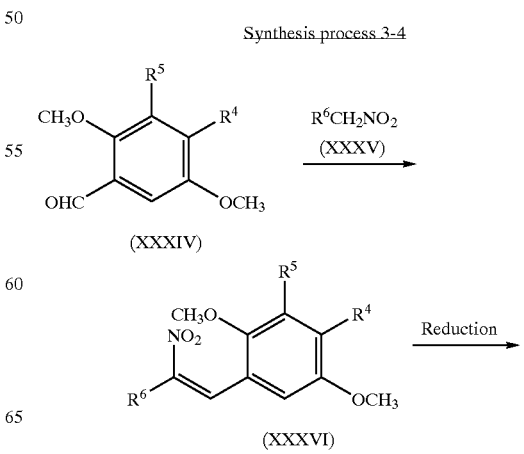

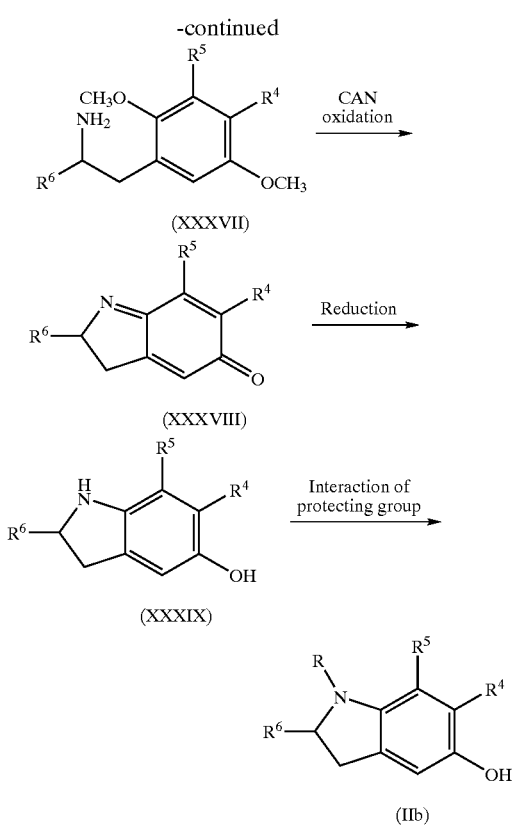

Compound (XXXVI) is prepared by condensing Compound (XXXIV) with Compound (XXXV) in the presence of a base. Compound (XXXV) is used at an amount of about 1.0 to about 300 mole, preferably about 3.0 to about 100 mole relative to 1 mole of Compound (XXXIV). Examples of the base include ammonium salts such as ammonium acetate, ammonium formate and the like, inorganic bases such as sodium carbonate, potassium carbonate, cesium carbonate, calcium carbonate, sodium bicarbonate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrroridine, N-methylmorpholine and the like. The base is used at an amount of about 0.1 to about 10.0 mole, preferable about 0.2 to about 0.5 mole relative to 1 mole of Compound (XXXIV). This reaction is advantageously carried out without a solvent or using a solvent which is inert for the reaction. Such solvent is not particularly limited as long as the reaction proceeds. For example, solvents such as alcohols, ethers, aliphatic hydrocarbons, aromatic hydrocarbons, amides, halogenated hydrocarbons, nitrites, sulfoxides and the like or a mixture thereof are preferable. The reaction time is usually about 30 minutes to about 48 hours, preferably about 1 to about 24 hours. The reaction temperature is usually about 0 to about 150° C., preferably about 20 to about 100° C.

Compound (XXXVII) is prepared by reducing Compound (XXXVI). Examples of a reducing agent used in reduction includes metal hydrides such as aluminum hydride, diisobutylaluminium hydride and the like, metal hydrogen complex compounds such as lithium aluminum hydride, sodium borohydride and the like, borane complexes such as borane tetrahydrofuran complex, borane dimethyl sulfide complex and the like, alkylboranes such as thexylborane, disiamylborane and the like, diborane, or metals such as zinc, aluminum, tin, iron and the like, alkali metals such as sodium, lithium and the like in liquid ammonia (Birch reduction) and the like. In addition, as a hydrogenation catalyst, catalysts such as palladium carbon, platinum oxide, Raney nickel, Raney cobalt and the like are used. The amount of the reducing agent is about 1.0 to about 10 mole, preferably about 1.0 to about 3.0 mole relative to 1 mole of Compound (XXXVI) in the case of metal hydrides, about 1.0 to about 10 mole, preferably about 1.0 to about 3.0 mole relative to 1 mole of Compound (XXXVI) in the case of metal hydrogen complex compounds, about 1.0 to about 5.0 mole relative to 1 mole of Compound (XXXVI) in the case of borane complexes, alkyl boranes or diborane, about 1.0 to about 20 equivalents, preferably about 1 to about 5 equivalents in the case of metals, about 1 to about 20 equivalents, preferably about 1 to about 5 equivalents in the case of alkali metals, and catalysts such as palladium carbon, platinum oxide, Raney nickel, Raney cobalt and the like are used at an amount of about 5 to about 1000% by weight, preferably about 10 to about 300% by weight relative to Compound (XXXVI) in the case of hydrogenation. This reaction is advantageously carried out using a solvent which is inert for the reaction. Such solvent is not particularly limited as long as the reaction proceeds. For example, solvents such as alcohols, ethers, aliphatic hydrocarbons, aromatic hydrocarbons, amides, organic acids and the like or a mixture thereof are preferable. Upon the use of Raney nickel and Raney cobalt catalysts, amines such as ammonia and the like may be further added in order to inhibit side reactions. The reaction time is different depending upon a kind and the amount of the reducing agent or the activity and amount of the catalyst and is usually about 1 hour to about 100 hours, preferably about 1 hour to about 50 hours. The reaction temperature is usually about 0 to about 120° C., preferably about 20 to about 80° C. When a hydrogenation catalyst is used, hydrogen pressure is usually about 1 to about 100 atmospheres. Although the product may be used in the next reaction as the reaction solution itself or as a crude product, it may be isolated from the reaction mixture according to a conventional method, and may be easily purified by a separating means such as recrystallization, distillation, chromatography and the like.

Compound (XXXVIII) is prepared from Compound (XXXVII) by a similar method to that for preparing Compound (XVIII) from Compound (XVII).

Compound (XXXIX) is prepared from Compound (XXXVIII) by a similar method to that for preparing Compound (XIX) from Compound (XVIII).

Compound (IIb) is prepared from Compound (XXXVIX) by a similar method to that for preparing Compound (IIa) from Compound (XIX).

In addition, in the aforementioned respective reactions, when a raw material compound has amino, carboxyl, hydroxy as a substituent, protecting groups normally used in peptide chemistry may be introduced into these groups and, after reaction, protecting groups may be removed as necessary to obtain an end compound.

As the protecting group for amino, formyl or $C_{1-6}$ alkyl-carbonyl (for example, acetyl, propionyl etc.), phenylcarbonyl, $C_{1-6}$ alkoxy-carbonyl (for example, methoxycarbonyl, ethoxycarbonyl etc.), phenyloxycarbonyl, $C_{1-6}$ aralkyloxy-carbonyl (for example, benzyloxycarbonyl etc.), trityl, phthaloyl and the like, each optionally having a substituent are used. As the substituent therefor, a halogen atom (for example, fluorine, chlorine, bromine, iodine etc.), $C_{1-6}$ alkyl-carbonyl (for example, acetyl, propionyl, valeryl etc.), nitro and the like are used. About 1 to 3 these substituents are used.

As the protecting group for carboxyl, $C_{1-6}$ alkyl (for example, methyl, ethyl, propyl, isopropyl, butyl, tert-butyl etc.), phenyl, trityl, silyl and the like, each optionally having a substituent, are used. As the substituent therefor, a halogen atom (for example, fluorine, chlorine, bromine, iodine, etc.), formyl, $C_{1-6}$ alkyl-carbonyl (for example, acetyl, propionyl, butylcarbonyl etc.), nitro, $C_{1-6}$ alkyl (for example, methyl, ethyl, tert-butyl etc.), $C_{6-10}$ aryl (for example, phenyl, naphthyl etc.), and the like are used. About 1 to 3 these substituents are used.

As the protecting group for hydroxy, formyl, or $C_{1-6}$ alkyl (for example, methyl, ethyl, propyl, isopropyl, butyl, tert-butyl etc.), phenyl, $C_{7-11}$ aralkyl (for example, benzyl etc.), $C_{1-6}$ alkyl-carbonyl (for example, acetyl, propionyl etc.), phenyloxycarbonyl, $C_{7-11}$ aralkyloxy-carbonyl (for example, benzyloxy carbonyl etc.), tetrahydropyranyl, tetrahydrofuranyl, silyl and the like, each optionally having a substituent, are used. As the substituent therefor, a halogen atom (for example, fluorine, chlorine, bromine, iodine etc.), $C_{1-6}$ alkyl (for example, methyl, ethyl, tert-butyl etc.), $C_{7-11}$ aralkyl (for example, benzyl etc.), $C_{6-10}$ aryl (for example, phenyl, naphthyl etc.), nitro and the like are used. About 1 to 4 these substituent are used.

As a method for removing a protecting group, a per se known method or a similar method is used. For example, a method of treatment with acid, base, ultraviolet-ray, hydrazine, phenylhydrazine, sodium N-methyldithiocarbamate, tetrabutylammonium fluoride, palladium acetate and the like, or a reduction reaction is used.

In any case, further optionally, a deprotecting reaction, an acylating reaction, an alkylating reaction, a hydrogenation reaction, an oxidation reaction, a reduction reaction, a carbon chain extending reaction and a substituent exchanging reaction can be performed alone or in a combination of two or more thereof to synthesize Compound (I). As these reactions, methods described in Shin-Jikken Kagaku Koza, vols. 14 and 15, 1977 (Maruzen Shuppan) are adopted.

Examples of the aforementioned "alcohols" include methanol, ethanol, propanol, isopropanol, tert-butanol and the like.

Examples of the aforementioned "ethers" include diethyl ether, diisopropyl ether, diphenyl ether, tetrahydrofuran, dioxane, 1,2-dimethoxyethane and the like.

Examples of the aforementioned "halogenated hydrocarbons" include dichloromethane, chloroform, 1,2-dichloroethane, carbon tetrachloride and the like.

Examples of the aforementioned "aliphatic hydrocarbons" include hexane, pentane, cyclohexane and the like.

Examples of the aforementioned "aromatic hydrocarbons" include benzene, toluene, xylene, chlorobenzene and the like.

Examples of the aforementioned "aromatic amines" include pyridine, lutidine, quinoline and the like.

Examples of the aforementioned "amides" include N,N-dimethylformamide, N,N-dimethylacetamide, hexamethylphosphorictriamide and the like.

Examples of the aforementioned "ketones" include acetone, methyl ethyl ketone and the like.

Examples of the aforementioned "sulfoxides" include dimethylsulfoxide and the like.

Examples of the aforementioned "nitriles" include acetonitrile, propionitrile and the like. Examples of the aforementioned "organic acids" include acetic acid, propionic acid, trifluoroacetic acid and the like.

Examples of the aforementioned "anilines" include N,N-diethylaniline, N,N-dimethylaniline and the like.

Examples of the aforementioned "nitroalkanes" include nitromethane, nitroethane and the like.

When the product is obtained in the free state by the aforementioned reaction, it may be converted into a salt according to a conventional method. On the other hand, when the product is obtained as a salt, it may be converted into a free compound or another salt according to a conventional method. The thus-obtained Compound (I) may be isolated or purified from the reaction solution by a known means, for example, conversion dissolution, concentration, solvent extraction, fractionation, crystallization, recrystallization, chromatography and the like.

Compound (I) or (I') is present as a configurational isomer (regioisomer), diastereomer, conformer or the like, optionally, each may be isolated by the aforementioned separating or purifying means. In addition, Compound (I) or (I') is a racemic modification, it may be separated into a S compound and a R compound by a conventional optical resolving means. When stereoisomers are present in Compound (I) or (I'), these isomers alone and a mixture thereof are also included in the present invention.

In addition, (I) and (I') may be a hydrate or a non-hydrate.

Compound (I) or (I') may be labeled with a radioisotope (for example, $^3H$, $^{14}C$, $^{35}S$) or the like.

A prodrug of Compound (I) refers to a compound which is converted into Compound (I) by a reaction with an enzyme or gastric acid under the physiological conditions in the living body, a compound which is changed into Compound (I) by enzymatic oxidation, reduction, hydrolysis or the like, or a compound which is converted into Compound (I) due to hydrolysis with a gastric acid. Examples of a prodrug of Compound (I) include compounds in which amino group of Compound (I) is acylated, alkylated or phosphorylated (for example, compounds in which amino group of Compound (I) is eicosanoylated, alanilated, pentylaminocarbonized, (5-methyl-2-oxo-1,3-dioxolen-4-yl)methoxycarbonized, tetrahydrofuranylated, pyrrolidylmethylated, pivaloyloxymethylated, tert-butylated etc.): compounds in which hydroxy group of Compound (I) is acylated, alkylated, phosphorylated or borate esterified (for example, compounds in which hydroxy group of Compound (I) is acetylated, palmitoylated, propanoylated, pivaloylated, succinylated, furanylated, alanilated, dimethylaminomethylcarbonized etc.); compounds in which carboxyl group of Compound (I) is esterified or amidated (for example, compounds in which carboxyl group of Compound (I) is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methylamidated etc.); and the like. These compounds can be prepared from Compound (I) by the method known per se.

Alternatively, a prodrug of Compound (I) may be a compound which is changed to Compound (I) under the physiological conditions, as described on pages 163 to 198 in "IYAKUHIN no KAIHATSU (Development of Pharmaceuticals)", vol. 7, Molecular Design published by Hirokawa shoten in 1990.

Compound (I) or (I') of the present invention has the excellent lipid peroxidation inhibitory activity, is low toxic and has little side effects and, thus, is useful as a pharmaceutical.

Compound (I) or (I') of the present invention exhibits the lipid peroxidation inhibitory activity based on the excellent antioxidant activity to a mammal (for example, mouse, rat, hamster, rabbit, cat, dog, cow, sheep, monkey, human being etc.) and is effective for preventing and/or treating central nervous diseases and disorders (e.g., ischemic central nervous disorders (for example, cerebral infarct, cerebral bleeding, cerebral edema etc.), central nervous system injury (for example, cranial trauma, head injury, spinal injury, whiplash injury etc.), neurodegeneration disease (for example, Alzheimer's disease, Parkinson's disease, Huntington's chorea, amyotrophic lateral sclerosis etc.), vascular dementia (for example, multi-infarct dementia, Binswanger's disease etc.), manic-depressive psychosis, depressive disease, schizophrenia, chronic pain, trigeminal neuralgia, migraine etc.), circulatory disease or disorder (for example, ischemic cardiac failure (for example, cardiac infarct, angina etc.), arterial sclerosis, arterial restenosis after PTCA (percutaneous transluminal coronary angioplasty), inferior urinary tract disease or disorder (for example, excretion disorder, urinary incontinence) etc.), diabetic neurosis and the like and, thus, is used as an agent for preventing or treating these diseases.

Compound (I) or (I') is low toxic, and can be safely administered orally or parenterally (for example, locally, rectally, intravenouslly etc.) as it is or by formulating into a pharmaceutical composition in which a pharmacologically acceptable carrier is mixed, for example, tablets (including sugar-coated tablets, film-coated tablets), powders, granules, capsules (including soft capsules), solutions, injectables, nasal drops, suppositories, slow releasing agents, cataplasms, chewing gum or the like according to the method known per sue. The content of Compound (I) or (I') in the present preparation is about 0.01 to about 100% by weight based on the total weight of a preparation. The dose is different depending upon an administration subject, an administration route, disease and the like. For example, when orally administered as an agent for treating Alzheimer's disease to an adult, Compound (I) as an active ingredient can be administered at an amount of about 0.1 to about 20 mg/kg weight, preferably about 0.2 to about 10 mg/kg weight, further preferably about 0.5 to about 10 mg/kg weight once to several times par day. Further, other active ingredient(s) [for example, cholinesterase inhibitory agent (for example, aricept (dodesil) etc.), brain function activating drug (for example, idebenone, vinpocetine etc.), Parkinson' disease treating drug (for example, L-dopa etc.), neurotrophic factor etc.] may be used together. Other active ingredients and Compound (I) or (I') may be mixed according to a per se known method, which may be formulated into one pharmaceutical composition (for example, tablets, powders, granules, capsules (including soft capsules), solutions, injectables, suppositories etc.), slow releasing agents etc.). They may be formulated separately, and may be administered to the same subject at the same time or different time.

Examples of the pharmacologically acceptable carrier which may be used for preparing the preparation of the present invention include various organic or inorganic carrier substances which are conventional as a preparation material, for example, excipient, lubricant, binder, disintegrating agent in solid preparations; solvent, solubilizer, suspending agent, isotonic, buffer, soothing agent in liquid preparations. If necessary, conventional additives such as preservative, antioxident, coloring agent, sweetener, adsorbing agent, wetting agent and the like may be used.

Examples of the excipient include lactose, sucrose, D-mannitol, starch, corn starch, crystalline cellulose, light silicic acid anhydride and the like.

Examples of the lubricant include magnesium stearate, calcium stearate, talc, colloidal silica and the like.

Examples of the binder include crystalline cellulose, sucrose, D-mannitol, dextrin, hydroxypropylcellulose, hydroxypropylmethylcellulose, poly(vinyl pyrrolidone), starch, sucrose, gelatin, methylcellulose, sodium carboxymethylcellulose and the like.

Examples of the disintegrating agent include starch, carboxymethylcellulose, potassium carboxymethylcellulose, sodium croscarmellose, sodium carboxymethylstarch, L-hydroxypropylcellulose and the like.

Examples of the solvent include the water for injection, alcohol, propylene glycol, macrogol, sesame oil, corn oil, olive oil and the like.

Examples of the solubilizer include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyltriethanolamine, sodium laurylsulfate, laurylaminopropionic acid, lecithin, benzalkonium chloride, benzethonium chloride, monostearic glycerin and the like; for example, hydrophilic polymers such as polyvinyl alcohol, poly(vinyl pyrrolidone), sodium carboxymethylcellulose, methylcellulose, hydroxymethylcellulose, hydroxyethylcellulose, hydroxypropylcellulose and the like.

Examples of the isotonic include glucose, D-sorbitol, sodium chloride, glycerin, D-mannitol and the like.

Examples of the buffer include buffers such as phosphate, acetate, carbonate, citrite and the like.

Examples of the soothing agent include benzyl alcohol and the like.

Examples of the preservative include paraoxybenzoic esters, chlorobutanol, benzyl alcohol, phenethyl alcohol, dehydroacetic acid, sorbic acid and the like.

Examples of the antioxidant include sulfite, ascorbic acid, α-tocopherol and the like.

PREFERRED EMBODIMENT OF THE INVENTION

The present invention will be further explained in detail below by way of Reference Examples, Examples, Preparation Examples and Test Examples. However, these Examples are mere illustrative examples and do not limit the present invention. Then, variations thereof are possible without departing from the scope of the present invention.

The "room temperature" in the following Reference Examples and Examples usually denotes about 10° C. to about 35° C. "Percents (%)" are by weight, unless otherwise indicated. Yield denotes mol/mol %. As a basic silica gel, NH-DM1020 manufactured by Fuji Silicia Kagaku K.K. was used. As Raney nickel catalyst, NDHT-90 manufactured by Kawaken Fine K.K. was used. In NMR spectra, OH and NH proton and the like which are broad and cannot be confirmed are not described as data.

Other abbreviations used in this text denote the following means.

s: singlet
d: doublet
t: triplet
q: quartet
m: multiplet
dd: double doublet
dt: double triplet
br: broad
J: coupling constant Hz: Hertz
CDCl₃: deuterated chloroform
DMSO-d₆: deuterated dimethyl sulfoxide
CD₃OD: deuterated methanol
¹H-NMR: Proton nuclear magnetic resonance THF: Tetrahydrofuran

EXAMPLES

Reference Example 1

2,5-Dimethoxy-3,4-dimethylbenzaldehyde

To a solution of 1,4-dimethoxy-2,3-dimethylbenzene (100 g, 0.60 mol) and dichloromethyl methyl ether (65 mL, 0.72 mol) in dichloromethane (400 mL) was added dropwise titanium tetrachloride (IV)(100 mL, 0.91 mol) over 30 minutes under ice-cooling, and the mixture was stirred at the same temperature for 30 minutes. The reaction mixture was poured into ice (1 kg), the organic layer was separated, and the aqueous layer was extracted twice with dichloromethane. The combined organic layers were washes with water and saturated brine, passed through sodium sulfate-silica gel, dried (eluted with hexane-ethyl acetate 5:1) and concentrated under reduced pressure. The residue was recrystallized from hexane to obtain 107 g of the title compound.
Yield 92%
mp. 69–71° C.
¹H-NMR (CDCl₃) δ 2.21 (3H, s), 2.24 (3H, s), 3.81 (3H, s), 3.84 (3H, s), 7,14 (1H, s), 10.34 (1H, s)

Reference Example 2

1,4-Dimethoxy-2,3-dimethyl-5-(2-nitro-1-propenyl)benzene

A mixture of 2,5-dimethoxy-3,4-dimethylbenzaldehyde (38.9 g, 0.20 mol), ammonium acetate (10 g, 0.13 mol) and nitroethane (200 mL) was heated to reflux for 2 hours. The reaction mixture was diluted with diisopropyl ether, washed with water and saturated brine, dried over magnesium sulfate, filtered and concentrated under reduced pressure. The residue was recrystallized from hexane to obtain 33.6 g of the title compound.
Yield 67%
mp. 76–81° C.
¹H-NMR(CDCl₃) δ 2.19 (3H, s), 2.34 (3H, s), 2.43 (3H, d, J=0.6 Hz), 3.65 (3H, s), 3.81 (3H, s), 6.65 (1H, s), 8.27 (1H, s)

Reference Example 3

2,3-Dihydro-5-hydroxy-2,6,7-trimethyl-1H-indole-1-carbaldehyde

To a solution of 1,4-dimethoxy-2,3-dimethyl-5-(2-nitro-1-propenyl)benzene (2.51 g, 9.99 mmol) in THF (35 mL) was added lithium aluminum hydride (1.0 g, 26 mmol) under ice-cooling, and the mixture was heated to reflux for 6 hours. Hyflo Super-Cel® (5 g) was added to the reaction mixture, and water (1.5 mL) was added dropwise under ice-cooling. The resulting mixture was suspended in ethyl acetate, filtered, concentrated under the reduced pressure to obtain an oil. This was dissolved in acetonitrile (10 mL), a solution of diammonium cerium (IV) nitrate (10.9 g, 19.9 mmol) in acetonitrile (20 mL) and water (20 mL) was added dropwise under ice-cooling, and the mixture was stirred at room temperature for 2 hours. The reaction mixture was diluted with water, neutralized with sodium bicarbonate and extracted with ethyl acetate three times. The combined organic layers were washed with water and saturated brine, dried over magnesium sulfate, filtered, and concentrated under reduced pressure to obtain the solid. This was dissolved in ethyl acetate, mixed with an aqueous solution of sodium hydrosulfite, shaken, and the precipitated solid was filtered to obtain 0.79 g of 2,3-dihydro-2,6,7-trimethyl-1H-indole-5-ol.
Yield 45%.
Acetic anhydride (0.76 mL, 8.1 mmol) was added to formic acid (4 mL), and the mixture was stirred at room temperature for 15 minutes. To this solution was added 2,3-dihydro-2,6,7-trimethyl-1H-indole-5-ol (0.71 g, 4.0 mmol), and the mixture was stirred at room temperature for 5 hours. Ice was added to the reaction mixture, and precipitated solid was filtered to obtain 0.40 g of the title compound.
Yield 49%.
mp. 155–159° C.
¹H-NMR (CDCl₃) δ 1.25 (3H, d, J=6.6 Hz), 2.19 (3H, s), 2.32 (3H, s), 2.45 (1H, d, J=15.6 Hz), 3.29 (1H, dd, J=15.6, 8.7 Hz), 4.85–5.02 (1H, m, J=7.1 Hz), 6.66 (1H, s), 8.73 (1H, s).

Reference Example 4

2,3-Dihydro-2,6,7-trimethyl-5-[(2-methyl-2-propenyl)oxy]-1H-indole-1-carbaldehyde A suspension of 2,3-dihydro-5-hydroxy-2,6,7-trimethyl-1H-indole-1-carbaldehyde (0.5 g, 2.4 mmol), 3-chloro-2-methyl-1-propene (0.29 mL, 2.9 mmol) and potassium carbonate (0.50 g, 3.6 mmol) in DMF (6 mL) was stirred at 60° C. for 14 hours under the nitrogen atmosphere. Water was added to the reaction mixture, and the mixture was extracted with ethyl acetate two times. The combined organic layers were washed with water and saturated brine, dried over magnesium sulfate, filtered, and concentrated under reduced pressure. The residue was subjected to silica gel columns chromatography (hexane-ethyl acetate 3:1) to obtain 0.60 g of the title compound.
Yield 96%
Oil
¹H-NMR (CDCl₃) δ 1.25 (3H, d, J=6.6 Hz), 1.85 (3H, s), 2,22 (3H, s), 2.33 (3H, s), 2.48 (1H, d, J=15.6 Hz), 3.33 (1H, dd, J=15.6, 8.6 Hz), 4.39 (2H, s), 4.85–5.05 (1H, m), 4.99 (1H, s), 5.11 (1H, s), 6.66 (1H, s), 8.75 (1H, s).

Reference Example 5

2,3-Dihydro-5-hydroxy-2,6,7-trimethyl-4-(2-methyl-2-propenyl)-1H-indole-1-carbaldehyde A solution of 2,3-dihydro-2,6,7-trimethyl-5-[(2-methyl-2-propenyl)oxy]-1H-indole-1-carbaldehyde (0.59 g, 2.3 mmol) in N,N-diethylaniline (3 mL) was stirred at 200° C. for 4.5 hours under the nitrogen atmosphere. The reaction mixture was dissolved in diethyl ether, washed with 1N hydrochloric acid, water and saturated brine, dried over magnesium sulfate, filtered, and concentrated under reduced pressure. The residue was recrystallized from ethyl acetate-diisopropyl ether to obtain 0.41 g of the title compound.
Yield 69%
mp. 133–135° C.

¹H-NMR (CDCl₃) δ 1.25 (3H, d, J=6.6 Hz), 1.75 (3H, s), 2.19 (3H, s), 2.31 (3H, s), 2.46 (1H, d, J=16.2 Hz), 3.1–3.3 (1H, m), 3.30 (2H, s), 4.8–5.05 (1H, m), 4.82 (1H, s), 4.92 (1H, s), 5.09 (1H, s), 8.74 (1H, s)

Reference Example 6

2,5-Dimethoxy-3,4-dimethylbenzeneacetonitrile

To a suspension of 2,5-dimethoxy-3,4-dimethylbenzaldehyde (68.0 g, 0.350 mol) in methanol (400 mL) was added sodium borohydride (6.63 g, 0.175 mol) under ice-cooling, and the mixture was stirred at the same temperature for 15 minutes. Water (20 mL) was added to the reaction mixture, and the mixture was concentrated under reduced pressure. The water was added to the residue, and the mixture was extracted with ethyl acetate three times. The combined organic layers were washed with water and saturated brine, dried over magnesium sulfate, filtered, and concentrated under reduced pressure. The solid was washed with hexane to obtain 66.9 g of alcohol. This was dissolved in THF (400 mL), phosphorus tribromide (24 mL, 0.25 mol) was added dropwise under ice-cooling, and the mixture was stirred at the same temperature for 5 minutes and at room temperature for 1 hour. Reaction mixture was poured into ice water (400 mL), the organic layer was separated, and the aqueous layer was extracted with ethyl acetate two times. The combined organic layers were washed with water and saturated brine, dried over magnesium sulfate, filtered, and concentrated under reduced pressure. The residue was crystallized from methanol to obtain 66.5 g of bromide.

Yield 74%

This compound 57.7 g (0.21 mol) was dissolved in acetonitrile (170 mL), a solution of sodium cyanide (11.2 g, 0.23 mol) in water (100 mL) and acetonitrile (100 mL) was added dropwise over 10 minutes, and the mixture was stirred at room temperature for 19 hours. The organic layer was separated, and the aqueous layer was extracted with ethyl acetate. The combined organic layers were washed with water and saturated brine, dried over magnesium sulfate, filtered, and concentrated under reduced pressure. The residue was recrystallized from diisopropyl ether-hexane to obtain 33.2 g of the title compound.

Yield 77% mp. 98–99° C.

¹H-NMR (CDCl₃) δ 2.14 (3H, s), 2.21 (3H, s), 3.70 (3H, s), 3.74 (2H, s), 3.82 (3H, s), 6.72 (1H, s)

Reference Example 7

2,5-Dimethoxy-3,4-dimethylbenzeneethaneamine hydrochloride

To a solution of 2,5-dimethoxy-3,4-dimethylbenzeneacetonitrile (20.6 g, 0.100 mol) in ethanol (100 mL) were added a saturated ammonia-ethanol solution (250 mL) and Raney nickel (15 g), and the mixture was stirred at 50° C. for 2.5 hours under the hydrogen atmosphere (5.5 atmospheres). The catalyst was filtered, and the filtrate was concentrated under reduced pressure. The residue was dissolved in methanol, a 10% hydrogen chloride-methanol solution (50 mL) was added, and concentrated under the reduced pressure. The residue was recrystallized from methanol-diethyl ether to obtain 18.4 g of the title compound.

Yield 75% mp. 237–240° C.

¹H-NMR (DMSO-d₆) δ 2.04 (3H, s), 2.13 (3H, s), 2.8–3.1 (4H, m), 3.60 (3H, s), 3.75 (3H, s), 6.69 (1H, s), 8.15 (3H, br)

Reference Example 8

2,3-Dihydro-6,7-dimethyl-1H-indole-5-ol

To a suspension of 2,5-dimethoxy-3,4-dimethylbenzeneethaneamine hydrochloride (12.3 g, 0.05 mol) in water (50 mL) was added dropwise a solution of diammonium cerium (IV) nitrate (60.3 g, 0.11 mol) in acetonitrile (100 mL) and water (100 mL) under ice-cooling over 30 minutes, and the mixture was stirred at room temperature for 1 hour. The reaction solution was added dropwise to a suspension of a sodium bicarbonate (65.6 g, 0.78 mol) in water (250 mL)-ethyl acetate (250 mL), and the mixture was stirred at room temperature for 10 minutes. This mixture was filtered, the organic layer was separated, and the aqueous layer was extracted with ethyl acetate two times. The combined organic layers were washed with water, mixed with a 80% sodium hydrosulfite (21.8 g, 0.10 mol) solution in water (200 mL), shaken, and the aqueous layer was separated. The organic layer was washed with saturated brine, dried over magnesium sulfate, filtered, and concentrated under reduced pressure. The residue was recrystallized from ethanol-diisopropyl ether to obtain 5.79 g of the title compound.

Yield 71% mp. 164–167° C.

¹H-NMR (CDCl₃) δ 2.07 (3H, s), 2.13 (3H, s), 2.98 (2H, t, J=8.2 Hz), 3.51 (2H, t, J=8.2 Hz) 6.50 (1H, s)

Reference Example 9

2,3-Dihydro-5-hydroxy-6,7-dimethyl-1H-indole-1-carbaldehyde

To formic acid (100 mL) was added acetic anhydride (23 mL, 0.24 mol) under ice-cooling, and the mixture was stirred at room temperature for 40 minutes. To this solution was added 2,3-dihydro-6,7-dimethyl-1H-indole-5-ol (20.0 g, 0.12 mol) under ice-cooling, and the mixture was stirred at room temperature for 75 minutes. The reaction mixture was concentrated under reduced pressure, and dissolved in the mixture of chloroform-methanol. To this was added an aqueous solution of sodium bicarbonate solution to neutralize, the organic layer was separated, and the aqueous layer was extracted with chloroform three times. The combined organic layers were washed with saturated brine, dried over magnesium sulfate, filtered, and concentrated under reduced pressure. The solid was washed with diisopropyl ether to obtain 22.0 g of the title compound.

Yield 94% mp. 192–193° C.

¹H-NMR (CDCl₃) δ 2.19 (3H, s), 2.32 (3H, s), 2.98 (2H, t, J=7.9 Hz), 4.12 (2H, t, J=7.9 Hz), 5.6–6.1 (1H, br), 6.66 (1H, s), 8.77 (1H, s).

Reference Example 10

2,3-Dihydro-6,7-dimethyl-5-[(2-methyl-2-propenyl)oxy]-1H-indole-1-carbaldehyde

A suspension of 2,3-dihydro-5-hydroxy-6,7-dimethyl-1H-indole-1-carbaldehyde (21.8 g, 0.11 mol), 3-chloro-2-methyl-1-propene (15 mL, 0.15 mol) and potassium carbonate (23.6 g, 0.17 mol) in DMF (200 mL) was stirred at 60° C. for 15 hours under the nitrogen atmosphere. Water was added to the reaction mixture, and the mixture was extracted with ethyl acetate four times. The combined organic layers were washed with water and saturated brine, dried over magnesium sulfate, treated with active carbon, filtered, and concentrated under reduced pressure. The residue was recrystallized from diisopropyl ether-hexane to obtain 20.6 g of title compound.

Yield 74%

A sample for analysis was recrystallized from ethanol-hexane.

mp. 81–83° C.

$^1$H-NMR (CDCl$_3$) δ 1.84 (3H, s), 2.22 (3H, s), 2.33 (3H, s), 3.01 (2H, t, J=7.8 Hz), 4.12 (2H, t, J=7.8 Hz), 4.40 (2H, s), 4.99 (1H, s), 5.10 (1H, s), 6.67 (1H, s), 8.78 (1H, s).

Reference Example 11

2,3-Dihydro-5-hydroxy-6,7-dimethyl-4-(2-methyl-2-propenyl)-1H-indole-1-carbaldehyde A solution of 2,3-dihydro-6,7-dimethyl-5-[(2-methyl-2-propenyl)oxy]-1H-indole-1-carbaldehyde (25.2 g, 0.103 mol) in N,N-diethylaniline (50 mL) was stirred at 200° C. for 8 hours under the nitrogen atmosphere. The reaction mixture was allowed to stand overnight, diisopropyl ether was added, the crystals were filtered, and recrystallized from ethanol to obtain 20.4 g of the title compound.

Yield 81% mp. 150–152° C.

$^1$H-NMR (CDCl$_3$) δ 1.75 (3H, s), 2.19 (3H, s), 2.32 (3H, s), 2.96 (2H, t, J=7.9 Hz), 3.32 (2H, s), 4.12 (2H, t, J=7.9 Hz), 4.82 (1H, s), 4.92 (1H, s), 5.18 (1H, s), 8.77 (1H, s)

Reference Example 12

Tert-butyl N-(2,3-dihydro-2,2,6,7-tetramethyl-1-benzofuran-5-yl)carbamate

To a suspension of 2,3-dihydro-2,2,6,7-tetramethyl-1-benzofuran-5-amine hydrochloride (0.49 g, 2.2 mmol) in THF (5 mL) was added 2N aqueous sodium hydroxide solution (1.1 mL, 2.2 mmol), and the mixture was vigorously stirred under the nitrogen atmosphere. After the crystals were dissolved, di-tert-butyl dicarbonate (0.51 g, 2.3 mmol) was added, and the mixture was stirred at room temperature for 2.5 hours. Ethyl acetate was added to the reaction mixture, the mixture was washed with water and saturated brine, dried over magnesium sulfate, filtered, and concentrated under reduced pressure. The residue was recrystallized from diisopropyl ether-hexane to obtain 0.51 g of the title compound.

Yield 80% mp. 134–134° C.

$^1$H-NMR (CDCl$_3$) δ 1.44 (6H, s), 1.50 (9H, s), 2.11 (6H, s), 2.97 (2H, s), 6.02 (1H, br s), 7.12 (1H, br s)

Reference Example 13

Tert-butyl N-[2,3-dihydro-2-(iodomethyl)-2,6,7-trimethyl-benzofuran-5-yl]carbamate To a solution of N-[4-hydroxy-2,3-dimethyl-5-)2-methyl-2-propenyl)phenyl]formamide (11.6 g, 52.9 mmol) in dichloromethane (90 mL) and methanol (90 mL) was added calcium carbonate (7.51 g, 75.0 mmol). To this suspension was added benzyltrimethylammonium dichloroiodate (20.1 g, 57.8 mmol) in small portions under ice-cooling, and the mixture was stirred at the same temperature for 5 minutes and at room temperature for 15 minutes under the nitrogen atmosphere. The reaction mixture was filtered, and concentrated under reduced pressure. To the residue was added a 5% aqueous solution of sodium hydrogen sulfite (150 mL), and the mixture was extracted with ethyl acetate three times. The combined organic layers were washed with water and saturated brine, dried over magnesium sulfate, treated with active carbon, filtered, concentrated under reduced pressure. The residue was dissolved in methanol (90 mL), 2N hydrochloric acid (90 mL), and the mixture was heated to reflux for 45 minutes under the nitrogen atmosphere. The reaction mixture was added dropwise to a suspension of sodium bicarbonate (20 g, 0.24 mol) in water (100 mL)ethyl acetate (100 mL) to neutralize, the organic layer was separated, and the aqueous layer was extracted with ethyl acetate two times. The combined organic layers were washed with water and saturated brine, dried over magnesium sulfate, treated with active carbon, and filtered. The resulting solution was concentrated to about 100 mL under reduced pressure, di-tert-butyl dicarbonate (12.7 g, 58.2 mmol) was added, and the mixture was stirred at room temperature for 2.5 hours under the nitrogen atmosphere. The reaction mixture was concentrated under reduced pressure, the residue was subjected to silica gel column chromatography (hexane-ethyl acetate 10:1), and recrystallized from ethyl acetate-hexane to obtain 15.8 g of the title compound.

Yield 72% mp. 145–148° C.

$^1$H-NMR (CDCl$_3$) δ 1.50 (9H, s), 1.64 (3H, s), 2.12 (6H, s), 3.03 (1H, d, J=15.9 Hz), 3.29 (1H, d, J=15.9 Hz), 3.40 (2H, s), 6.03 (1H, br s), 7.14 (1H, br s)

Reference Example 14

N-(2,3-Dimethylphenyl)-2,2,2-trifluoroacetamide

To a solution of 2,3-dimethylaniline (25.3 g, 0.21 mol) and triethylamine (25.3 g, 0.25 mol) in THF (250 mL) was added dropwise trifluoroacetic anhydride (33 mL, 0.23 mol) over 10 minutes under ice-cooling, and the mixture was stirred at the same temperature for 10 minutes. Water was added to the reaction mixture, and the mixture was extracted with diisopropyl ether two times. The combined organic layers were washed with water and saturated brine, dried over magnesium sulfate, treated with active carbon, filtered, concentrated under reduced pressure. The residue was recrystallized from diisopropyl ether-hexane to obtain 42.2 g of the title compound.

Yield 93% mp. 102–103° C.

$^1$H-NMR (CDCl$_3$) δ 2.17 (3H, s), 2.32 (3H, s), 7.08–7.21 (2H, m), 7.42–7.50 (1H, m), 7.50–8.00 (1H, br)

Reference Example 15

2,3-Dimethyl-N-(2-methyl-2-propenyl)benzeneamine

To a solution of N-(2,3-dimethylphenyl)-2,2,2-trifluoroacetamide (6.53 g, 30.1 mmol) in acetone (50 mL) were added potassium iodide (4.99 g, 30.1 mmol), 3-chloro-2-methyl-1-propene (8.9 mL, 90 mmol) and crushed 85% potassium hydroxide (5.8 g, 88 mmol), and the mixture was heated to reflux for 80 minutes. Water was added to the reaction mixture, and the mixture was extracted with hexane two times. The combined organic layers were washed with water and saturated brine, dried over magnesium sulfate, filtered, and concentrated under reduced pressure. The residue was subjected to silica gel column chromatography (hexane-ethyl acetate 100:1 then 30:1) to obtain 4.67 g of the title compound.

Yield 89%
Oil
$^1$H-NMR(CDCl$_3$) δ 1.80 (3H, d, J=0.8 Hz), 2.08 (3H, s), 2.28 (3H, s), 3.72 (2H, s), 4.86–5.02 (2H, m), 6.47 (1H, d, J=7.9 Hz), 6.58 (1H, d, J=7.9 Hz), 7.00 (1H, t, J=7.9 Hz)

Reference Example 16

2,3-Dihydro-2,2,6,7-tetramethyl 1H-indole

To a solution of 2,3-dimethyl-N-(2-methyl-2-propenyl) benzeneamine (3.77 g, 21.5 mmol) in xylene (35 mL) was added zinc chloride (8.80 g, 64.6 mmol), and the mixture was stirred at 150° C. for 3.5 hours. Heating was stopped, and a solution of sodium acetate (10.6 g, 0.129 mol) in water (30 mL) was carefully added dropwise to the resulting hot mixture. The resulting solution was cooled, the organic layer was separated, and the aqueous layer was extracted with toluene. The combined organic layers were washed with water and saturated brine, dried over magnesium sulfate, filtered and concentrated under reduced pressure. The residue was subjected to silica gel column chromatography (hexane-ethyl acetate 20:1) to obtain 2.91 g of the title compound.

Yield 77%
Oil
$^1$H-NMR (CDCl$_3$) δ 1.33 (6H, s), 2.02 (3H, s), 2.21 (3H, s), 2.60–4.00 (1H, br), 2.85 (2H, s), 6.55 (1H, d, J=7.3 Hz), 6.82 (1H, d, J=7.3 Hz).

Reference Example 17

2,3-Dihydro-5-hydroxy-2,2,6,7-tetramethyl-1H-indole-1-carbaldehyde

To a solution of 65% potassium nitrosodisulfonate (14.4 g, 34.9 mmol) in pH 6.86 phosphate buffer (460 mL) was added a solution of 2,3-dihydro-2,2,6,7-tetramethyl-1H-indole (2.91 g, 14.6 mmol) in methanol (80 mL), and the mixture was stirred at room temperature for 15 minutes. The reaction mixture was extracted with ethyl acetate three times, and the combined organic layers were washed with water. This solution was mixed with a solution of sodium hydrosulfite (6.36 g, 36.5 mmol) in water (75 mL), the mixture was shaken, and the aqueous layer was separated. The organic layer was washed with saturated brine, dried over magnesium sulfate, filtered, and concentrated under reduced pressure. The residue was dissolved in formic acid (5 mL), a solution of acetic anhydride (3.2 mL, 34 mmol) in formic acid (5 mL) (which had been stirred at room temperature for 20 minutes in advance) was added dropwise, and the mixture was stirred at room temperature for 1 hour. The reaction mixture was concentrated under reduce pressure, neutralized with an aqueous saturated solution of sodium bicarbonate, and extracted with chloroform three times. The combined organic layers were washed with water, and concentrated under reduced pressure. The residue was dissolved in methanol (30 mL) and chloroform (15 mL), a 1N aqueous solution of sodium hydroxide was added under ice-cooling. and the mixture was stirred at the same temperature for 10 minutes. The reaction mixture was neutralized with 1N hydrochloric acid, and the mixture was extracted with chloroform three times. The combined organic layers were washed with water and saturated brine, dried over magnesium sulfate, filtered, and concentrated under reduced pressure. The residue was recrystallized from ethanol-diisopropyl ether to obtain 1.48 g of the title compound.

Yield 41%
mp. 202–204° C.
$^1$H-NMR (CDCl$_3$) δ 1.51 (3H, s), 1.61, 1.66 (3H, s), 2.16 (3H, s), 2.18, 2.30 (3H, s), 2.82, 2.88 (2H, s), 5.32, 5.47 (1H, br, s), 6.55 (1H, s), 8.33, 8.84 (1H, s).

Reference Example 18

2,3-Dihydro-5-hydroxy-2,2,6,7-tetramethyl-4-(2-methyl-2-propenyl)-1H-indole-1-carbaldehyde A suspension of 2,3-dihydro-5-hydroxy-2,2,6,7-tetramethyl-1H-indole-1-carbaldehyde (1.86 g, 8.5 mmol) in N,N-dimethylformamide (10 mL) was added to a 66% dispersion of sodium hydride in an oil (0.37 g, 10 mol), and the mixture was stirred at room temperature for 5 minutes under the nitrogen atmosphere. To the mixture was added 3-chloro-2-methyl-1-propene (1.1 mL, 11 mmol), and the mixture was stirred at room temperature for 10 minutes and at 60° C. for 10 minutes under the nitrogen atmosphere. The reaction mixture was poured into an aqueous saturated solution of ammonium chloride, and extracted with ethyl acetate two times. The combined organic layers were washed with water and saturated brine, dried over magnesium sulfate, filtered, and concentrated under reduced pressure to obtain 2.51 g of an oil. This was dissolved in N,N-diethylaniline (5 mL), and the mixture was stirred at 200° C. for 8 hours under the nitrogen atmosphere. The reaction mixture was cooled, hexane was added to crystallize, which was recrystallized from ethanol-hexane to obtain 1.71 g of the title compound.

Yield 74%
mp. 116–118° C.
$^1$H-NMR (CDCl$_3$) δ 1.52 (3H, s), 1.61 (3H, s), 1.73, 1.75 (3H, s), 2.15, 2.29 (3H, s), 2.18 (3H, s), 2.81, 2.86 (2H, s), 3.28 (2H, s), 4.79 (1H, br s), 4.89, 4.91 (1H, s), 5.06, 5.08 (1H, s), 8.34, 8.84 (1H, s).

Reference Example 19

N-methyl-N-(4-piperidinyl)-1,3-benzothiazole-2-amine hydrochloride

To a suspension of ethyl 4-[methyl[(phenylamino)thioxomethyl]amino]-1-piperidinecarboxylate (4.02 g, 12.5 mmol) in carbon tetrachloride (25 mL) was added dropwise a solution of bromine (2.00 g, 12.5 mmol) in carbon tetrachloride (10 mL), the mixture was stirred at room temperature for 30 minutes, and heated to reflux for 1 hours. The insolubles were filtered, and washed with hexane. This was dissolved in 48% hydrobromic acid (40 mL), and the solution was heated to reflux for 2 hours. The reaction mixture was ice-cooled, neutralized with 25% aqueous ammonia, and extracted with ethyl acetate two times. The combined organic layers were washed with water and saturated brine, dried over magnesium sulfate, filtered, and concentrated under reduced pressure. To the residue was added diisopropyl ether, the insolubles were filtered, and the filtrate was concentrated under reduced pressure. The residue was dissolved in methanol, a 10% hydrogen chloride-methanol solution (11 mL), and the mixture was concentrated under reduced pressure. The residue was recrystallized from methanol-diisopropyl ether to obtain 2.53 g of the title compound.

Yield 71% mp. 287–289° C.

$^1$H-NMR (DMSO-d$_6$) δ 1.80–2.00 (2H, m), 2.00–2.29 (2H, m), 2.91–3.26 (2H, m), 3.04 (3H, s), 3.28–3.47 (2H, m), 4.364.58 (1H, m), 7.04–7.17 (1H, m), 7.26–7.37 (1H, m), 7.50 (1H, d, J=8.0 Hz), 7.81 (1H, d, J=8.0 Hz), 9.11 (2H, br s)

Reference Example 20

4-Methoxy-2,3-dimethylaniline

4-Methoxy-2,3-dimethylnitrobenzene (21.1 g, 0.15 mol) was dissolved in ethanol (300 mL), and 10% palladium carbon (50% hydrate, 1.36 g) was added. The mixture was reacted at 40° C. for 2 hours under the hydrogen atmosphere. After cooling, the catalyst was removed, ethanol was distilled off under reduced pressure, and the residue was diluted with ethyl acetate. The dilution was washed with 5% sodium hydrosulfite, dried over sodium sulfate, and purified by small amount silica gel column chromatography (ethyl acetate, 1:1). The solvent was distilled off under reduced pressure, followed by recrystallization from hexane, to obtain 15.8 g of the title compound.

Yield 70%

$^1$H-NMR (CDCl$_3$) δ 2.10 (3H, s), 2.17 (3H, s), 2.95 (2H, br), 3.75 (3H, s), 6.53 (1H, d, J=8.6 Hz), 6.62 (1H, d, J=8.6 Hz)

Reference Example 21

6,7-Dimethyl-5-methoxy-3-(methylthio)-1,3-dihydro-2H-indole-2-one

To a solution of methyl (methylthio)acetate (40.8 mL, 317 mmol) in dichloromethane (1100 mL) was added sulfuryl chloride (26.6 mL, 331 mmol) at –78° C., and the mixture was stirred for 15 minutes. Further, a solution of 4-methoxy-2,3-dimethylaniline (41.7 g, 276 mmol) and proton sponge (62.1 g, 290 mmol) in dichloromethane (200 mL) was added dropwise over 1 hour and mixture was stirred at the same temperature for 1 hour. Triethylamine (43 mL, 380 mmol) was added, and the temperature was gradually raised to room temperature. After stirring at room temperature for 2 hours, water was added, the organic layer was washed with an aqueous saturated solution of sodium bicarbonate and saturated brine, dried over sodium sulfate, and the solvent was distilled off under reduced pressure. To the residue was added toluene (300 mL), and the mixture was stirred at reflux for 1 hour. The solvent was distilled off under reduced pressure, which was recrystallized from ethyl acetate to obtain 30.0 g of the title compound.

Yield 46%

$^1$H-NMR (CDCl$_3$) δ 2.03 (3H, s), 2.12 (3H, s), 2.19 (3H, s), 3.82 (3H, s), 4.27 (1H, s), 6.82 (1H, s), 8.85 (1H, brs)

Reference Example 22

6,7-Dimethyl-5-methoxy-1,3-dihydro-2H-indole-2-one

To a solution of 6,7-dimethyl-5-methoxy-3(methylthio)-1,3-dihydro-2H-indole-2-one (30 g, 126 mmol) in dichloromethane (600 mL) were added triphenylphosphine (40 g, 153 mmol) and toluenesulfonic acid monohydrate (29 g, 153 mmol) at room temperature, and the mixture was stirred for 3 hours. The reaction solution was poured into cool water, and the precipitated crystals were filtered. The crystals were washed with dichloromethane and water to obtain 17.5 g of the title compound.

Yield 72%

$^1$H-NMR (DMSO-d$_6$) δ 2.05 (3H, s), 2.10 (3H, s), 3.37 (1H, br), 3.42 (2H, s), 3.70 (3H, s), 6.76 (1H, s)

Reference Example 23

6,7-Dimethyl-5-methoxy-1,2-dihydro-1H-indole

To a solution of 6,7-dimethyl-5-methoxy-1,3-dihydro-2H-indole-2-one (17.5 g, 91.5 mmol) in THF (500 mL) was added dropwise 1M-borane THF complex salt (306 mmol) at 0° C., and the mixture was stirred at 60° C. 3 hours. After ice-cooling, the mixture was added dropwise to water (100 mL). THF was distilled off under reduced pressure, concentrated hydrochloric acid (100 mL) was added, and the mixture was stirred under reflux for 2 hours. After neutralizing with 12N sodium hydroxide under ice-cooling, the mixture was extracted with ethyl acetate. The organic layer was washed with saturated brine, dried over sodium sulfate, and purified by small amount silica gel column chromatography (ethyl acetate). The solvent was distilled off under reduced pressure, followed by recrystallization from hexane, to obtain 8.18 g of the title compound.

Yield 66% mp. 54–56° C.

$^1$H-NMR (CDCl$_3$) δ 2.07 (3H, s), 2.12 (3H, s), 3.03 (2H, t, J=8.3 Hz), 3.53 (2H, t, J=8.3 Hz), 3.76 (3H, s), 6.65 (1H, s).

Reference Example 24

1-Methoxycarbonyl-6,7-dimethyl-5-methoxy-1,2-dihydro-1H-indole

To a solution of 6,7-dimethyl-5-methoxy-1,2-dihydro-1H-indole (2,7 g, 15.2 mmol) in ethyl acetate (30 mL) were added potassium carbonate (4.3 g, 31 mmol) and water (30 mL), and methyl chlorocarbonate (1.5 mL, 19.4 mmol) was added dropwise at 0° C. The mixture was stirred at room temperature for 1 hour. The organic layer was washed with saturated brine, dried over sodium sulfate, and purified by small amount silica gel column chromatography (hexane-ethyl acetate, 1:1). The solvent was distilled off under reduced pressure to obtain 3.5 g of the title compound as an oil.

Yield 98%

$^1$H-NMR (CDCl$_3$) δ 2.15 (6H, s), 2.95 (2H, t, J=8.5 Hz), 3.77 (3H, s), 3.79 (3H, s), 4.11 (2H, t, J=8.5 Hz), 6.65 (1H, s).

Reference Example 25

4-Bromo-1-methoxycarbonyl-6,7-dimethyl-5-methoxy-1,2-dihydro-1H-indole

A solution of 1-methoxycarbonyl-6,7-dimethyl-5-methoxy-1,2-dihydro-1H-indole (3.2 g, 13.6 mmol) in acetic acid (16 mL) was added dropwise to bromine (0.9 mL, 17.5 mmol) at 10° C. The mixture was stirred at room temperature for 30 minutes. The reaction solution was concentrated under reduced pressure, to the residue was added a 5% aqueous solution of sodium sulfite, and the mixture was extracted with ethyl acetate. The organic layer was washed with an aqueous saturated solution of sodium bicarbonate and saturated brine, dried over sodium sulfate, and concentrated under reduced pressure. The residue was purified with silica gel column chromatography (hexane-ethyl acetate, 10:1). The solvent was distilled off under reduced pressure to obtain 3.4 g of the title compound as an oil.

Yield 81%

$^1$H-NMR (CDCl$_3$) δ 2.10 (3H, s), 2.25 (3H, s), 2.98 (2H, t, J=7.6 Hz), 3.75 (3H, s), 3.79 (3H, s), 4.12 (2H, t, J=7.6 Hz)

Reference Example 26

1-(Tert-butoxycarbonyl)-6,7-dimethyl-5-methoxy-1,2-dihydro-1H-indole

To a solution of 6,7-dimethyl-5-methoxy-1,2-dihydro-1H-indole (2.0 g, 11.3 mmol) in THF (20 mL) were added triethylamine (2.4 mL, 17.2 mmol) and di-tert-butyl dicarbonate (2.68 g, 12.3 mmol) at 0° C. After stirring at room temperature for 1 hour, the solvent was distilled off under reduced pressure, followed by recrystallization from hexane to obtain 2.27 g of the title compound.

Yield 73% mp. 124–128° C.

$^1$H-NMR (CDCl$_3$) δ 1.51 (9H, s), 2.13 (3H, s), 2.16 (3H, s), 2.93 (2H, t, J=7.3 Hz), 3.78 (3H, s), 4.07 (2H, t, J=7.3 Hz), 6.64 (1H, s)

Reference Example 27

4-Bromo-1-(tert-butoxycarbonate)-6,7-dimethyl-5-methoxy-1,2-dihydro-1H-indole

To a solution of 1-(tert-butoxycarbonyl)-6,7-dimethyl-5-methoxy-1,2-dihydro-1H-indole (2.00 g, 7.2 mmol) in acetic acid (16 mL) was added sodium acetate (0.89 g, 10.8 mmol), and bromine (0.42 mL, 8.2 mmol) was added dropwise at room temperature. After stirred for 1 hour, the reaction solution was concentrated under reduced pressure, to the residue was added a 5% aqueous solution of sodium sulfite, and the mixture was extracted with ethyl acetate. The organic layer was washed with an aqueous saturated solution of sodium bicarbonate and saturated brine, dried over sodium sulfate, and concentrated under reduced pressure. The residue was purified by silica gel column chromatography (hexane-ethyl acetate 10:1). The solvent was distilled off under reduce pressure to obtain 1.61 g of the title compound as an oil.

Yield 71%

$^1$H-NMR (CDCl$_3$) δ 1.51 (9H, s), 2.10 (3H, s), 2.23 (3H, s), 2.96 (2H, t, J=7.6 Hz), 3.74 (3H, s), 4.07 (2H, t, J=7.3 Hz)

Example 1

1,6,7,8-Tetrahydro-2,2,4,5-tetramethyl-2H-furo[3,2-e]indole

To a solution of 2,3-dihydro-5-hydroxy-6,7-dimethyl-4-(2-methyl-2-propenyl)-1H-indole-1-carbaldehyde (1.23 g, 5.0 mmol) in methanol (4 mL) was added concentrated hydrochloric acid (2 mL)-methanol (1 mL) solution, and the mixture was heated to reflux for 2 hours under the nitrogen atmosphere. The reaction mixture was added to a mixture of sodium bicarbonate (3.02 g, 35.9 mmol) in water (10 mL)-ethyl acetate (10 mL) to neutralize, the organic layer was separated, and the aqueous layer was extracted with ethyl acetate. The combined organic layers were washed with saturated brine, dried over magnesium sulfate, treated with active carbon, filtered, and concentrated under reduced pressure. The residue was recrystallized from ethyl acetate-hexane to obtain 497 mg of the title compound.

Yield 46% mp. 107–109° C.

$^1$H-NMR (CDCl$_3$) δ 1.45 (6H, s), 2.04 (3H, s), 2.08 (3H, s), 2.2–2.7 (1H, br), 2.8–3.0 (2H, m), 2.89 (2H, s), 3.54 (2H, t, J=8.2 Hz)

Example 2

1,6,7,8-Tetrahydro-2,2,4,5,7-pentamethyl-2H-furo[3,2-e]indole hydrochloride

To a solution of 2,3-dihydro-5-hydroxy-2,6,7-trimethyl-4-(2-methyl-2-propen-1-yl)-1H-indole-1 carbaldehyde (0.26 g, 1.0 mmol) in ethanol (3 mL) was added concentrated hydrochloric acid (0.5 mL), and the mixture was heated to reflux for 1 hour. The reaction mixture was treated with active carbon, filtered, and concentrated under reducer pressure. The residue was recrystallized from ethanol-diethyl ether to obtain 0.14 g of the title compound.

Yield 52% mp. 204–208° C.

$^1$H-NMR (CDCl$_3$) δ 1.47 (6H, s), 1.82 (3H, d, J=6.2 Hz), 2.08 (3H, s), 2.50 (3H, s), 2.7–2.9 (1H, m), 3.24 (1H, dd, i=16.0, 7.8 Hz), 4.3–4.5 (1H, m), 10.7–11.1 (1H, m), 11.4–11.7 (1H, m)

Example 3

1,6,7,8-Tetrahydro-2, 2,4,5,7,7-hexamethyl-2H-furo[3,2-e]indole oxalate

To a solution of tert-butyl N-(2,3-dihydro-2,2,6,7-tetramethyl-1-benzofuran-5-yl)carbamate (0.50 g, 1.7 mmol) in N,N-dimethylformamide was added a 66% dispersion of sodium hydride in an oil (83 mg, 2.3 mmol), and the mixture was stirred at room temperature for 15 minutes under the nitrogen atmosphere. To this was added dropwise 3-chloro-2-methyl-1-propene (0.28 mL, 2.8 mmol), and the mixture was stirred at room temperature for 15 minutes. Water was added to the reaction mixture, and the mixture was extracted with ethyl acetate two times. The combined organic layers were washed with water and saturated brine, dried over magnesium sulfate, filtered, and concentrated under reduced pressure to obtain 637 mg of an oil. To this 470 mg was added 10% hydrogen chloride-methanol solution (3 mL), and the mixture was stirred at 50° C. for 40 minutes under the nitrogen atmosphere. The reaction mixture was concentrated under reduced pressure, an aqueous saturated solution of sodium bicarbonate was added to neutralize, and the mixture was extracted with ethyl acetate two times. The combined organic layers were washed with water and saturated brine, dried over magnesium sulfate, filtered, and concentrated under reduced pressure to obtain 350 mg of an oil. This 295 mg was dissolved in xylene (1.5 mL), zinc chloride (0.48 g, 3.5 mmol) was added, and the mixture was heated to reflux for 2 hours under the nitrogen atmosphere. To the reaction mixture was added a 5N aqueous solution of sodium hydroxide (2 mL, 10 mmol), and the mixture was extracted with xylene two times. The combined organic layers were washed with water and saturated brine, dried over magnesium sulfate, filtered, and concentrated under reduced pressure. The residue was subjected to silica gel column chromatography (hexane-ethyl acetate 10:1) to obtain 216 mg of the solid. This 164 mg was dissolved in ethanol (1 mL), and a solution of oxalic acid (60 mg, 0.67 mmol) in ethanol (1 mL) was added. To this solution was added diethyl ether to crystallize to obtain 180 mg of the title compound.

Yield 67% mp. 223–230° C. (Sublimation)

$^1$H-NMR (DMSO-$d_6$) δ 1.33 (6H, s), 1.37 (6H, s), 1.96 (3H, s), 1.98 (3H, s), 2.72 (2H, s), 2.84 (2H, s)

Example 4

1,6,7,8-Tetrahydro-2-(iodomethyl)-2,4,5-trimethyl-2H-furo[3,2-e]indole-6-carbaldehyde To a suspension of 2,3-dihydro-5-hydroxy-6,7-dimethyl-4-(2-methyl-2-propenyl)-1H-indole-1-carbaldehyde (4.91 g, 20.0 mmol) in dichloromethane (10 mL) and methanol (20 mL) was added calcium carbonate (2.60 g, 26.0 mmol), the mixture was ice-cooled, a solution of benzyltrimethylammonium dichloroiodate (7.66 g, 22.0 mmol) in dichloromethane (20 mL) was added dropwise over 10 minutes under nitrogen atmosphere, and the mixture was stirred at room temperature for 30 minutes. The reaction mixture was filtered, and concentrated under reduced pressure. To the residue was added a solution of sodium hydrogen sulfite (2.50 g) in water (50 mL), and the mixture was extracted with ethyl acetate three times. The combined organic layers were washed with water and saturated brine, dried over magnesium sulfate, filtered, and concentrated under reduced pressure. The residue was subjected to silica gel column chromatography (hexane-ethyl acetate 5;1 then 2:1), and recrystallized from ethyl acetate-diisopropyl ether to obtain 4.34 g of the title compound.

Yield 58% mp. 102–103° C.

$^1$H-NMR (CDCl$_3$) δ 1.67 (3H, s), 2.14 (3H, s), 2.29 (3H, s), 2.90 (2H, t, J=7.7 Hz), 2.96 (1H, d, J=15.9 Hz), 3.23 (1H, d, J=15.9 Hz), 3.43 (2H, s), 4.14 (2H, t, J=7.7 Hz), 8.15 (1H, s)

Example 5

1,6,7,8-Tetrahydro-2-(iodomethyl)-2,4,5-trimethyl-2H-furo[3,2-e]indole

To a solution of 1,6,7 8-tetrahydro-2-(iodomethyl)-2,4,5-trimethyl-2H-furo[3,2-e]indole-6-carbaldehyde (7.95 g, 21.4 mmol) in methanol (25 mL) was added 2N hydrochloric acid (25 mL), and the mixture was heated to reflux for 1 hour under the nitrogen atmosphere. The reaction mixture was added dropwise to a mixture of sodium dicarbonate (6.3 g, 75 mmol) in water (25 mL)ethyl acetate (25 mL) to neutralize, which was extracted with ethyl acetate two times. The combined organic layers were washed with water and saturated brine, dried over sodium sulfated, filtered, and concentrated under reduced pressure. The residue was subjected to silica gel column chromatography (hexane-ethyl acetate 1:1), and crystallized from diisopropyl ether-hexane to obtain 6.39 g of the title compound.

Yield 87% mp. 97–98° C.

$^1$H-NMR (CDCl$_3$) δ 1.65 (3H, s), 2.03 (3H, s), 2.08 (3H, s), 2.92 (2H, t, J=8.3 Hz), 2.94 (1H, d, J=15.5 Hz), 3.21 (1H, d, J=15.5 Hz), 3.41 (2H, s), 3.55 (2H, t, J=8.3 Hz)

Example 6

1,6,7,8-Tetrahydro-2-(iodomethyl)-2,4,5,7,7-pentamethyl-2H-furo[3,2-e]indole-6-carbaldehyde To a solution of 2,3-dihydro-5-hydroxy-2,2,6,7-tetramethyl-4-(2-methyl-2-propenyl)-1H-indole-1-carbaldehyde (1.60 g, 5.85 mmol) in dichloromethane (15 mL) and methanol (5 mL) were added calcium carbonate (0.76 g, 7.6 mmol) and benzyltrimethylammonium dichloroiodate (2.24 g, 6.44 mmol), and the mixture was stirred at room temperature for 15 minutes. The reaction mixture was filtered and concentrated under reduced pressure. To the residue was added a 5% aqueous sodium hydrogen sulfite solution (15 mL), and the mixture was extracted with ethyl acetate two times. The combined organic layers were washed with water and saturated brine, dried over magnesium sulfate, filtered, and concentrated under reduced pressure. The residue was subjected to basic silica gel column chromatography (hexane-ethyl acetate 10:1) to obtain 1.93 g of the title compound.

Yield 83%

Oil $^1$H-NMR (CDCl$_3$) δ 1.47–1.70 (9H, m), 2.12, 2.26 (6H, s), 2.76, 2.81 (2H, s), 2.92 (1H, d, J=16.2 Hz), 3.20 (1H, d, J=16.2 Hz), 3.42 (2H, s), 8.34, 8.85 (1H, s)

Example 7

1,6,7,8-Tetrahydro-2-(iodomethyl)-2,4,5,7,7-pentamethyl-2H-furo[3,2-e]indole

To a solution of 1,6,7,8-tetrahydro-2-(iodomethyl)-2,4,5,7,7-pentamethyl-2H-furo[3,2-e]indole-6-carbaldehyde (1.93 g, 4.83 mmol) in methanol (10 mL) was added concentrated hydrochloric acid (3 mL), and the mixture was heated to reflux for 3 hours under the nitrogen atmosphere. The reaction mixture was added dropwise to a mixture of sodium bicarbonate (3.7 g, 44 mmol) in water-ethyl acetate to neutralize, which was extracted with ethyl acetate two times. The combined organic layers were washed with water and saturated brine, dried over magnesium sulfate, filtered and concentrated under reduced pressure. The residue was subjected to silica gel column chromatography (hexane-ethyl acetate 10:1) to obtain 1.56 g of the title compound.

Yield 87%

Amorphous $^1$H-NMR (CDCl$_3$) δ 1.34 (6H, s), 1.64 (3H, s), 1.70–2.70 (1H, br), 2.00 (3H, s), 2.07 (3H, s), 2.75 (2H, s), 2.90 (1H, d, J=15.8 Hz), 3.16 (1H, d, J=15.8 Hz), 3.41 (2H, s)

Example 8

1,6,7,8-Tetrahydro-2,4,5-trimethyl-2-[(4-phenylpiperidino)methyl]-2H-furo[3,2-e]indole fumarate A suspension of 1,6,7,8-tetrahydro-2-(iodomethyl)-2,4,5-trimethyl-2H-furo[3,2-e]indole (2.06 g, 6.00 mmol), 4-phenylpiperidine (1.96 g, 12.2 mmol) and potassium carbonate (1.66 g, 12.0 mmol) in N,N-dimethylacetamide (20 mL) was heated to reflux for 2.5 hours under the nitrogen atmosphere. Water was added to the reaction mixture, and the mixture was extracted with ethyl acetate two times. The combined organic layers were washed with water and saturated brine, dried over magnesium sulfate, filtered, concentrated under reduced pressure. The residue was subjected to silica gel column chromatography (hexane-ethyl acetate-triethylamine 20:10:1) and crystallized from diisopropyl ether-hexane to obtain 1.55 g of a free base. Yield 69%. This 377 mg (1.00 mmol) was dissolved in methanol (2.5 mL), a solution of fumaric acid (116 mg, 0.999 mmol) in methanol (1 mL) was added, and concentrated under reduced pressure. The residue was crystallized from methanol to obtain 286 mg of the title compound.

Yield 58% mp. 202–204° C. (dec.)

$^1$H-NMR (DMSO-d$_6$) δ 1.35 (3H, s), 1.5–1.8 (4H, m), 1.92 (6H, s), 2.1–2.6 (3H, m), 2.57 (2H, s), 2.6–2.9 (3H, m), 2.93.1 (1H, m), 3.03 (1H, d, J=15.4 Hz), 3.1–3.3 (1H, m), 3.36 (2H, t, J=8.2 Hz), 6.61 (2H, s), 7.1–7.4 (5H, m)

Example 9

1,6,7,8-Tetrahydro-2,4,5,7,7-pentamethyl-2-[(4-phenylpiperidino)methyl]-2H-furo[3,2-e]indole dihydrochloride To a solution of tert-butyl [2,3-dihydro-2(iodomethyl)-2,6,7-trimethyl-1-benzofuran-5-yl]carbamate (2.92 g, 7.00 mmol) in DMF (20 mL) was added a 66% dispersion of sodium hydride in an oil (0.28 g, 7.7 mmol) under ice-cooling, and the mixture was stirred at the same temperature for 10 minutes under the nitrogen atmosphere. To this was added dropwise 3-chloro-2-methyl-1-propene (0.90 mL, 9.1 mmol), and the mixture was stirred at the same temperature for 1 hour under the nitrogen atmosphere. Water was added to the reaction mixture, and the mixture was extracted with ethyl acetate two times. The combined organic layers were washed with water and saturated brine, dried over magnesium sulfate, filtered, and concentrated under reduced pressure to obtain 3.68 g of an oil. This 3.57 g was dissolved in a 10% hydrogen chloride-methanol solution (15 mL), and the mixture was stirred at 50° C. for 80 minutes. The reaction mixture was added dropwise to a mixture of sodium bicarbonate (5.1 g, 61 mmol) in water-ethyl acetate to neutralize, which was extracted with ethyl acetate two times. The combined organic layers were washed with water and saturated brine, dried over magnesium sulfate, filtered, and concentrated under reduced pressure to obtain 2.92 g of an oil. This was dissolved in xylene (15 mL), zinc chloride (2.77 g, 29.3 mmol) was added, and the mixture was heated to reflux for 1 hour under the nitrogen atmosphere. The reaction mixture was cooled, a 5N aqueous sodium hydroxide solution (10 mL, 50 mmol) was added, diluted with water, the insolubles were filtered, and extracted with xylene three times. The combined organic layers were washed with water and saturated brine, dried over magnesium sulfate, filtered, and concentrated under reduced pressure. The residue was subjected to silica gel column chromatography (hexane-ethyl acetate 20:1 then 10:1) to obtain 1.24 g of an oil. This was dissolved in N,N-dimethylacetamide (10 mL), 4-phenylpiperidine (0.65 g, 4.0 mmol) and potassium carbonate (0.56 g, 4.1 mmol) were added, and the mixture was stirred at 170° C. for 3 hours under the nitrogen atmosphere. Water was added to the reaction mixture, and the mixture was extracted with ethyl acetate three times. The combined organic layers were washed with water, and extracted with a 5% aqueous acetic acid solution two times and with a 5% aqueous formic acid solution two times. The combined aqueous layers were neutralized with sodium bicarbonate, which was extracted with ethyl acetate. The combined organic layers were washed with water and saturated brine, dried over magnesium sulfate, filtered, and concentrated under reduced pressure. The residue was subjected to silica gel column chromatography (hexane-ethyl acetate 10:1) to obtain 664 mg of a free base. Yield 24%. This was dissolved in methanol, a 10% hydrogen chloride-methanol solution was added, and the mixture was concentrated under reduced pressure. The residue was crystallized from ethanol-diethyl ether to obtain 606 mg of the title compound.

Yield 77% mp. 175–181° C.

$^1$H-NMR (DMSO-d$_6$) δ 1.55 (3H, s), 1.56 (3H, s), 1.64 (3H, s), 1.8–2.5 (5H, m), 2.08 (3H, s), 2.25 (3H, s), 2.6–4.0 (8H, m), 2.95 (2H, s), 7.1–7.5 (5H, m), 10.3–10.6 (1H, br), 10.7–11.5 (2H, br).

Example 10

1,6,7,8-Tetrahydro-2,4,5,7,7-pentamethyl-2-(1,2,4,5-tetrahydro-3H-benzazepine-3-ylmethyl)-2H-furo[3,2-e] indole hydrochloride A suspension of 1,6,7,8-tetrahydro-2-(iodomethyl)-2,4,5,7,7-pentamethyl-2H-furo[3,2-e]indole (520 mg, 1.40 mmol), 2,3,4,5-tetrahydro-1H-3-benzazepine (309 mg, 2.10 mmol) and potassium carbonate (387 mg, 2.80 mmol) in N,N-dimethylacetamide (3 mL) was stirred at 180° C. for 3 hours under the nitrogen atmosphere. Water was added to the reaction mixture, and the mixture was extracted with ethyl acetate two times, The combined organic layers were washed with water and saturated brine, dried over magnesium sulfate, filtered, and concentrated under reduced pressure. The residue was subjected to basic silica gel column chromatography (hexane-ethyl acetate 10:1) to obtain an oil. This was dissolved in methanol, a 10% hydrogen chloride-methanol solution was added to obtain 464 mg of the title compound.

Yield 78% Amorphous $^1$H-NMR (DMSO-d$_6$) δ 1.35 (6H, br, s), 1.61 (3H, s), 2.02 (6H, s), 2.50–3.88 (14H, m), 7.16 (4H, br s)

Example 11

N-(Diphenylmethyl)-1-[(1,6,7,8-tetrahydro-2,4,5,7,7-pentamethyl-2H-furo[3,2-e]indol-2-yl)methyl]-4-piperidineamine dihydrochloride Using a method similar to that for Example 10, the title compound was synthesized from 1,6,7,8-tetrahydro-2(iodomethyl)-2,4,5,7,7-pentamethyl-2H-furo[3,2-e]indole and N-(diphenylmethyl)-4-piperidineamine.

Yield 87%

Amorphous $^1$H-NMR (DMSO-d$_6$) δ 1.20–2.30 (4H, m), 1.35 (9H, br s), 1.96 (3H, s), 2.03 (3H, s), 2.37–3.62 (1H, m), 5.63 (1H, br s), 7.12–7.60 (6H, m), 7.60–8.00 (4H, m)

Example 12

1,6,7,8-Tetrahydro-2,4,5-trimethyl-2-[[4-[3-(diphenylmethyloxy)propyl]piperidino]methyl]-2H-furo[3,2-e]indole dihydrochloride According to the same manner as that of Example 10, the title compound was synthesized from 1,6,7,8-tetrahydro-2-(iodomethyl)-2,4,5-trimethyl-2H-furo[3,2-e]indole and 4-[3-(diphenylmethyloxy)propyl]piperidine.

Yield 29%

Amorphous

NMR date for a free base are described below,

¹H-NMR (CDCl₃) δ 1.10–1.32 (4H, m), 1.41 (3H, s), 1.45 1.64 (4H, m), 2.01–2.17 (8H, m), 2.49 (2H, d, J=13.9, 17.6 Hz), 2.64–3.11 (7H, m), 3.43–3.57 (4H, m), 5.31 (1H, s), 7.18–7.35 (10H, m).

Example 13

N-Methyl-N-[1-[(1,6,7,8-tetrahydro-2,4,5,7,7-pentamethyl-2H-furo[3,2-e]indol-2-yl)methyl]-4-piperidinyl]-1,3-benzothiazole-2-amine A suspension of 1,6,7,8-tetrahydro-2-(iodomethyl)-2,4,5,7,7-pentamethyl-2H-furo[3,2-e]indole (372 mg, 1.0 mmol), N-methyl-N-(4-piperidinyl)-1,3-benzothiazole-2-amine hydrochloride (427 mg, 1.5 mmol) and potassium carbonate (485 mg, 3.5 mmol) in N,N-dimethylacetamide (2 mL) was stirred at 180° C. for 6 hours under the nitrogen atmosphere. Water was added to the reaction mixture, and the mixture was extracted with ethyl acetate two times. The combined organic layers were washed with water and saturated brine, dried over magnesium sulfate, filtered, and concentrated under reduced pressure. The residue was subjected to basic silica gel column chromatography (hexane-ethyl acetate 10:1), and recrystallized from ethyl acetate-hexane to obtain 276 mg of the title compound.
Yield 56%
mp. 162–164° C.
¹H-NMR (CDCl₃) δ 1.34 (3H, s), 1.35 (3H, s), 1.44 (3H, s), 1.60–2.23 (4H, m), 2.00 (3H, s), 2.05 (3H, s), 2.23–2.46 (2H, m), 2.51 (1H, d, J=13.9 Hz), 2.60 (1H, d, J=13.9 Hz), 2.75 (1H, d, J=15.0 Hz), 2.76 (2H, s), 2.94–3.13 (2H, m), 3.07 (3H, s), 3.15–3.30 (1H, m), 3.83–4.03 (1H, m), 7.03 (1H, td, J=7.5, 1.1 Hz), 7.27 (1H, td, J=7.8, 1.3 Hz), 7.48–7.63 (2H, m)

Example 14

Ethyl 4-phenyl-1-[(1,6,7,8-tetrahydro-2,4,5-trimethyl-2H-furo[3,2-e]indol-2-yl)methyl]-3-piperidinecarboxylate dihydrochloride According to the same manner as that of Example 10, the title compound was synthesized from 1,6,7,8-tetrahydro-2-(iodomethyl)-2,4,5-trimethyl-2H-furo[3,2-e]indole and ethyl 4-phenyl-3-piperidinecarboxylate.

Yield 73%
Amorphous
NMR data for a free base are described below.
¹H-NMR (CDCl₃) δ 0.97 (1.5H, t, J=7.1 Hz), 1.10 (1.5H, t, J=17.1 Hz), 1.39 (2.5H, s), 1.41 (1.5H, s), 1.6–1.83 (1H, m), 2.01–2.07 (6H, m), 2.22–3.20 (9H, m), 3.30–3.52 (4H, m), 3.77–4.02 (2H, m), 7.11–7.30 (5H, m)

Example 15

1,6,7,8-Tetrahydro-2,2,4,5-tetramethyl-1-(4-methylphenyl)-2H-furo[3,2-e]indole

To a solution of 4-bromo-1-(tert-butoxycarbonyl)-6,7-dimethyl-5-methoxy-1,2-dihydro-1H-indole-(1.60 g, 5.1 mmol) in THF (16 mL) was added dropwise a 1.5 M n-butyllithium solution (3.4 mL, 5.1 mmol) at −78° C. After stirred at the same temperature for 15 minutes, 2-methyl-1-(4-methylphenyl)-1-propanone (0.83 g, 5.1 mmol) was added, and a temperature was raised gradually to room temperature. After stirred for 30 minutes, water was poured, and extracted with ethyl acetate. The organic layer was washed with an aqueous saturated sodium bicarbonate solution and saturated brine, dried over sodium sulfate, and concentrated under reduced pressure. The residue was dissolved in acetic acid (10 mL), 48% hydrobromic acid (5 mL) was added, and stirred for 3 hours under reflux. The reaction solution was concentrated under reduced pressure, a 10%-aqueous potassium carbonate solution was added to neutralize, and the mixture was extracted with ethyl acetate. The organic layer was washed with saturated brine, dried over sodium sulfate, and concentrated under reduced pressure. The residue was purified with silica gel column chromatography (hexane-ethyl acetate, 5:1). The solvent was distilled off under reduced pressure, and crystallized form hexane to obtain 0.36 g of the title compound as an oil.
Yield 26%
mp. 112–114° C.
¹H-NMR (CDCl₃) δ 0.98 (3H, s), 1.53 (3H, s), 2.08 (3H, s), 2.14 (3H, s), 2.32 (3H, s), 2.40–2.65 (2H, m), 2.93 (1H, br), 3.41 (2H, t, J=8.3 Hz), 4.19 (1H, s), 6.93 (2H, brd, J=7.6 Hz), 7.07 (2H, d, J=7.6 Hz)

The structures of the compounds obtained in Examples to 15 are shown in Table 1.

TABLE 1

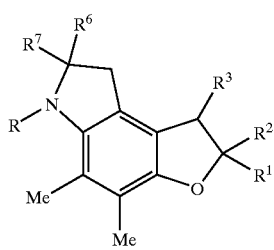

| Example No. | R | R¹ | R² | R³ | R⁶ | R⁷ |
|---|---|---|---|---|---|---|
| 1 | H | Me | Me | H | H | H |
| 2 | H | Me | Me | H | Me | H |
| 3 | H | Me | Me | H | Me | Me |
| 4 | CHO | Me | CH₂I | H | H | H |
| 5 | H | Me | CH₂I | H | H | H |
| 6 | CHO | Me | CH₂I | H | Me | Me |
| 7 | H | Me | CH₂I | H | Me | Me |

TABLE 1-continued

[Structure: tricyclic compound with N-R, R6, R7 on pyrrolidine ring; R3, R2, R1 on furan ring; two Me groups on benzene ring; O in furan]

| Example No. | R | R¹ | R² | R³ | R⁶ | R⁷ |
|---|---|---|---|---|---|---|
| 8 | H | Me | [1-ethyl-4-phenylpiperidine] | H | H | H |
| 9 | H | Me | [1-ethyl-4-phenylpiperidine] | H | Me | Me |
| 10 | H | Me | [2-ethyl-2,3,4,5-tetrahydro-1H-benzo[c]azepine] | H | Me | Me |
| 11 | H | Me | [1-ethylpiperidin-4-yl-NH-CHPh₂] | H | Me | Me |
| 12 | H | Me | [1-ethylpiperidin-4-yl-CH₂CH₂-O-CHPh₂] | H | H | H |
| 13 | H | Me | [1-ethylpiperidin-4-yl-N(Me)-benzothiazol-2-yl] | H | Me | Me |
| 14 | H | Me | [ethyl 1-ethyl-4-phenylpiperidine-3-carboxylate] | H | H | H |
| 15 | H | Me | Me | 4-MePh | Me | Me |

| Preparation Example 1 | | |
|---|---|---|
| (1) | Example compound 1 | 10.0 g |
| (2) | Lactose | 60.0 g |
| (3) | Corn Starch | 35.0 g |
| (4) | Gelatin | 3.0 g |
| (5) | Magnesium stearate | 2.0 g |

A mixture of 10.0 g of the compound, 60.0 g of lactose and 30.0 g of corn starch was granulated by passing through a 1 mm mesh sieve using a 30 ml of 10% by weight aqueous gelatin solution (3.0 g as gelatin), dried at 40° C. and passed again through a sieve. The resulting granule was mixed with 2.0 g of magnesium stearate, and compressed. The resulting core tablet was coated with a sugar coating of a suspension of sucrose, titanium dioxide, talc and gum arabic in water. The coated tablet was polished with yellow bees wax to obtain 1000 coated tablets.

| Preparation Example 2 | | |
|---|---|---|
| (1) | Example compound 11 | 10.0 g |
| (2) | Lactose | 70.0 g |
| (3) | Corn starch | 50.0 g |
| (4) | Soluble starch | 7.0 g |
| (5) | Magnesium stearate | 3.0 g |

10.0 g of the compound and 3.0 g of magnesium stearate were granulated with 70 ml of an aqueous solution of soluble starch (7.0 g as soluble starch), dried, and mixed with 70.0 g of lactose and 50.0 g of corn starch. The mixture was compressed to obtain 1000 tablets.

| Preparation Example 3 | | |
|---|---|---|
| (1) | Example compound 11 | 1.0 g |
| (2) | Lactose | 60.0 g |
| (3) | Corn starch | 35.0 g |
| (4) | Gelatin | 3.0 g |
| (5) | Magnesium stearate | 2.0 g |

A mixture of 1.0 g of the compound and a mixture of 60.0 g of lactose and 35.0 g of corn starch was granulated by passing through a 1 mm mesh sieve using 30 mL of a 10% by weight aqueous gelatin solution (3.0 g as gelatin) dried at 40° C. and passed again through a sieve. The resulting granule was mixed with 2.0 g of magnesium stearate, and pressed. The resulting core tablet was coated with a sugar coating of a suspension of sucrose, titanium dioxide, talc and gum arabic in water. The coated tablet was polished with yellow bees wax to obtain 1000 coated tablets.

Test Example

Inhibitory effect on lipid peroxidation in rat cerebral cortical homogeneates and oral administration to mouse.

Quantitative determination of lipoperoxide produced in brain homogenate was performed according to the method of Stocks et al. (Clin. Sci. Mol. Med. 47–215(1974)). As animals, brains of Jcl. Wistar male rats, 10–13 weeks age, were used. Rat cerebral cortices were obtained after decapitation, homogenized in an ice-cooled phosphate saline buffer (50 mM Ph 7.4) (Nichion Microhomogenizer, S-310E), centrifuged at 10,000 g for 10 minutes (Hitachi CF15D type, RT15A6 Anglerotor), and the supernatant was used in a test. This supernatant was diluted 3-fold with the same buffer. To this 1 mL were added 10 $\mu$L of test drugs dissolved in dimethyl sulfoxide (DMSO) to the final concentration of 0.0125, 0.025, 0.05, 0.10, 0.20, 0.40, 0.80 and 1.60 $\mu$M, respectively, which was incubated at 37° C. for 30 minutes. The reaction was stopped by addition of 200 $\mu$L of 35% perchloric acid, and centrifuged at 13,000 g for 10 minutes. To 1 mL of this supernatant was added 0.5 mL of 2-thiobarbituric acid (500 mg/100 mL) dissolved in 50% acetic acid, heated to boil at 95° C. for 15 minutes, which was determined by the absorbance at 532 nm. An inhibition rate was obtained from an amount of produced lipoperoxide at each concentration of the compound and an amount of lipoperoxide in a DMSO-added group, and $IC_{50}$ value of a compound was obtained from the inhibition rate.

The results are shown in Table 2.

TABLE 2

| Example compound | $IC_{50}$ ($\mu$M) |
|---|---|
| 3 | 0.127 |
| 11 | 0.057 |

From the foregoing results, it is seen that Compound I has the excellent inhibitory activity of lipid peroxidation.

INDUSTRIAL APPLICABILITY

Compound (I) or (I') of the present invention has the excellent inhibitory activity of lipid peroxidation and is useful as an agent for inhibiting lipoperoxide production.

What is claimed is:
1. A compound represented by the formula:

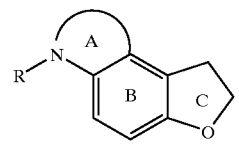

wherein A ring denotes a non-aromatic 5-membered nitrogen-containing heterocyclic ring of at least one nitrogen atom and carbon atoms and may have a further substituent selected from the group consisting of:
an optionally substituted hydrocarbon group,
an optionally halogenated lower alkoxy group,
an optionally halogenated lower alkylthio group,
a halogen atom,
an aryloxy group,
a lower alkanoyl group,
an arylcarbonyl group,
a lower alkanoyloxy group,
an arylcarbonyloxy group,
a carboxyl group,
a lower alkoxy-carbonyl group,
a carbamoyl group,
a thiocarbamoyl group,
a mono-lower alkylcarbamoyl group,
a di-lower alkylcarbamoyl group,
a $C_{6-10}$ aryl-carbamoyl group,
an amidino group,
an imino group,
an amino group,
a mono-lower alkylamino group,
a di-lower alkylamino group,
a 3- to 6-membered cyclic amino group optionally containing 1 to 3 heteroatoms selected from the group consisting of oxygen atom, sulfur atom and nitrogen atom, in addition to carbon atoms and one nitrogen atom, an alkylenedioxy group,
a hydroxy group,
a nitro group,
a cyano group,
a mercapto group,
a sulfo group,
a sulfino group,
a phosphono group,
a sulfamoyl group,
a mono-lower alkylsulfamoyl group,
a di-lower alkylsulfamoyl group, an arylthio group,
a lower alkylsulfinyl group,
an arylsulfinyl group,
a lower alkylsulfonyl group, and
an aryl sulfonyl group;
B ring denotes a benzene ring which may be further substituted;
C ring denotes a dihydrofuran ring which may be further substituted; and
R denotes hydrogen atom or an acyl group;
or a salt thereof.

2. The compound according to claim 1, wherein A ring is a non-aromatic 5-membered nitrogen-containing heterocyclic ring which may be further substituted with an optionally substituted hydrocarbon group.

3. The compound according to claim 1, wherein A ring is a non-aromatic 5-membered nitrogen-containing heterocyclic ring which may be further substituted with an optionally substituted lower alkyl group.

4. The compound according to claim 1, wherein A ring is a non-aromatic 5-membered nitrogen-containing heterocyclic ring which may be further substituted with a lower alkyl group.

5. The compound according to claim 1, wherein B ring is a wholly substituted benzene ring.

6. The compound according to claim 1 which is a compound represented by the formula:

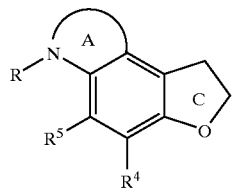

wherein $R^4$ and $R^5$ are the same or different and each denotes hydrogen atom, a halogen atom, hydroxy group, amino group, or an optionally substituted hydrocarbon group which may be via oxygen atom, nitrogen atom or sulfur atom, and other symbols are as defined in claim 1, provided that both $R^4$ and $R^5$ do not denote hydrogen atom at the same time, or a salt thereof.

7. The compound according to claim 6, wherein $R^4$ and $R^5$ are the same or different and each is a lower alkyl group or a lower alkoxy group.

8. The compound according to claim 6, wherein $R^4$ and $R^5$ are a lower alkyl group.

9. The compound according to claim 1 which is a compound represented by the formula:

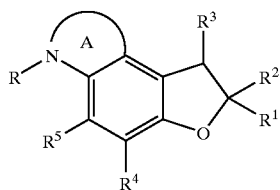

wherein $R^1$ and $R^2$ are the same or different and each denotes hydrogen atom, an optionally esterified or amidated carboxyl group or an optionally substituted hydrocarbon group, R denotes hydrogen atom, an optionally substituted hydrocarbon group or an optionally substituted amino group, $R^4$ and $R^5$ are the same or different and each denotes hydrogen atom, a halogen atom, hydroxy group, amino group, or an optionally substituted hydrocarbon group which may be via oxygen atom, nitrogen atom or sulfur atom and other symbols are as defined in claim 1, or a salt thereof.

10. The compound according to claim 9, wherein $R^1$ is a lower alkyl group, $R^2$ is a lower alkyl group which may be substituted with an optionally substituted cyclic amino, a halogen atom or a hydroxy, and $R^3$ is hydrogen atom or an optionally substituted phenyl group.

11. The compound according to claim 9, wherein $R^1$ is a lower alkyl group, $R^2$ is a lower alkyl group which may be substituted with an optionally substituted cyclic amino group, a halogen atom or a hydroxy, $R^3$ is hydrogen atom or an optionally substituted phenyl group, $R^4$ and $R^5$ are a lower alkyl group, and A ring is a non-aromatic 5-membered nitrogen-containing heterocyclic ring which may be further substituted with a lower alkyl group.

12. The compound according to claim 9, wherein $R^1$ is a lower alkyl group, $R^2$ is a lower alkyl group which may be substituted with an optionally substituted cyclic amino group, a halogen atom or a hydroxy, $R^3$ is hydrogen atom or an optionally substituted phenyl group, $R^4$ and $R^5$ are independently a lower alkyl group, and A ring is a non-aromatic 5-membered nitrogen-containing heterocyclic ring which may be further substituted with a lower alkyl group.

13. The compound according to claim 1 which is 1,6,7,8-tetrahydro-2,2,4,5-tetramethyl-1-(4-methylphenyl)-2H-furo[3,2-e]indole or a salt thereof.

14. The compound according to claim 1 which is 1,6,7,8-tetrahydro-2,4,5-trimethyl-2-[(4-phenylpiperidino)methyl]-2H-furo[3,2-e]indole or a salt thereof.

15. The compound according to claim 1 which is 1,6,7,8-tetrahydro-2,4,5,7,7-pentamethyl-2-[(4-phenylpiperidino)methyl]-2H-furo[3,2-e]indole or a salt thereof.

16. The compound according to claim 1 which is N-(diphenylmethyl)-1-[(1,6,7,8-tetrahydro-2,4,5,7,7-pentamethyl-2H-furo[3,2-e]indol-2-yl)methyl]-4-piperidineamine or a salt thereof.

17. A process for preparing the compound according to claim 1 which comprises ring-closing a substituent X and hydroxy group on B ring of a compound represented by the formula:

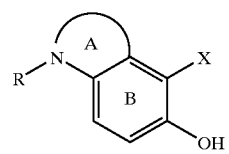

wherein X denotes an optionally substituted allyl group, and other symbols are as defined in claim 1, or a salt thereof.

18. A pharmaceutical composition which comprises a compound of claim 1 or a salt thereof, and a pharmacologically acceptable carrier.

19. A method for treating restenosis after percutaneous transluminal coronary angioplasty which comprises administering a compound represented by the formula:

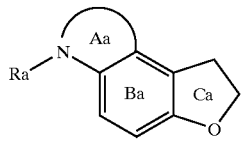

wherein Aa ring denotes a non-aromatic 5-membered nitrogen-containing heretocyclic ring which may be further substituted, Ba ring denotes a benzene ring which may be further substituted, Ca ring denotes a dihydrofuran ring which may be further substituted, and Ra denotes hydrogen atom or an acyl group, or a salt thereof, to a mammal.

20. A method for treating Alzheimer's disease which comprises administering a compound represented by the formula:

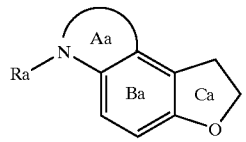

wherein Aa ring denotes a non-aromatic 5-membered nitrogen-containing heretocyclic ring which may be further substituted, Ba ring denotes a benzene ring which may be further substituted, Ca ring denotes a dihydrofuran ring which may be further substituted, and Ra denotes hydrogen atom or an acyl group, or a salt thereof, to a mammal.

* * * * *